United States Patent [19]
Lemmon

[11] Patent Number: 5,969,124
[45] Date of Patent: *Oct. 19, 1999

[54] NUCLEOTIDE SEQUENCE OF L1CAM

[75] Inventor: Vance Lemmon, Shaker Heights, Ohio

[73] Assignee: Case Western Reserve University, Cleveland, Ohio

[*] Notice: This patent is subject to a terminal disclaimer.

[21] Appl. No.: 08/427,497

[22] Filed: Apr. 24, 1995

Related U.S. Application Data

[63] Continuation of application No. 07/953,493, Sep. 28, 1992, abandoned, which is a continuation-in-part of application No. 07/904,991, Jun. 26, 1992, abandoned.

[51] Int. Cl.$^6$ .......................... C12N 15/12; C12N 15/11; C12N 15/10; C12N 5/10
[52] U.S. Cl. .................... 536/23.5; 435/69.1; 435/172.3; 536/23.1
[58] Field of Search ................................ 536/23.1, 23.5; 435/69.1, 172.3

[56] References Cited

FOREIGN PATENT DOCUMENTS

WO 92/03471  3/1992  WIPO.

OTHER PUBLICATIONS

Abribat et al., "Characterization of [$^{125}$I–Try$^{10}$]human growth hormone–releasing factor (1–44) amide binding to rat pituitary: evidence for high and low affinity classes of sites" Brain Res., 528:291 (1990).
Abribat et al., "Alterations of Pituitary Growth Hormone–Releasing Factor Binding Sites in Aging Rats", Endocrinology, 128:633 (1990).
Bagnato et al., "Gonadotropin–Induced Expression of Receptors for Growth Hormone Releasing Factor in Cultured Granulosa Cells*" Endocrinology 128:2889 (1991).
Bagnato et al., "Expression of the Growth Hormone–Releasing Hormone Gene and Its Peptide Product in the Rat Ovary*" Endocrinology 130:1097 (1991).
Barinaga et al., "Transcriptional Regulation of Growth Hormone Gene Expression by Growth Hormone–Releasing Factor" Nature 306:84 (1983).
Berry et al., "Ontogeny and Pituitary Regulation of Testicular Growth Hormone Releasing Hormone–Like Messenger Ribonucleic Acid*" Endocrinology 127:1404 (1990).
Bilezikjian et al., "Stimulation of Adenosine 3',5'–Monophosphate Production by Growth Hormone–Releasing Factor and Its Inhibition by Somatostatin in Anterior Pituitary Cells in Vitro*" Endocrinology 113:1726 (1982).
Billestrup et al., "Growth Hormone–Releasing Factor Induces c–fos Expression in Cultured Primary Pituitary Cells*" Mol. Endocrinology 1:301 (1987).
Billestrup et al., "Growth Hormone–Releasing Factor Stimulates Proliferation of Somatotrophs in vitro", Proc. Natl. Acad. Sci. USA 83:6854 (1986).
Bodner et al., "The Pituitary–Specific Transcription Factor GHF–1 Is a Homeobox–Containing Protein" Cell 55:505 (1988).

Canonico et al. "Human Pancreatic GRF Stimulates Phosphatidylinositol Labeling in Cultured Anterior Pituitary Cells" Am. Physiological Soc. p. 587 (1983).
Cooper, "Oncogenes and anti–oncogenes" Current Opinion in Cell Bio. 2:285 (1990).
Czech, "Signal Transmission by the Insulin–like Growth Factors" Cell 59:235 (1989).
Downs et al., "Evidence for a Defect in Growth Hormone–Releasing Factor Signal Transduction in the Dwarf (dw/dw) Rat Pituitary" Endocrinology 129:58 (1991).
Eicher et al., "Inherited Ateliotic Dwarfism in Mice" The J. of Heredity 67:87 (1976).
Frohman et al., "Growth Hormone–Releasing Hormone" Endocrine Reviews 7:223 (1986).
Gelato et al., "Growth Hormone Releasing Hormone$^1$" Am. Rev. Physiol. 48:569 (1986).
Gick et al., "Growth hormone–releasing factor regulates growth hormone mRNA in primary cultures of rat pituitary cells" Proc. Natl. Acad. Sci. USA 81:1553 (1984).
Giros et al. "Alternative splicing directs the expression of two $D_2$ dopamine receptor isoforms" Nature 342:923 (1989).
Godowski et al., "Characterization of the human growth hormone receptor gene and demonstration of a partial gene deletion in two patients with Laron–type dwarfism" Proc. Natl. Acad. sci. USA 86:8083 (1989).
Guillemin, "Growth Hormone–Releasing Factor from a Human Pacreatic Tumor That Caused Acromegaly" Science 218:585 (1982).
Hall et al., "Growth and Somatomedins" Vitamins and Hormones 40:175 (1983).
Humbel, "Insulin–like Growth Factors I and II" Eur. J. Biochem. 190:445 (1990).
Ingraham et al., "A Tissue–Specific Transcription Factor Containing a Homeodomain Specifies a Pituitary Phenotype" Cell 55:519 (1988).

(List continued on next page.)

Primary Examiner—Johnny F. Railey, II
Attorney, Agent, or Firm—Fay, Sharpe, Beall, Fagan, Minnich & McKee

[57] ABSTRACT

The present invention is directed to the isolation and purification of an L1-like molecule (i.e. L1CAM) from human brain. It has been found that the isolated L1CAM molecule supports neurite growth in vitro. Applicants have also cloned and sequenced the entire coding region of human L1CAM, and found that it shows a very high degree of homology to mouse L1cam with 92% identity at the amino acid level. This similarity suggest that L1CAM is an important molecule in normal human nervous system development and nerve regeneration. Overall, there is substantially less homology to chick Ng-CAM; they are 40% identical at the amino acid level but many regions are highly conserved. Comparison of the sequences from human, mouse, chick and Drosophila, indicates that the L1 immunoglobulin domain 2 and fibronectin type III domain 2 are strongly conserved and thus are likely functionally important.

5 Claims, 6 Drawing Sheets

OTHER PUBLICATIONS

Ishihara et al., "Molecular cloning and expression of a cDNA encoding the secretin receptor" The EMBO Journal 10;1635 (1991).

Ishihara et al., Functional Expression and Tissue Distribution of a Novel Receptor for Vasoactive Intestinal Polypeptide Neuron 8:811 (1992).

Jansson et al., "Receptor–Associated Resistance to Growth Hormone–Releasing Factor in Dwarf "Little" Mice", Science, 232:511 (1986).

Juppner et al., A G Protein–Linked Receptor for Parathyroid Hormone and Parathyroid Hormone–Related Peptide, Science, 254:1024 (1991).

Kelly et al., "The Prolactin/Growth Hormone Receptor Family", Endo. Rev., 12:235 (1991).

Kyte et al, "A Simple Method for Displaying the Hydropathic Character of a Protein" J. Mol. Biol., 157:105–132 (1982).

Labrie et al., "Growth Hormone–Releasing Factor Stimulates Adenylate Cyclase Activity in the Anterior Pituitary Gland", Life Sci., 33:2229–2233 (1983).

Landis et al., "GTPase inhibiting mutations activate the α chain of $G_s$ and stimulate adenylyl cyclase in human pituitary tumors", Nature 340:692 (1989).

Leung et al., "Growth Hormone Receptor and Serum Binding Protein: Purification, Cloning and Expression", Nature, 330:537 (1987).

Libert et al., "Selective Amplification and Cloning of Four New Members of the G Protein–Coupled Receptor Family", Science, 244:569 (1989).

Lin et al., "Expression Cloning of an Adenylate Cyclase–Coupled Calcitonin Receptor" Science, 254:1022 (1991).

Login et al., "Association of $^{45}Ca^{2+}$ Mobilization with Stimulation of Growth Hormone (GH) Release by GH–Releasing Factor in Dispersed Normal Male Rat Pituitary Cells*", Endocrinology 118:239 (1986).

MacGillivray, "Disorders of Growth and Development", Part VIII Miscellaenous Disorders 26:1581 (1986).

Margioris et al., "Expression and Localization of Growth Hormone–Releasing Hormone Messneger Ribonucleic Acid in Rat Placenta: In Vitra Secreation and Regulation of its Peptide Product", Endocrinology 126:151 (1990).

Martin, "Brain Mechanisms for Integration of Growth Hormones Secretion", Twenty Third Annual Bowditch Lecture 23–29 (1986).

Mayo et al., "Dramatic Pituitary Hyperplasia in Transgenic Mice Expressing a Human Growth Hormone–Releasing Factor Gene", Mol. Endo. 2:606 (1988).

Miyata et al., "Isolation of a Novel 38 Residue–Hypothalamic Polypeptide which Stimulates Adenylate Cyclase in Pituitary Cells", Biochem. and Biophy. Res. Comm. 164:567–574 (1989).

Monsma et al., "Multiple $D_2$ dpoamine receptors produced by alternative RNA splicing" Letters to Nature 342:926 (1989).

Moretti et al., "Receptor–Mediated Actions of Growth Hormone Releasing Factor on Granulos Cell Differentiation", Endocrinology 127:2117 (1990).

Morgan et al., "Insulin–like growth factor II receptor as a multifunctional binding protein", Nature 329:301 (1987).

O'Dowd et al., "Site–directed Mutagenesis of the Cytoplasmic Domains of the Human $\beta_2$–Adrenergic Receptor", The J. of Bio. Chem. 263:15985–15992 (1988).

O'Dowd et al., "Structure of the Adrenergic and Related Receptors", Ann. Rev. Neurosci 12:67–83 (1989).

Rivier et al., "Characterization of a growth hormone–releasing factor from a human pancreatic islet tumour", Nature 300:276 (1982).

Robberecht et al., "Decreased Stimulation of Adenylate Cyclase by Growth Hormone–Releasing Factor in the Anterior Pituitary of Old Rats", Neuroendocrinology 44:429–432 (1986).

Ross, "Signal Sorting and Amplification through G Protein––Coupled Receptors", Neuron 3:141–152 (1989).

Seifert et al., "Growth Hormone–Releasing Factor Binding Sites in Rat Anterior Pituitary Membrane Homogenates: Modulation by Glucocorticoids", Endo. 117:424 (1985).

Seifert et al., "Binding sites for growth hormone releasing factor on rat anterior pituitary cells", Nature 313:487 (1985).

Southern et al., "Transformation of Mammilian Cells to Antibiotic Resistance with a Bacterial Gene Under Control of the SV40 Early Region Promoter", J. of Mol. and Applied Gen. 1:327–341 (1982).

Spicer et al., "Effects of growth hormone–releasing factor and vasoactive intestinal peptide on proliferation and steriodogenesis of bovine granulosa cells", Mol. and Cell. Endo. 83:73–78 (1992).

Strader et al., "Structural basis of β–adrenergic receptor function", The FASEB J. 3:1825 (1989).

Struthers et al., "Nucleotide Regulation of Growth Hormone–Releasing Factor Binding to Rat Pituitary Receptors*", Endorcinology 124:24 (1989).

Suhr et al., "Mouse Growth Hormone–Releasing Hormone: Precursor Structure and Expression in Brain and Placenta", Mol. Endo. 3:1693–1700 (1989).

Ullrich et al., "Insulin–like growth factor I receptor primary structure: comparison with insulin receptor suggests structural determinants that define functional specificity", The EMBO J. 5:2503 (1986).

Underwood et al., "Normal and Aberrant Growth", Growth and Reproduction, 3:155–205 (1986).

Vallar et al., "Altered $G_s$ and adenylate cyclase activity in human GH–secreting pituitary adenomas", Nature 330:566 (1987).

Velicelebi et al., "Specific Binding of Synthetic Human Pancreatic Growth Hormone Releasing Factor (1–40–OH) to Bovine Anterior Pituitaries", Biochem and Biophy. Res. Comm. 126:33–39 (1985).

Velicelbi et al., "Covalent Cross–Linking of Growth Hormone–Releasing Factor to Pituitary Receptors", Endocrinology 118:1278 (1986).

Wehrenberg et al., "Ontogeny of growth hormone–releasing factor and its role in fetal and neonatal growth", Advances in Growth Hormone and Growth Factor Research, 203–263 (1989).

Yamada et al., "Cloning and functional characterization of a family of human and mouse somatostatin receptors expressedin brain gastrointestinal tract, and kidney", Proc. Natl. Acad. Sci. USA 89:251–255 (1992).

Zysk et al., "Cross–linking of a Growth Hormone Releasing Factor–binding Protein in Anterior Pituitary Cells*", The J. of Bio. Chem., 261:16781 (1986).

Harper et. al 1991, Journal of Neurochemistry 56(3): 797–804.

Moos et. al. 1988, Nature 334: 701–703.

Watson et. al. Recombinant DNA: A Short Course pp. 76–78, Scientific American Books, New York.

Wallace et. al. 1987. Methods in Enzymology 152:432–442.

Transmembrane

```
1097 Mouse L1  TT-S--S-----A----------I-------
1095 Human L1  PAG FATEGWFIGFVSAIILLLVLLILCFI
1102 Ng-CAM    -G-GVC-K------SVV----I-------
```

Cytoplasmic

```
1097 Mouse L1  ----------------------------------------------------------   PLGSDDSLADYGGSVDVQFNEDGSFIGQYSGKKEKEAAGGNDSSGATSPINPAVALE
1095 Human L1  KRSKGGKYSVKDKEDTQVDSEARPMKDETFGEYRSLESDNEEK AFGSSQPSLNGDIK ----------------------------------------------------------
1102 Ng-CAM    ------------------------------------------EA-KGS-S-GAG-GV-SPGRGPCAA--E----G------G-----------R-PGAGPGSS-PA-SG-GP-LD
```

FIGURE 4B

SEQUENCE LISTING

```
(1) GENERAL INFORMATION:

(iii) NUMBER OF SEQUENCES:    44

(2) INFORMATION FOR SEQ ID NO: 1:

(i) SEQUENCE CHARACTERISTICS:
         (A) LENGTH: 3774
         (B) TYPE: nucleic acid
         (C) STRANDEDNESS:  single
         (D) TOPOLOGY:  linear (ii) MOLECULE TYPE:  nucleic acids (iii) HYPOTHETICAL:    irrelevant (iv) ANTI-SENSE: no (vi) ORIGINAL SOURCE:
         (A) ORGANISM: Homo Sapiens
         (B) INDIVIDUAL ISOLATE: 17-18 week fetus (vii) IMMEDIATE SOURCE:
         (A) LIBRARY: Stratagene cDNA Library 936206
         (B) CLONE: synthesis of 4 clones (x) PUBLICATION INFORMATION:
         (A) AUTHORS:       Hlavin, Mary Louise
             Lemmon, Vance
         (B) TITLE:         Molecular structure and functional
             testing of human L1CAM: an
             interspecies comparison.
         (C) JOURNAL:       GENOMICS
         (D) VOLUME:        11
         (E) ISSUE:
         (F) PAGES:         416-423
         (G) DATE:          1991
         (K) RELEVANT RESIDUES IN SEQ ID NO:  1 to 3774
```

(xi) SEQUENCE DESCRIPTION: SEQ ID NO: 1:

```
ATG GTC GTG GCG CTG CGG TAC GTG TGG CCT CTC CTC CTC TGC AGC CCC      48
Met Val Val Ala Leu Arg Tyr Val Trp Pro Leu Leu Leu Cys Ser Pro
 1               5                  10                  15

TGC CTG CTT ATC CAG ATC CCC GAG GAA TAT GAA GGA CAC CAT GTG ATG      96
Cys Leu Leu Ile Gln Ile Pro Glu Glu Tyr Glu Gly His His Val Met
                 20                  25                  30

GAG CCA CCT GTC ATC ACG GAA CAG TCT CCA CGG CGC CTG GTT GTC TTC     144
Glu Pro Pro Val Ile Thr Glu Gln Ser Pro Arg Arg Leu Val Val Phe
             35                  40                  45

CCC ACA GAT GAC ATC AGC CTC AAG TGT GAG GCC AGT GGC AAG CCC GAA     192
Pro Thr Asp Asp Ile Ser Leu Lys Cys Glu Ala Ser Gly Lys Pro Glu
         50                  55                  60

GTG CAG TTC CGC TGG ACG AGG GAT GGT GTC CAC TTC AAA CCC AAG GAA     240
Val Gln Phe Arg Trp Thr Arg Asp Gly Val His Phe Lys Pro Lys Glu
 65              70                  75                  80

GAG CTG GGT GTG ACC GTG TAC CAG TCG CCC CAC TCT GGC TCC TTC ACC     288
Glu Leu Gly Val Thr Val Tyr Gln Ser Pro His Ser Gly Ser Phe Thr
                 85                  90                  95

ATC ACG GGC AAC AAC AGC AAC TTT GCT CAG AGG TTC CAG GGC ATC TAC     336
Ile Thr Gly Asn Asn Ser Asn Phe Ala Gln Arg Phe Gln Gly Ile Tyr
                100                 105                 110

CGC TGC TTT GCC AGC AAT AAG CTG GGC ACC GCC ATG TCC CAT GAG ATC     384
Arg Cys Phe Ala Ser Asn Lys Leu Gly Thr Ala Met Ser His Glu Ile
            115                 120                 125

CGG CTC ATG GCC GAG GGT GCC CCC AAG TGG CCA AAG GAG ACA GTG AAG     432
Arg Leu Met Ala Glu Gly Ala Pro Lys Trp Pro Lys Glu Thr Val Lys
        130                 135                 140

CCC GTG GAG GTG GAG GAA GGG GAG TCA GTG GTT CTG CCT TGC AAC CCT     480
Pro Val Glu Val Glu Glu Gly Glu Ser Val Val Leu Pro Cys Asn Pro
145                 150                 155                 160

CCC CCA AGT GCA GAG CCT CTC CGG ATC TAC TGG ATG AAC AGC AAG ATC     528
Pro Pro Ser Ala Glu Pro Leu Arg Ile Tyr Trp Met Asn Ser Lys Ile
                165                 170                 175

TTG CAC ATC AAG CAG GAC GAG CGG GTG ACG ATG GGC CAG AAC GGC AAC     576
Leu His Ile Lys Gln Asp Glu Arg Val Thr Met Gly Gln Asn Gly Asn
                180                 185                 190

CTC TAC TTT GCC AAT GTG CTC ACC TCC GAC AAC CAC TCA GAC TAC ATC     624
Leu Tyr Phe Ala Asn Val Leu Thr Ser Asp Asn His Ser Asp Tyr Ile
            195                 200                 205

TGC CAC GCC CAC TTC CCA GGC ACC AGG ACC ATC ATT CAG AAG GAA CCC     672
Cys His Ala His Phe Pro Gly Thr Arg Thr Ile Ile Gln Lys Glu Pro
        210                 215                 220

ATT GAC CTC CGG GTC AAG GCC ACC AAC AGC ATG ATT GAC AGG AAG CCG     720
Ile Asp Leu Arg Val Lys Ala Thr Asn Ser Met Ile Asp Arg Lys Pro
225                 230                 235                 240

CGC CTG CTC TTC CCC ACC AAC TCC AGC AGC CAC CTG GTG GCC TTG CAG     768
Arg Leu Leu Phe Pro Thr Asn Ser Ser Ser His Leu Val Ala Leu Gln
                245                 250                 255

GGG CAG CCA TTG GTC CTG GAG TGC ATC GCC GAG GGC TTT CCC ACG CCC     816
Gly Gln Pro Leu Val Leu Glu Cys Ile Ala Glu Gly Phe Pro Thr Pro
                260                 265                 270

ACC ATC AAA TGG CTG CGC CCC AGT GGC CCC ATG CCA GCT GAC CGT GTC     864
Thr Ile Lys Trp Leu Arg Pro Ser Gly Pro Met Pro Ala Asp Arg Val
            275                 280                 285

ACC TAC CAG AAC CAC AAC AAG ACC CTG CAG CTG CTG AAA GTG GGC GAG     912
Thr Tyr Gln Asn His Asn Lys Thr Leu Gln Leu Leu Lys Val Gly Glu
        290                 295                 300

GAG GAT GAT GGC GAG TAC CGC TGC CTG GCC GAG AAC TCA CTG GGC AGT     960
Glu Asp Asp Gly Glu Tyr Arg Cys Leu Ala Glu Asn Ser Leu Gly Ser
```

-continued

```
305             310             315             320
GCC CGG CAT GCG TAC TAT GTC ACC GTG GAG GCT GCC CCG TAC TGG CTG    1008
Ala Arg His Ala Tyr Tyr Val Thr Val Glu Ala Ala Pro Tyr Trp Leu
            325             330             335

CAC AAG CCC CAG AGC CAT CTA TAT GGG CCA GGA GAG ACT GCC CGC CTG    1056
His Lys Pro Gln Ser His Leu Tyr Gly Pro Gly Glu Thr Ala Arg Leu
            340             345             350

GAC TGC CAA GTC CAG GGC AGG CCC CAA CCA GAG GTC ACC TGG AGA ATC    1104
Asp Cys Gln Val Gln Gly Arg Pro Gln Pro Glu Val Thr Trp Arg Ile
            355             360             365

AAC GGG ATC CCT GTG GAG GAG CTG GCC AAA GAC CAG AAG TAC CGG ATT    1152
Asn Gly Ile Pro Val Glu Glu Leu Ala Lys Asp Gln Lys Tyr Arg Ile
            370             375             380

CAG CGT GGC GCC CTG ATC CTG AGC AAC GTG CAG CCC AGT GAC ACA ATG    1200
Gln Arg Gly Ala Leu Ile Leu Ser Asn Val Gln Pro Ser Asp Thr Met
385             390             395             400

GTG ACC CAA TGT GAG GCC CGC AAC CGG CAC GGG CTC TTG CTG GCC AAT    1248
Val Thr Gln Cys Glu Ala Arg Asn Arg His Gly Leu Leu Leu Ala Asn
            405             410             415

GCC TAC ATC TAC GTT GTC CAG CTG CCA GCC AAG ATC CTG ACT GCG GAC    1296
Ala Tyr Ile Tyr Val Val Gln Leu Pro Ala Lys Ile Leu Thr Ala Asp
            420             425             430

AAT CAG ACG TAC ATG GCT GTC CAG GGC AGC ACT GCC TAC CTT CTG TGC    1344
Asn Gln Thr Tyr Met Ala Val Gln Gly Ser Thr Ala Tyr Leu Leu Cys
            435             440             445

AAG GCC TTC GGA GCG CCT GTG CCC AGT GTT CAG TGG CTG GAC GAG GAT    1392
Lys Ala Phe Gly Ala Pro Val Pro Ser Val Gln Trp Leu Asp Glu Asp
            450             455             460

GGG ACA ACA GTG CTT CAG GAC GAA CGC TTC TTC CCC TAT GCC AAT GGG    1440
Gly Thr Thr Val Leu Gln Asp Glu Arg Phe Phe Pro Tyr Ala Asn Gly
465             470             475             480

ACC CTG GGC ATT CGA GAC CTC CAG GCC AAT GAC ACC GGA CGC TAC TTC    1488
Thr Leu Gly Ile Arg Asp Leu Gln Ala Asn Asp Thr Gly Arg Tyr Phe
            485             490             495

TGC CTG GCT GCC AAT GAC CAA AAC AAT GTT ACC ATC ATG GCT AAC CTG    1536
Cys Leu Ala Ala Asn Asp Gln Asn Asn Val Thr Ile Met Ala Asn Leu
            500             505             510

AAG GTT AAA GAT GCA ACT CAG ATC ACT CAG GGG CCC CGC AGC ACA ATC    1584
Lys Val Lys Asp Ala Thr Gln Ile Thr Gln Gly Pro Arg Ser Thr Ile
            515             520             525

GAG AAG AAA GGT TCC AGG GTG ACC TTC ACG TGC CAG GCC TCC TTT GAC    1632
Glu Lys Lys Gly Ser Arg Val Thr Phe Thr Cys Gln Ala Ser Phe Asp
            530             535             540

CCC TCC TTG CAG CCC AGC ATC ACC TGG CGT GGG GAC GGT CGA GAC CTC    1680
Pro Ser Leu Gln Pro Ser Ile Thr Trp Arg Gly Asp Gly Arg Asp Leu
545             550             555             560

CAG GAG CTT GGG GAC AGT GAC AAG TAC TTC ATA GAG GAT GGG CGC CTG    1728
Gln Glu Leu Gly Asp Ser Asp Lys Tyr Phe Ile Glu Asp Gly Arg Leu
            565             570             575

GTC ATC CAC AGC CTG GAC TAC AGC GAC CAG GGC AAC TAC AGC TGC GTG    1776
Val Ile His Ser Leu Asp Tyr Ser Asp Gln Gly Asn Tyr Ser Cys Val
            580             585             590

GCC AGT ACC GAA CTG GAT GTG GTG GAG AGT AGG GCA CAG CTC TTG GTG    1824
Ala Ser Thr Glu Leu Asp Val Val Glu Ser Arg Ala Gln Leu Leu Val
            595             600             605

GTG GGG AGC CCT GGG CCG GTG CCA CGG CTG GTG CTG TCC GAC CTG CAC    1872
Val Gly Ser Pro Gly Pro Val Pro Arg Leu Val Leu Ser Asp Leu His
            610             615             620

CTG CTG ACG CAG AGC CAG GTG CGC GTG TCC TGG AGT CCT GCA GAA GAC    1920
Leu Leu Thr Gln Ser Gln Val Arg Val Ser Trp Ser Pro Ala Glu Asp
```

-continued

| | | | | | | | | | | | | | | | |
|---|---|---|---|---|---|---|---|---|---|---|---|---|---|---|---|
| | | 625 | | | | 630 | | | | 635 | | | | 640 | |
| CAC | AAT | GCC | CCC | ATT | GAG | AAA | TAT | GAC | ATT | GAA | TTT | GAG | GAC | AAG | GAA | 1968 |
| His | Asn | Ala | Pro | Ile | Glu | Lys | Tyr | Asp | Ile | Glu | Phe | Glu | Asp | Lys | Glu | |
| | | | | 645 | | | | 650 | | | | | 655 | | | |
| ATG | GCG | CCT | GAA | AAA | TGG | TAC | AGT | CTG | GGC | AAG | GTT | CCA | GGG | AAC | CAG | 2016 |
| Met | Ala | Pro | Glu | Lys | Trp | Tyr | Ser | Leu | Gly | Lys | Val | Pro | Gly | Asn | Gln | |
| | | | | 660 | | | | | 665 | | | | 670 | | | |
| ACC | TCT | ACC | ACC | CTC | AAG | CTG | TCG | CCC | TAT | GTC | CAC | TAC | ACC | TTT | AGG | 2064 |
| Thr | Ser | Thr | Thr | Leu | Lys | Leu | Ser | Pro | Tyr | Val | His | Tyr | Thr | Phe | Arg | |
| | | | 675 | | | | | 680 | | | | | 685 | | | |
| GTT | ACT | GCC | ATA | AAC | AAA | TAT | GGC | CCC | GGG | GAG | CCC | AGC | CCG | GTC | TCT | 2112 |
| Val | Thr | Ala | Ile | Asn | Lys | Tyr | Gly | Pro | Gly | Glu | Pro | Ser | Pro | Val | Ser | |
| | | | 690 | | | | 695 | | | | | 700 | | | | |
| GAG | ACT | GTG | GTC | ACA | CCT | GAG | GCA | GCC | CCA | GAG | AAG | AAC | CCT | GTG | GAT | 2160 |
| Glu | Thr | Val | Val | Thr | Pro | Glu | Ala | Ala | Pro | Glu | Lys | Asn | Pro | Val | Asp | |
| 705 | | | | | 710 | | | | | 715 | | | | | 720 | |
| GTG | AAG | GGG | GAA | GGA | AAT | GAG | ACC | ACC | AAT | ATG | GTC | ATC | ACG | TGG | AAG | 2208 |
| Val | Lys | Gly | Glu | Gly | Asn | Glu | Thr | Thr | Asn | Met | Val | Ile | Thr | Trp | Lys | |
| | | | | 725 | | | | | 730 | | | | | 735 | | |
| CCG | CTC | CGG | TGG | ATG | GAC | TGG | AAC | GCC | CCC | CAG | GTT | CAG | TAC | CGC | GTG | 2256 |
| Pro | Leu | Arg | Trp | Met | Asp | Trp | Asn | Ala | Pro | Gln | Val | Gln | Tyr | Arg | Val | |
| | | | 740 | | | | | 745 | | | | | 750 | | | |
| CAG | TGG | CGC | CCT | CAG | GGG | ACA | CGA | GGG | CCC | TGG | CAG | GAG | CAG | ATT | GTC | 2304 |
| Gln | Trp | Arg | Pro | Gln | Gly | Thr | Arg | Gly | Pro | Trp | Gln | Glu | Gln | Ile | Val | |
| | | 755 | | | | | 760 | | | | | 765 | | | | |
| AGC | GAC | CCC | TTC | CTG | GTG | GTG | TCC | AAC | ACG | TCC | ACC | TTC | GTG | CCC | TAT | 2352 |
| Ser | Asp | Pro | Phe | Leu | Val | Val | Ser | Asn | Thr | Ser | Thr | Phe | Val | Pro | Tyr | |
| | 770 | | | | | 775 | | | | | 780 | | | | | |
| GAG | ATC | AAA | GTC | CAG | GCC | GTC | AAC | AGC | CAG | GGC | AAG | GGA | CCA | GAG | CCC | 2400 |
| Glu | Ile | Lys | Val | Gln | Ala | Val | Asn | Ser | Gln | Gly | Lys | Gly | Pro | Glu | Pro | |
| 785 | | | | | 790 | | | | | 795 | | | | | 800 | |
| CAG | GTC | ACT | ATC | GGC | TAC | TCT | GGA | GAG | GAC | TAC | CCC | CAG | GCA | ATC | CCT | 2448 |
| Gln | Val | Thr | Ile | Gly | Tyr | Ser | Gly | Glu | Asp | Tyr | Pro | Gln | Ala | Ile | Pro | |
| | | | | 805 | | | | | 810 | | | | | 815 | | |
| GAG | CTG | GAA | GGC | ATT | GAA | ATC | CTC | AAC | TCA | AGT | GCC | GTG | CTG | GTC | AAG | 2496 |
| Glu | Leu | Glu | Gly | Ile | Glu | Ile | Leu | Asn | Ser | Ser | Ala | Val | Leu | Val | Lys | |
| | | | 820 | | | | | 825 | | | | | 830 | | | |
| TGG | CGG | CCG | GTG | GAC | CTG | GCC | CAG | GTC | AAG | GGC | CAC | CTC | CGC | GGA | TAC | 2544 |
| Trp | Arg | Pro | Val | Asp | Leu | Ala | Gln | Val | Lys | Gly | His | Leu | Arg | Gly | Tyr | |
| | | | 835 | | | | | 840 | | | | | 845 | | | |
| AAT | GTG | ACG | TAC | TGG | AGG | GAG | GGC | AGT | CAG | AGG | AAG | CAC | AGC | AAG | AGA | 2592 |
| Asn | Val | Thr | Tyr | Trp | Arg | Glu | Gly | Ser | Gln | Arg | Lys | His | Ser | Lys | Arg | |
| | 850 | | | | | 855 | | | | | 860 | | | | | |
| CAT | ATC | CAC | AAA | GAC | CAT | GTG | GTG | GTG | CCC | GCC | AAC | ACC | ACC | AGT | GTC | 2640 |
| His | Ile | His | Lys | Asp | His | Val | Val | Val | Pro | Ala | Asn | Thr | Thr | Ser | Val | |
| 865 | | | | | 870 | | | | | 875 | | | | | 880 | |
| ATC | CTC | AGT | GGC | TTG | CGG | CCC | TAT | AGC | TCC | TAC | CAC | CTG | GAG | GTG | CAG | 2688 |
| Ile | Leu | Ser | Gly | Leu | Arg | Pro | Tyr | Ser | Ser | Tyr | His | Leu | Glu | Val | Gln | |
| | | | | 885 | | | | | 890 | | | | | 895 | | |
| GCC | TTT | AAC | GGG | CGA | GGA | TCG | GGG | CCC | GCC | AGC | GAG | TTC | ACC | TTC | AGC | 2736 |
| Ala | Phe | Asn | Gly | Arg | Gly | Ser | Gly | Pro | Ala | Ser | Glu | Phe | Thr | Phe | Ser | |
| | | | 900 | | | | | 905 | | | | | 910 | | | |
| ACC | CCA | GAG | GGA | GTG | CCT | GGC | CAC | CCC | GAG | GCG | TTG | CAC | CTG | GAG | TGC | 2784 |
| Thr | Pro | Glu | Gly | Val | Pro | Gly | His | Pro | Glu | Ala | Leu | His | Leu | Glu | Cys | |
| | | 915 | | | | | 920 | | | | | 925 | | | | |
| CAG | TCG | AAC | ACC | AGC | CTG | CTG | CTG | CGC | TGG | CAG | CCC | CCA | CTC | AGC | CAC | 2832 |
| Gln | Ser | Asn | Thr | Ser | Leu | Leu | Leu | Arg | Trp | Gln | Pro | Pro | Leu | Ser | His | |
| | 930 | | | | | 935 | | | | | 940 | | | | | |
| AAC | GGC | GTG | CTC | ACC | GGC | TAC | GTG | CTC | TCC | TAC | CAC | CCC | CTG | GAT | GAG | 2880 |
| Asn | Gly | Val | Leu | Thr | Gly | Tyr | Val | Leu | Ser | Tyr | His | Pro | Leu | Asp | Glu | |

```
                   945                 950                 955                 960
GGG GGC AAG GGG CAA CTG TCC TTC AAC CTT CGG GAC CCC GAA CTT CGG                    2928
Gly Gly Lys Gly Gln Leu Ser Phe Asn Leu Arg Asp Pro Glu Leu Arg
                    965                 970                 975

ACA CAC AAC CTG ACC GAT CTC AGC CCC CAC CTG CGG TAC CGC TTC CAG                    2976
Thr His Asn Leu Thr Asp Leu Ser Pro His Leu Arg Tyr Arg Phe Gln
                980                 985                 990

CTT CAG GCC ACC ACC AAA GAG GGC CCT GGT GAA GCC ATC GTA CGG GAA                    3024
Leu Gln Ala Thr Thr Lys Glu Gly Pro Gly Glu Ala Ile Val Arg Glu
            995                 1000                1005

GGA GGC ACT ATG GCC TTG TCT GGG ATC TCA GAT TTT GGC AAC ATC TCA                    3072
Gly Gly Thr Met Ala Leu Ser Gly Ile Ser Asp Phe Gly Asn Ile Ser
        1010                1015                1020

GCC ACA GCG GGT GAA AAC TAC AGT GTC GTC TCC TGG GTC CCC AAG GAG                    3120
Ala Thr Ala Gly Glu Asn Tyr Ser Val Val Ser Trp Val Pro Lys Glu
1025                1030                1035                1040

GGC CAG TGC AAC TTC AGG TTC CAT ATC TTG TTC AAA GCC TTG GGA GAA                    3168
Gly Gln Cys Asn Phe Arg Phe His Ile Leu Phe Lys Ala Leu Gly Glu
                1045                1050                1055

GAG AAG GGT GGG GCT TCC CTT TCG CCA CAG TAT GTC AGC TAC AAC CAG                    3216
Glu Lys Gly Gly Ala Ser Leu Ser Pro Gln Tyr Val Ser Tyr Asn Gln
            1060                1065                1070

AGC TCC TAC ACG CAG TGG GAC CTG CAG CCT GAC ACT GAC TAC GAG ATC                    3264
Ser Ser Tyr Thr Gln Trp Asp Leu Gln Pro Asp Thr Asp Tyr Glu Ile
        1075                1080                1085

CAC TTG TTT AAG GAG AGG ATG TTC CGG CAC CAA ATG GCT GTG AAG ACC                    3312
His Leu Phe Lys Glu Arg Met Phe Arg His Gln Met Ala Val Lys Thr
    1090                1095                1100

AAT GGC ACA GGC CGC GTG AGG CTC CCT CCT GCT GGC TTC GCC ACT GAG                    3360
Asn Gly Thr Gly Arg Val Arg Leu Pro Pro Ala Gly Phe Ala Thr Glu
1105                1110                1115                1120

GGC TGG TTC ATC GGC TTT GTG AGT GCC ATC ATC CTC CTG CTC CTC GTC                    3408
Gly Trp Phe Ile Gly Phe Val Ser Ala Ile Ile Leu Leu Leu Leu Val
                1125                1130                1135

CTG CTC ATC CTC TGC TTC ATC AAG CGC AGC AAG GGC GGC AAA TAC TCA                    3456
Leu Leu Ile Leu Cys Phe Ile Lys Arg Ser Lys Gly Gly Lys Tyr Ser
            1140                1145                1150

GTG AAG GAT AAG GAG GAC ACC CAG GTG GAC TCT GAG GCC CGA CCG ATG                    3504
Val Lys Asp Lys Glu Asp Thr Gln Val Asp Ser Glu Ala Arg Pro Met
        1155                1160                1165

AAA GAT GAG ACC TTC GGC GAG TAC AGG TCC CTG GAG AGT GAC AAC GAG                    3552
Lys Asp Glu Thr Phe Gly Glu Tyr Arg Ser Leu Glu Ser Asp Asn Glu
    1170                1175                1180

GAG AAG GCC TTT GGC AGC AGC CAG CCA TCG CTC AAC GGG GAC ATC AAG                    3600
Glu Lys Ala Phe Gly Ser Ser Gln Pro Ser Leu Asn Gly Asp Ile Lys
1185                1190                1195                1200

CCC CTG GGC AGT GAC GAC AGC CTG GCC GAT TAT GGG GGC AGC GTG GAT                    3648
Pro Leu Gly Ser Asp Asp Ser Leu Ala Asp Tyr Gly Gly Ser Val Asp
                1205                1210                1215

GTT CAG TTC AAC GAG GAT GGT TCG TTC ATT GGC CAG TAC AGT GGC AAG                    3696
Val Gln Phe Asn Glu Asp Gly Ser Phe Ile Gly Gln Tyr Ser Gly Lys
            1220                1225                1230

AAG GAG AAG GAG GCG GCA GGG GGC AAT GAC AGC TCA GGG GCC ACT TCC                    3744
Lys Glu Lys Glu Ala Ala Gly Gly Asn Asp Ser Ser Gly Ala Thr Ser
        1235                1240                1245

CCC ATC AAC CCT GCC GTG GCC CTA GAA TAG                                            3774
Pro Ile Asn Pro Ala Val Ala Leu Glu
    1250                1255

(2) INFORMATION FOR SEQ ID NO:2:
```

```
    (i) SEQUENCE CHARACTERISTICS:
        (A) LENGTH: 3774
        (B) TYPE: nucleic acid
        (C) STRANDEDNESS: single
        (D) TOPOLOGY: linear (ii) MOLECULE TYPE: nucleic acids (iii) HYPOTHETICAL: irrelevant (iv) ANTI-SENSE: no (vi) ORIGINAL SOURCE:
        (A) ORGANISM: Homo Sapiens
        (B) INDIVIDUAL ISOLATE: 17-18 week fetus (vii) IMMEDIATE SOURCE:
        (A) LIBRARY: Stratagene cDNA Library 936206
        (B) CLONE: synthesis of 4 clones (x) PUBLICATION INFORMATION:
        (A) AUTHORS: Hlavin, Mary Louise
                     Lemmon, Vance
        (B) TITLE: Molecular structure and functional testing of
            human L1CAM: an interspecies comparison.
        (C) JOURNAL: GENOMICS
        (D) VOLUME: 11
        (E) ISSUE:
        (F) PAGES: 416-423
        (G) DATE: 1991
        (K) RELEVANT RESIDUES IN SEQ ID NO: 1 to 3774

(xi) SEQUENCE DESCRIPTION: SEQ ID NO: 2:
```

```
ATG GTC GTG GCG CTG CGG TAC GTG TGG CCT CTC CTC CTC TGC AGC CCC        48
Met Val Val Ala Leu Arg Tyr Val Trp Pro Leu Leu Leu Cys Ser Pro
 1               5                  10                  15

TGC CTG CTT ATC CAG ATC CCC GAG GAA TAT GAA GGA CAC CAT GTG ATG        96
Cys Leu Leu Ile Gln Ile Pro Glu Glu Tyr Glu Gly His His Val Met
             20                  25                  30

GAG CCA CCT GTC ATC ACG GAA CAG TCT CCA CGG CGC CTG GTT GTC TTC       144
Glu Pro Pro Val Ile Thr Glu Gln Ser Pro Arg Arg Leu Val Val Phe
         35                  40                  45

CCC ACA GAT GAC ATC AGC CTC AAG TGT GAG GCC AGT GGC AAG CCC GAA       192
Pro Thr Asp Asp Ile Ser Leu Lys Cys Glu Ala Ser Gly Lys Pro Glu
     50                  55                  60

GTG CAG TTC CGC TGG ACG AGG GAT GGT GTC CAC TTC AAA CCC AAG GAA       240
Val Gln Phe Arg Trp Thr Arg Asp Gly Val His Phe Lys Pro Lys Glu
 65                  70                  75                  80

GAG CTG GGT GTG ACC GTG TAC CAG TCG CCC CAC TCT GGC TCC TTC ACC       288
Glu Leu Gly Val Thr Val Tyr Gln Ser Pro His Ser Gly Ser Phe Thr
                 85                  90                  95

ATC ACG GGC AAC AAC AGC AAC TTT GCT CAG AGG TTC CAG GGC ATC TAC       336
Ile Thr Gly Asn Asn Ser Asn Phe Ala Gln Arg Phe Gln Gly Ile Tyr
            100                 105                 110

CGC TGC TTT GCC AGC AAT AAG CTG GGC ACC GCC ATG TCC CAT GAG ATC       384
Arg Cys Phe Ala Ser Asn Lys Leu Gly Thr Ala Met Ser His Glu Ile
        115                 120                 125

CGG CTC ATG GCC GAG GGT GCC CCC AAG TGG CCA AAG GAG ACA GTG AAG       432
Arg Leu Met Ala Glu Gly Ala Pro Lys Trp Pro Lys Glu Thr Val Lys
    130                 135                 140

CCC GTG GAG GTG GAG GAA GGG GAG TCA GTG GTT CTG CCT TGC AAC CCT       480
Pro Val Glu Val Glu Glu Gly Glu Ser Val Val Leu Pro Cys Asn Pro
145                 150                 155                 160

CCC CCA AGT GCA GAG CCT CTC CGG ATC TAC TGG ATG AAC AGC AAG ATC       528
Pro Pro Ser Ala Glu Pro Leu Arg Ile Tyr Trp Met Asn Ser Lys Ile
                165                 170                 175

TTG CAC ATC AAG CAG GAC GAG CGG GTG ACG ATG GGC CAG AAC GGC AAC       576
```

```
Leu His Ile Lys Gln Asp Glu Arg Val Thr Met Gly Gln Asn Gly Asn
            180                 185                 190

CTC TAC TTT GCC AAT GTG CTC ACC TCC GAC AAC CAC TCA GAC TAC ATC      624
Leu Tyr Phe Ala Asn Val Leu Thr Ser Asp Asn His Ser Asp Tyr Ile
            195                 200                 205

TGC CAC GCC CAC TTC CCA GGC ACC AGG ACC ATC ATT CAG AAG GAA CCC      672
Cys His Ala His Phe Pro Gly Thr Arg Thr Ile Ile Gln Lys Glu Pro
    210                 215                 220

ATT GAC CTC CGG GTC AAG GCC ACC AAC AGC ATG ATT GAC AGG AAG CCG      720
Ile Asp Leu Arg Val Lys Ala Thr Asn Ser Met Ile Asp Arg Lys Pro
225                 230                 235                 240

CGC CTG CTC TTC CCC ACC AAC TCC AGC AGC CAC CTG GTG GCC TTG CAG      768
Arg Leu Leu Phe Pro Thr Asn Ser Ser Ser His Leu Val Ala Leu Gln
                245                 250                 255

GGG CAG CCA TTG GTC CTG GAG TGC ATC GCC GAG GGC TTT CCC ACG CCC      816
Gly Gln Pro Leu Val Leu Glu Cys Ile Ala Glu Gly Phe Pro Thr Pro
            260                 265                 270

ACC ATC AAA TGG CTG CGC CCC AGT GGC CCC ATG CCA GCT GAC CGT GTC      864
Thr Ile Lys Trp Leu Arg Pro Ser Gly Pro Met Pro Ala Asp Arg Val
            275                 280                 285

ACC TAC CAG AAC CAC AAC AAG ACC CTG CAG CTG CTG AAA GTG GGC GAG      912
Thr Tyr Gln Asn His Asn Lys Thr Leu Gln Leu Leu Lys Val Gly Glu
            290                 295                 300

GAG GAT GAT GGC GAG TAC CGC TGC CTG GCC GAG AAC TCA CTG GGC AGT      960
Glu Asp Asp Gly Glu Tyr Arg Cys Leu Ala Glu Asn Ser Leu Gly Ser
305                 310                 315                 320

GCC CGG CAT GCG TAC TAT GTC ACC GTG GAG GCT GCC CCG TAC TGG CTG     1008
Ala Arg His Ala Tyr Tyr Val Thr Val Glu Ala Ala Pro Tyr Trp Leu
                325                 330                 335

CAC AAG CCC CAG AGC CAT CTA TAT GGG CCA GGA GAG ACT GCC CGC CTG     1056
His Lys Pro Gln Ser His Leu Tyr Gly Pro Gly Glu Thr Ala Arg Leu
            340                 345                 350

GAC TGC CAA GTC CAG GGC AGG CCC CAA CCA GAG GTC ACC TGG AGA ATC     1104
Asp Cys Gln Val Gln Gly Arg Pro Gln Pro Glu Val Thr Trp Arg Ile
            355                 360                 365

AAC GGG ATC CCT GTG GAG GAG CTG GCC AAA GAC CAG AAG TAC CGG ATT     1152
Asn Gly Ile Pro Val Glu Glu Leu Ala Lys Asp Gln Lys Tyr Arg Ile
370                 375                 380

CAG CGT GGC GCC CTG ATC CTG AGC AAC GTG CAG CCC AGT GAC ACA ATG     1200
Gln Arg Gly Ala Leu Ile Leu Ser Asn Val Gln Pro Ser Asp Thr Met
385                 390                 395                 400

GTG ACC CAA TGT GAG GCC CGC AAC CGG CAC GGG CTC TTG CTG GCC AAT     1248
Val Thr Gln Cys Glu Ala Arg Asn Arg His Gly Leu Leu Leu Ala Asn
                405                 410                 415

GCC TAC ATC TAC GTT GTC CAG CTG CCA GCC AAG ATC CTG ACT GCG GAC     1296
Ala Tyr Ile Tyr Val Val Gln Leu Pro Ala Lys Ile Leu Thr Ala Asp
            420                 425                 430

AAT CAG ACG TAC ATG GCT GTC CAG GGC AGC ACT GCC TAC CTT CTG TGC     1344
Asn Gln Thr Tyr Met Ala Val Gln Gly Ser Thr Ala Tyr Leu Leu Cys
            435                 440                 445

AAG GCC TTC GGA GCG CCT GTG CCC AGT GTT CAG TGG CTG GAC GAG GAT     1392
Lys Ala Phe Gly Ala Pro Val Pro Ser Val Gln Trp Leu Asp Glu Asp
            450                 455                 460

GGG ACA ACA GTG CTT CAG GAC GAA CGC TTC TTC CCC TAT GCC AAT GGG     1440
Gly Thr Thr Val Leu Gln Asp Glu Arg Phe Phe Pro Tyr Ala Asn Gly
465                 470                 475                 480

ACC CTG GGC ATT CGA GAC CTC CAG GCC AAT GAC ACC GGA CGC TAC TTC     1488
Thr Leu Gly Ile Arg Asp Leu Gln Ala Asn Asp Thr Gly Arg Tyr Phe
                485                 490                 495

TGC CTG GCT GCC AAT GAC CAA AAC AAT GTT ACC ATC ATG GCT AAC CTG     1536
```

-continued

```
            Cys Leu Ala Ala Asn Asp Gln Asn Asn Val Thr Ile Met Ala Asn Leu
                    500                 505                 510

AAG GTT AAA GAT GCA ACT CAG ATC ACT CAG GGG CCC CGC AGC ACA ATC            1584
Lys Val Lys Asp Ala Thr Gln Ile Thr Gln Gly Pro Arg Ser Thr Ile
        515                 520                 525

GAG AAG AAA GGT TCC AGG GTG ACC TTC ACG TGC CAG GCC TCC TTT GAC            1632
Glu Lys Lys Gly Ser Arg Val Thr Phe Thr Cys Gln Ala Ser Phe Asp
530                 535                 540

CCC TCC TTG CAG CCC AGC ATC ACC TGG CGT GGG GAC GGT CGA GAC CTC            1680
Pro Ser Leu Gln Pro Ser Ile Thr Trp Arg Gly Asp Gly Arg Asp Leu
545                 550                 555                 560

CAG GAG CTT GGG GAC AGT GAC AAG TAC TTC ATA GAG GAT GGG CGC CTG            1728
Gln Glu Leu Gly Asp Ser Asp Lys Tyr Phe Ile Glu Asp Gly Arg Leu
                565                 570                 575

GTC ATC CAC AGC CTG GAC TAC AGC GAC CAG GGC AAC TAC AGC TGC GTG            1776
Val Ile His Ser Leu Asp Tyr Ser Asp Gln Gly Asn Tyr Ser Cys Val
            580                 585                 590

GCC AGT ACC GAA CTG GAT GTG GTG GAG AGT AGG GCA CAG CTC TTG GTG            1824
Ala Ser Thr Glu Leu Asp Val Val Glu Ser Arg Ala Gln Leu Leu Val
        595                 600                 605

GTG GGG AGC CCT GGG CCG GTG CCA CGG CTG GTG CTG TCC GAC CTG CAC            1872
Val Gly Ser Pro Gly Pro Val Pro Arg Leu Val Leu Ser Asp Leu His
610                 615                 620

CTG CTG ACG CAG AGC CAG GTG CGC GTG TCC TGG AGT CCT GCA GAA GAC            1920
Leu Leu Thr Gln Ser Gln Val Arg Val Ser Trp Ser Pro Ala Glu Asp
625                 630                 635                 640

CAC AAT GCC CCC ATT GAG AAA TAT GAC ATT GAA TTT GAG GAC AAG GAA            1968
His Asn Ala Pro Ile Glu Lys Tyr Asp Ile Glu Phe Glu Asp Lys Glu
                645                 650                 655

ATG GCG CCT GAA AAA TGG TAC AGT CTG GGC AAG GTT CCA GGG AAC CAG            2016
Met Ala Pro Glu Lys Trp Tyr Ser Leu Gly Lys Val Pro Gly Asn Gln
            660                 665                 670

ACC TCT ACC ACC CTC AAG CTG TCG CCC TAT GTC CAC TAC ACC TTT AGG            2064
Thr Ser Thr Thr Leu Lys Leu Ser Pro Tyr Val His Tyr Thr Phe Arg
        675                 680                 685

GTT ACT GCC ATA AAC AAA TAT GGC CCC GGG GAG CCC AGC CCG GTC TCT            2112
Val Thr Ala Ile Asn Lys Tyr Gly Pro Gly Glu Pro Ser Pro Val Ser
690                 695                 700

GAG ACT GTG GTC ACA CCT GAG GCA GCC CCA GAG AAG AAC CCT GTG GAT            2160
Glu Thr Val Val Thr Pro Glu Ala Ala Pro Glu Lys Asn Pro Val Asp
705                 710                 715                 720

GTG AAG GGG GAA GGA AAT GAG ACC ACC AAT ATG GTC ATC ACG TGG AAG            2208
Val Lys Gly Glu Gly Asn Glu Thr Thr Asn Met Val Ile Thr Trp Lys
                725                 730                 735

CCG CTC CGG TGG ATG GAC TGG AAC GCC CCC CAG GTT CAG TAC CGC GTG            2256
Pro Leu Arg Trp Met Asp Trp Asn Ala Pro Gln Val Gln Tyr Arg Val
            740                 745                 750

CAG TGG CGC CCT CAG GGG ACA CGA GGG CCC TGG CAG GAG CAG ATT GTC            2304
Gln Trp Arg Pro Gln Gly Thr Arg Gly Pro Trp Gln Glu Gln Ile Val
        755                 760                 765

AGC GAC CCC TTC CTG GTG GTG TCC AAC ACG TCC ACC TTC GTG CCC TAT            2352
Ser Asp Pro Phe Leu Val Val Ser Asn Thr Ser Thr Phe Val Pro Tyr
770                 775                 780

GAG ATC AAA GTC CAG GCC GTC AAC AGC CAG GGC AAG GGA CCA GAG CCC            2400
Glu Ile Lys Val Gln Ala Val Asn Ser Gln Gly Lys Gly Pro Glu Pro
785                 790                 795                 800

CAG GTC ACT ATC GGC TAC TCT GGA GAG GAC TAC CCC CAG GCA ATC CCT            2448
Gln Val Thr Ile Gly Tyr Ser Gly Glu Asp Tyr Pro Gln Ala Ile Pro
                805                 810                 815

GAG CTG GAA GGC ATT GAA ATC CTC AAC TCA AGT GCC GTG CTG GTC AAG            2496
```

-continued

```
                Glu Leu Glu Gly Ile Glu Ile Leu Asn Ser Ser Ala Val Leu Val Lys
                                820                 825                 830

TGG CGG CCG GTG GAC CTG GCC CAG GTC AAG GGC CAC CTC CGC GGA TAC      2544
Trp Arg Pro Val Asp Leu Ala Gln Val Lys Gly His Leu Arg Gly Tyr
            835                 840                 845

AAT GTG ACG TAC TGG AGG GAG GGC AGT CAG AGG AAG CAC AGC AAG AGA      2592
Asn Val Thr Tyr Trp Arg Glu Gly Ser Gln Arg Lys His Ser Lys Arg
850                 855                 860

CAT ATC CAC AAA GAC CAT GTG GTG GTG CCC GCC AAC ACC ACC AGT GTC      2640
His Ile His Lys Asp His Val Val Val Pro Ala Asn Thr Thr Ser Val
            865                 870                 875                 880

ATC CTC AGT GGC TTG CGG CCC TAT AGC TCC TAC CAC CTG GAG GTG CAG      2688
Ile Leu Ser Gly Leu Arg Pro Tyr Ser Ser Tyr His Leu Glu Val Gln
                    885                 890                 895

GCC TTT AAC GGG CGA GGA TCG GGG CCC GCC AGC GAG TTC ACC TTC AGC      2736
Ala Phe Asn Gly Arg Gly Ser Gly Pro Ala Ser Glu Phe Thr Phe Ser
                900                 905                 910

ACC CCA GAG GGA GTG CCT GGC CAC CCC GAG GCG TTG CAC CTG GAG TGC      2784
Thr Pro Glu Gly Val Pro Gly His Pro Glu Ala Leu His Leu Glu Cys
            915                 920                 925

CAG TCG AAC ACC AGC CTG CTG CTG CGC TGG CAG CCC CCA CTC AGC CAC      2832
Gln Ser Asn Thr Ser Leu Leu Leu Arg Trp Gln Pro Pro Leu Ser His
            930                 935                 940

AAC GGC GTG CTC ACC GGC TAC GTG CTC TCC TAC CAC CCC CTG GAT GAG      2880
Asn Gly Val Leu Thr Gly Tyr Val Leu Ser Tyr His Pro Leu Asp Glu
945                 950                 955                 960

GGG GGC AAG GGG CAA CTG TCC TTC AAC CTT CGG GAC CCC GAA CTT CGG      2928
Gly Gly Lys Gly Gln Leu Ser Phe Asn Leu Arg Asp Pro Glu Leu Arg
                    965                 970                 975

ACA CAC AAC CTG ACC GAT CTC AGC CCC CAC CTG CGG TAC CGC TTC CAG      2976
Thr His Asn Leu Thr Asp Leu Ser Pro His Leu Arg Tyr Arg Phe Gln
                980                 985                 990

CTT CAG GCC ACC ACC AAA GAG GGC CCT GGT GAA GCC ATC GTA CGG GAA      3024
Leu Gln Ala Thr Thr Lys Glu Gly Pro Gly Glu Ala Ile Val Arg Glu
            995                 1000                1005

GGA GGC ACT ATG GCC TTG TCT GGG ATC TCA GAT TTT GGC AAC ATC TCA      3072
Gly Gly Thr Met Ala Leu Ser Gly Ile Ser Asp Phe Gly Asn Ile Ser
        1010                1015                1020

GCC ACA GCG GGT GAA AAC TAC AGT GTC GTC TCC TGG GTC CCC AAG GAG      3120
Ala Thr Ala Gly Glu Asn Tyr Ser Val Val Ser Trp Val Pro Lys Glu
1025                1030                1035                1040

GGC CAG TGC AAC TTC AGG TTC CAT ATC TTG TTC AAA GCC TTG GGA GAA      3168
Gly Gln Cys Asn Phe Arg Phe His Ile Leu Phe Lys Ala Leu Gly Glu
                    1045                1050                1055

GAG AAG GGT GGG GCT TCC CTT TCG CCA CAG TAT GTC AGC TAC AAC CAG      3216
Glu Lys Gly Gly Ala Ser Leu Ser Pro Gln Tyr Val Ser Tyr Asn Gln
                1060                1065                1070

AGC TCC TAC ACG CAG TGG GAC CTG CAG CCT GAC ACT GAC TAC GAG ATC      3264
Ser Ser Tyr Thr Gln Trp Asp Leu Gln Pro Asp Thr Asp Tyr Glu Ile
            1075                1080                1085

CAC TTG TTT AAG GAG AGG ATG TTC CGG CAC CAA ATG GCT GTG AAG ACC      3312
His Leu Phe Lys Glu Arg Met Phe Arg His Gln Met Ala Val Lys Thr
        1090                1095                1100

AAT GGC ACA GGC CGC GTG AGG CTC CCT CCT GCT GGC TTC GCC ACT GAG      3360
Asn Gly Thr Gly Arg Val Arg Leu Pro Pro Ala Gly Phe Ala Thr Glu
1105                1110                1115                1120

GGC TGG TTC ATC GGC TTT GTG AGT GCC ATC ATC CTC CTC CTC CTC GTC      3408
Gly Trp Phe Ile Gly Phe Val Ser Ala Ile Ile Leu Leu Leu Leu Val
                    1125                1130                1135

CTG CTC ATC CTC TGC TTC ATC AAG CGC AGC AAG GGC GGC AAA TAC TCA      3456
```

```
                                                           -continued

Leu Leu Ile Leu Cys Phe Ile Lys Arg Ser Lys Gly Gly Lys Tyr Ser
            1140                1145                1150

GTG AAG GAT AAG GAG GAC ACC CAG GTG GAC TCT GAG GCC CGA CCG ATG         3504
Val Lys Asp Lys Glu Asp Thr Gln Val Asp Ser Glu Ala Arg Pro Met
            1155                1160                1165

AAA GAT GAG ACC TTC GGC GAG TAC AGG TCC CTG GAG AGT GAC AAC GAG         3552
Lys Asp Glu Thr Phe Gly Glu Tyr Arg Ser Leu Glu Ser Asp Asn Glu
        1170                1175                1180

GAG AAG GCC TTT GGC AGC AGC CAG CCA TCG CTC AAC GGG GAC ATC AAG         3600
Glu Lys Ala Phe Gly Ser Ser Gln Pro Ser Leu Asn Gly Asp Ile Lys
1185                1190                1195                1200

CCC CTG GGC AGT GAC GAC AGC CTG GCC GAT TAT GGG GGC AGC GTG GAT         3648
Pro Leu Gly Ser Asp Asp Ser Leu Ala Asp Tyr Gly Gly Ser Val Asp
            1205                1210                1215

GTT CAG TTC AAC GAG GAT GGT TCG TTC ATT GGC CAG TAC AGT GGC AAG         3696
Val Gln Phe Asn Glu Asp Gly Ser Phe Ile Gly Gln Tyr Ser Gly Lys
            1220                1225                1230

AAG GAG AAG GAG GCG GCA GGG GGC AAT GAC AGC TCA GGG GCC ACT TCC         3744
Lys Glu Lys Glu Ala Ala Gly Gly Asn Asp Ser Ser Gly Ala Thr Ser
            1235                1240                1245

CCC ATC AAC CCT GCC GTG GCC CTA GAA TAG                                 3774
Pro Ile Asn Pro Ala Val Ala Leu Glu stop
        1250                1255

(2) INFORMATION FOR SEQ ID NO:3:

(i) SEQUENCE CHARACTERISTICS:
        (A) LENGTH: 3189
        (B) TYPE: nucleic acid
        (C) STRANDEDNESS: single
        (D) TOPOLOGY:   linear (ii) MOLECULE TYPE: nucleic acids (iii) HYPOTHETICAL:    irrelevant (iv) ANTI-SENSE: no (vi) ORIGINAL SOURCE:
        (A) ORGANISM: homo sapiens
        (B) INDIVIDUAL ISOLATE: 17-18 week fetus (vii) IMMEDIATE SOURCE:
        (A) LIBRARY: Stratagene cDNA Library 936206
        (B) CLONE: 3.1

(x) PUBLICATION INFORMATION:
        (A) AUTHORS:   Hlavin, Mary Louise
            Lemmon, Vance
        (B) TITLE:     Molecular structure and functional testing of
            human L1CAM: an interspecies comparison.
        (C) JOURNAL:   GENOMICS
        (D) VOLUME:    11
        (E) ISSUE:
        (F) PAGES:     416-423
        (G) DATE:      1991
        (K) RELEVANT RESIDUES IN SEQ ID NO:  548 to 3736

(xi) SEQUENCE DESCRIPTION: SEQ ID NO: 3:

AG CGG GTG ACG ATG GGC CAG AAC GGC AAC CTC TAC TTT GCC AAT GTG           47
   Arg Val Thr Met Gly Gln Asn Gly Asn Leu Tyr Phe Ala Asn Val
    1               5                   10                  15

CTC ACC TCC GAC AAC CAC TCA GAC TAC ATC TGC CAC GCC CAC TTC CCA          95
Leu Thr Ser Asp Asn His Ser Asp Tyr Ile Cys His Ala His Phe Pro
            20                  25                  30

GGC ACC AGG ACC ATC ATT CAG AAG GAA CCC ATT GAC CTC CGG GTC AAG         143
Gly Thr Arg Thr Ile Ile Gln Lys Glu Pro Ile Asp Leu Arg Val Lys
        35                  40                  45

GCC ACC AAC AGC ATG ATT GAC AGG AAG CCG CGC CTG CTC TTC CCC ACC         191
```

-continued

| | | | | | | | | | | | | |
|---|---|---|---|---|---|---|---|---|---|---|---|---|
| Ala | Thr | Asn | Ser | Met | Ile | Asp | Arg | Lys | Pro | Arg | Leu | Leu Phe Pro Thr |
| | | 50 | | | | 55 | | | | 60 | | |

```
AAC TCC AGC AGC CAC CTG GTG GCC TTG CAG GGG CAG CCA TTG GTC CTG      239
Asn Ser Ser Ser His Leu Val Ala Leu Gln Gly Gln Pro Leu Val Leu
         65                  70                  75

GAG TGC ATC GCC GAG GGC TTT CCC ACG CCC ACC ATC AAA TGG CTG CGC      287
Glu Cys Ile Ala Glu Gly Phe Pro Thr Pro Thr Ile Lys Trp Leu Arg
 80                  85                  90                  95

CCC AGT GGC CCC ATG CCA GCT GAC CGT GTC ACC TAC CAG AAC CAC AAC      335
Pro Ser Gly Pro Met Pro Ala Asp Arg Val Thr Tyr Gln Asn His Asn
                100                 105                 110

AAG ACC CTG CAG CTG CTG AAA GTG GGC GAG GAG GAT GAT GGC GAG TAC      383
Lys Thr Leu Gln Leu Leu Lys Val Gly Glu Glu Asp Asp Gly Glu Tyr
            115                 120                 125

CGC TGC CTG GCC GAG AAC TCA CTG GGC AGT GCC CGG CAT GCG TAC TAT      431
Arg Cys Leu Ala Glu Asn Ser Leu Gly Ser Ala Arg His Ala Tyr Tyr
        130                 135                 140

GTC ACC GTG GAG GCT GCC CCG TAC TGG CTG CAC AAG CCC CAG AGC CAT      479
Val Thr Val Glu Ala Ala Pro Tyr Trp Leu His Lys Pro Gln Ser His
    145                 150                 155

CTA TAT GGG CCA GGA GAG ACT GCC CGC CTG GAC TGC CAA GTC CAG GGC      527
Leu Tyr Gly Pro Gly Glu Thr Ala Arg Leu Asp Cys Gln Val Gln Gly
160                 165                 170                 175

AGG CCC CAA CCA GAG GTC ACC TGG AGA ATC AAC GGG ATC CCT GTG GAG      575
Arg Pro Gln Pro Glu Val Thr Trp Arg Ile Asn Gly Ile Pro Val Glu
                180                 185                 190

GAG CTG GCC AAA GAC CAG AAG TAC CGG ATT CAG CGT GGC GCC CTG ATC      623
Glu Leu Ala Lys Asp Gln Lys Tyr Arg Ile Gln Arg Gly Ala Leu Ile
            195                 200                 205

CTG AGC AAC GTG CAG CCC AGT GAC ACA ATG GTG ACC CAA TGT GAG GCC      671
Leu Ser Asn Val Gln Pro Ser Asp Thr Met Val Thr Gln Cys Glu Ala
        210                 215                 220

CGC AAC CGG CAC GGG CTC TTG CTG GCC AAT GCC TAC ATC TAC GTT GTC      719
Arg Asn Arg His Gly Leu Leu Leu Ala Asn Ala Tyr Ile Tyr Val Val
    225                 230                 235

CAG CTG CCA GCC AAG ATC CTG ACT GCG GAC AAT CAG ACG TAC ATG GCT      767
Gln Leu Pro Ala Lys Ile Leu Thr Ala Asp Asn Gln Thr Tyr Met Ala
240                 245                 250                 255

GTC CAG GGC AGC ACT GCC TAC CTT CTG TGC AAG GCC TTC GGA GCG CCT      815
Val Gln Gly Ser Thr Ala Tyr Leu Leu Cys Lys Ala Phe Gly Ala Pro
                260                 265                 270

GTG CCC AGT GTT CAG TGG CTG GAC GAG GAT GGG ACA ACA GTG CTT CAG      863
Val Pro Ser Val Gln Trp Leu Asp Glu Asp Gly Thr Thr Val Leu Gln
            275                 280                 285

GAC GAA CGC TTC TTC CCC TAT GCC AAT GGG ACC CTG GGC ATT CGA GAC      911
Asp Glu Arg Phe Phe Pro Tyr Ala Asn Gly Thr Leu Gly Ile Arg Asp
        290                 295                 300

CTC CAG GCC AAT GAC ACC GGA CGC TAC TTC TGC CTG GCT GCC AAT GAC      959
Leu Gln Ala Asn Asp Thr Gly Arg Tyr Phe Cys Leu Ala Ala Asn Asp
    305                 310                 315

CAA AAC AAT GTT ACC ATC ATG GCT AAC CTG AAG GTT AAA GAT GCA ACT     1007
Gln Asn Asn Val Thr Ile Met Ala Asn Leu Lys Val Lys Asp Ala Thr
320                 325                 330                 335

CAG ATC ACT CAG GGG CCC CGC AGC ACA ATC GAG AAG AAA GGT TCC AGG     1055
Gln Ile Thr Gln Gly Pro Arg Ser Thr Ile Glu Lys Lys Gly Ser Arg
                340                 345                 350

GTG ACC TTC ACG TGC CAG GCC TCC TTT GAC CCC TCC TTG CAG CCC AGC     1103
Val Thr Phe Thr Cys Gln Ala Ser Phe Asp Pro Ser Leu Gln Pro Ser
            355                 360                 365

ATC ACC TGG CGT GGG GAC GGT CGA GAC CTC CAG GAG CTT GGG GAC AGT     1151
```

-continued

| | | | | | | | | | | | | | | |
|---|---|---|---|---|---|---|---|---|---|---|---|---|---|---|
| Ile | Thr | Trp | Arg | Gly | Asp | Gly | Arg | Asp | Leu | Gln | Glu | Leu | Gly | Asp | Ser |
| | | 370 | | | | 375 | | | | 380 | | | | | |

```
GAC AAG TAC TTC ATA GAG GAT GGG CGC CTG GTC ATC CAC AGC CTG GAC          1199
Asp Lys Tyr Phe Ile Glu Asp Gly Arg Leu Val Ile His Ser Leu Asp
    385                 390                 395

TAC AGC GAC CAG GGC AAC TAC AGC TGC GTG GCC AGT ACC GAA CTG GAT          1247
Tyr Ser Asp Gln Gly Asn Tyr Ser Cys Val Ala Ser Thr Glu Leu Asp
400                 405                 410                 415

GTG GTG GAG AGT AGG GCA CAG CTC TTG GTG GTG GGG AGC CCT GGG CCG          1295
Val Val Glu Ser Arg Ala Gln Leu Leu Val Val Gly Ser Pro Gly Pro
                420                 425                 430

GTG CCA CGG CTG GTG CTG TCC GAC CTG CAC CTG CTG ACG CAG AGC CAG          1343
Val Pro Arg Leu Val Leu Ser Asp Leu His Leu Leu Thr Gln Ser Gln
        435                 440                 445

GTG CGC GTG TCC TGG AGT CCT GCA GAA GAC CAC AAT GCC CCC ATT GAG          1391
Val Arg Val Ser Trp Ser Pro Ala Glu Asp His Asn Ala Pro Ile Glu
    450                 455                 460

AAA TAT GAC ATT GAA TTT GAG GAC AAG GAA ATG GCG CCT GAA AAA TGG          1439
Lys Tyr Asp Ile Glu Phe Glu Asp Lys Glu Met Ala Pro Glu Lys Trp
465                 470                 475

TAC AGT CTG GGC AAG GTT CCA GGG AAC CAG ACC TCT ACC ACC CTC AAG          1487
Tyr Ser Leu Gly Lys Val Pro Gly Asn Gln Thr Ser Thr Thr Leu Lys
480                 485                 490                 495

CTG TCG CCC TAT GTC CAC TAC ACC TTT AGG GTT ACT GCC ATA AAC AAA          1535
Leu Ser Pro Tyr Val His Tyr Thr Phe Arg Val Thr Ala Ile Asn Lys
                500                 505                 510

TAT GGC CCC GGG GAG CCC AGC CCG GTC TCT GAG ACT GTG GTC ACA CCT          1583
Tyr Gly Pro Gly Glu Pro Ser Pro Val Ser Glu Thr Val Val Thr Pro
        515                 520                 525

GAG GCA GCC CCA GAG AAG AAC CCT GTG GAT GTG AAG GGG GAA GGA AAT          1631
Glu Ala Ala Pro Glu Lys Asn Pro Val Asp Val Lys Gly Glu Gly Asn
    530                 535                 540

GAG ACC ACC AAT ATG GTC ATC ACG TGG AAG CCG CTC CGG TGG ATG GAC          1679
Glu Thr Thr Asn Met Val Ile Thr Trp Lys Pro Leu Arg Trp Met Asp
545                 550                 555

TGG AAC GCC CCC CAG GTT CAG TAC CGC GTG CAG TGG CGC CCT CAG GGG          1727
Trp Asn Ala Pro Gln Val Gln Tyr Arg Val Gln Trp Arg Pro Gln Gly
560                 565                 570                 575

ACA CGA GGG CCC TGG CAG GAG CAG ATT GTC AGC GAC CCC TTC CTG GTG          1775
Thr Arg Gly Pro Trp Gln Glu Gln Ile Val Ser Asp Pro Phe Leu Val
                580                 585                 590

GTG TCC AAC ACG TCC ACC TTC GTG CCC TAT GAG ATC AAA GTC CAG GCC          1823
Val Ser Asn Thr Ser Thr Phe Val Pro Tyr Glu Ile Lys Val Gln Ala
        595                 600                 605

GTC AAC AGC CAG GGC AAG GGA CCA GAG CCC CAG GTC ACT ATC GGC TAC          1871
Val Asn Ser Gln Gly Lys Gly Pro Glu Pro Gln Val Thr Ile Gly Tyr
    610                 615                 620

TCT GGA GAG GAC TAC CCC CAG GCA ATC CCT GAG CTG GAA GGC ATT GAA          1919
Ser Gly Glu Asp Tyr Pro Gln Ala Ile Pro Glu Leu Glu Gly Ile Glu
625                 630                 635

ATC CTC AAC TCA AGT GCC GTG CTG GTC AAG TGG CGG CCG GTG GAC CTG          1967
Ile Leu Asn Ser Ser Ala Val Leu Val Lys Trp Arg Pro Val Asp Leu
640                 645                 650                 655

GCC CAG GTC AAG GGC CAC CTC CGC GGA TAC AAT GTG ACG TAC TGG AGG          2015
Ala Gln Val Lys Gly His Leu Arg Gly Tyr Asn Val Thr Tyr Trp Arg
                660                 665                 670

GAG GGC AGT CAG AGG AAG CAC AGC AAG AGA CAT ATC CAC AAA GAC CAT          2063
Glu Gly Ser Gln Arg Lys His Ser Lys Arg His Ile His Lys Asp His
        675                 680                 685

GTG GTG GTG CCC GCC AAC ACC ACC AGT GTC ATC CTC AGT GGC TTG CGG          2111
```

| | | | | | | | | | | | | | | | |
|---|---|---|---|---|---|---|---|---|---|---|---|---|---|---|---|
|Val|Val|Val|Pro|Ala|Asn|Thr|Thr|Ser|Val|Ile|Leu|Ser|Gly|Leu|Arg|
| |690| | | |695| | | |700| | | | | | |

| | | | | | | | | | | | | | | | |
|---|---|---|---|---|---|---|---|---|---|---|---|---|---|---|---|
|CCC|TAT|AGC|TCC|TAC|CAC|CTG|GAG|GTG|CAG|GCC|TTT|AAC|GGG|CGA|GGA|2159|
|Pro|Tyr|Ser|Ser|Tyr|His|Leu|Glu|Val|Gln|Ala|Phe|Asn|Gly|Arg|Gly|
| |705| | | |710| | | |715| | | | | | |

| | | | | | | | | | | | | | | | |
|---|---|---|---|---|---|---|---|---|---|---|---|---|---|---|---|
|TCG|GGG|CCC|GCC|AGC|GAG|TTC|ACC|TTC|AGC|ACC|CCA|GAG|GGA|GTG|CCT|2207|
|Ser|Gly|Pro|Ala|Ser|Glu|Phe|Thr|Phe|Ser|Thr|Pro|Glu|Gly|Val|Pro|
|720| | | |725| | | |730| | | | | | |735|

| | | | | | | | | | | | | | | | |
|---|---|---|---|---|---|---|---|---|---|---|---|---|---|---|---|
|GGC|CAC|CCC|GAG|GCG|TTG|CAC|CTG|GAG|TGC|CAG|TCG|AAC|ACC|AGC|CTG|2255|
|Gly|His|Pro|Glu|Ala|Leu|His|Leu|Glu|Cys|Gln|Ser|Asn|Thr|Ser|Leu|
| | | |740| | | | |745| | | | |750| | |

| | | | | | | | | | | | | | | | |
|---|---|---|---|---|---|---|---|---|---|---|---|---|---|---|---|
|CTG|CTG|CGC|TGG|CAG|CCC|CCA|CTC|AGC|CAC|AAC|GGC|GTG|CTC|ACC|GGC|2303|
|Leu|Leu|Arg|Trp|Gln|Pro|Pro|Leu|Ser|His|Asn|Gly|Val|Leu|Thr|Gly|
| | | | |755| | | | |760| | | | |765| |

| | | | | | | | | | | | | | | | |
|---|---|---|---|---|---|---|---|---|---|---|---|---|---|---|---|
|TAC|GTG|CTC|TCC|TAC|CAC|CCC|CTG|GAT|GAG|GGG|GGC|AAG|GGG|CAA|CTG|2351|
|Tyr|Val|Leu|Ser|Tyr|His|Pro|Leu|Asp|Glu|Gly|Gly|Lys|Gly|Gln|Leu|
| | |770| | | | |775| | | | |780| | | |

| | | | | | | | | | | | | | | | |
|---|---|---|---|---|---|---|---|---|---|---|---|---|---|---|---|
|TCC|TTC|AAC|CTT|CGG|GAC|CCC|GAA|CTT|CGG|ACA|CAC|AAC|CTG|ACC|GAT|2399|
|Ser|Phe|Asn|Leu|Arg|Asp|Pro|Glu|Leu|Arg|Thr|His|Asn|Leu|Thr|Asp|
| |785| | | | |790| | | | |795| | | | |

| | | | | | | | | | | | | | | | |
|---|---|---|---|---|---|---|---|---|---|---|---|---|---|---|---|
|CTC|AGC|CCC|CAC|CTG|CGG|TAC|CGC|TTC|CAG|CTT|CAG|GCC|ACC|ACC|AAA|2447|
|Leu|Ser|Pro|His|Leu|Arg|Tyr|Arg|Phe|Gln|Leu|Gln|Ala|Thr|Thr|Lys|
|800| | | |805| | | | |810| | | | |815| |

| | | | | | | | | | | | | | | | |
|---|---|---|---|---|---|---|---|---|---|---|---|---|---|---|---|
|GAG|GGC|CCT|GGT|GAA|GCC|ATC|GTA|CGG|GAA|GGA|GGC|ACT|ATG|GCC|TTG|2495|
|Glu|Gly|Pro|Gly|Glu|Ala|Ile|Val|Arg|Glu|Gly|Gly|Thr|Met|Ala|Leu|
| | | | |820| | | | |825| | | | |830| |

| | | | | | | | | | | | | | | | |
|---|---|---|---|---|---|---|---|---|---|---|---|---|---|---|---|
|TCT|GGG|ATC|TCA|GAT|TTT|GGC|AAC|ATC|TCA|GCC|ACA|GCG|GGT|GAA|AAC|2543|
|Ser|Gly|Ile|Ser|Asp|Phe|Gly|Asn|Ile|Ser|Ala|Thr|Ala|Gly|Glu|Asn|
| | |835| | | | |840| | | | |845| | | |

| | | | | | | | | | | | | | | | |
|---|---|---|---|---|---|---|---|---|---|---|---|---|---|---|---|
|TAC|AGT|GTC|GTC|TCC|TGG|GTC|CCC|AAG|GAG|GGC|CAG|TGC|AAC|TTC|AGG|2591|
|Tyr|Ser|Val|Val|Ser|Trp|Val|Pro|Lys|Glu|Gly|Gln|Cys|Asn|Phe|Arg|
| |850| | | | |855| | | | |860| | | | |

| | | | | | | | | | | | | | | | |
|---|---|---|---|---|---|---|---|---|---|---|---|---|---|---|---|
|TTC|CAT|ATC|TTG|TTC|AAA|GCC|TTG|GGA|GAA|GAG|AAG|GGT|GGG|GCT|TCC|2639|
|Phe|His|Ile|Leu|Phe|Lys|Ala|Leu|Gly|Glu|Glu|Lys|Gly|Gly|Ala|Ser|
|865| | | |870| | | | |875| | | | | | |

| | | | | | | | | | | | | | | | |
|---|---|---|---|---|---|---|---|---|---|---|---|---|---|---|---|
|CTT|TCG|CCA|CAG|TAT|GTC|AGC|TAC|AAC|CAG|AGC|TCC|TAC|ACG|CAG|TGG|2687|
|Leu|Ser|Pro|Gln|Tyr|Val|Ser|Tyr|Asn|Gln|Ser|Ser|Tyr|Thr|Gln|Trp|
|880| | | |885| | | | |890| | | | |895| |

| | | | | | | | | | | | | | | | |
|---|---|---|---|---|---|---|---|---|---|---|---|---|---|---|---|
|GAC|CTG|CAG|CCT|GAC|ACT|GAC|TAC|GAG|ATC|CAC|TTG|TTT|AAG|GAG|AGG|2735|
|Asp|Leu|Gln|Pro|Asp|Thr|Asp|Tyr|Glu|Ile|His|Leu|Phe|Lys|Glu|Arg|
| | | |900| | | | |905| | | | |910| | |

| | | | | | | | | | | | | | | | |
|---|---|---|---|---|---|---|---|---|---|---|---|---|---|---|---|
|ATG|TTC|CGG|CAC|CAA|ATG|GCT|GTG|AAG|ACC|AAT|GGC|ACA|GGC|CGC|GTG|2783|
|Met|Phe|Arg|His|Gln|Met|Ala|Val|Lys|Thr|Asn|Gly|Thr|Gly|Arg|Val|
| | |915| | | | |920| | | | |925| | | |

| | | | | | | | | | | | | | | | |
|---|---|---|---|---|---|---|---|---|---|---|---|---|---|---|---|
|AGG|CTC|CCT|CCT|GCT|GGC|TTC|GCC|ACT|GAG|GGC|TGG|TTC|ATC|GGC|TTT|2831|
|Arg|Leu|Pro|Pro|Ala|Gly|Phe|Ala|Thr|Glu|Gly|Trp|Phe|Ile|Gly|Phe|
| |930| | | | |935| | | | |940| | | | |

| | | | | | | | | | | | | | | | |
|---|---|---|---|---|---|---|---|---|---|---|---|---|---|---|---|
|GTG|AGT|GCC|ATC|ATC|CTC|CTG|CTC|CTC|GTC|CTG|CTC|ATC|CTC|TGC|TTC|2879|
|Val|Ser|Ala|Ile|Ile|Leu|Leu|Leu|Leu|Val|Leu|Leu|Ile|Leu|Cys|Phe|
| |945| | | | |950| | | | |955| | | | |

| | | | | | | | | | | | | | | | |
|---|---|---|---|---|---|---|---|---|---|---|---|---|---|---|---|
|ATC|AAG|CGC|AGC|AAG|GGC|GGC|AAA|TAC|TCA|GTG|AAG|GAT|AAG|GAG|GAC|2927|
|Ile|Lys|Arg|Ser|Lys|Gly|Gly|Lys|Tyr|Ser|Val|Lys|Asp|Lys|Glu|Asp|
|960| | | |965| | | | |970| | | | |975| |

| | | | | | | | | | | | | | | | |
|---|---|---|---|---|---|---|---|---|---|---|---|---|---|---|---|
|ACC|CAG|GTG|GAC|TCT|GAG|GCC|CGA|CCG|ATG|AAA|GAT|GAG|ACC|TTC|GGC|2975|
|Thr|Gln|Val|Asp|Ser|Glu|Ala|Arg|Pro|Met|Lys|Asp|Glu|Thr|Phe|Gly|
| | | |980| | | | |985| | | | |990| | |

| | | | | | | | | | | | | | | | |
|---|---|---|---|---|---|---|---|---|---|---|---|---|---|---|---|
|GAG|TAC|AGG|TCC|CTG|GAG|AGT|GAC|AAC|GAG|GAG|AAG|GCC|TTT|GGC|AGC|3023|
|Glu|Tyr|Arg|Ser|Leu|Glu|Ser|Asp|Asn|Glu|Glu|Lys|Ala|Phe|Gly|Ser|
| | |995| | | | |1000| | | | |1005| | | |

| | | | | | | | | | | | | | | | |
|---|---|---|---|---|---|---|---|---|---|---|---|---|---|---|---|
|AGC|CAG|CCA|TCG|CTC|AAC|GGG|GAC|ATC|AAG|CCC|CTG|GGC|AGT|GAC|GAC|3071|

```
         Ser Gln Pro Ser Leu Asn Gly Asp Ile Lys Pro Leu Gly Ser Asp Asp
                 1010                1015                1020

AGC CTG GCC GAT TAT GGG GGC AGC GTG GAT GTT CAG TTC AAC GAG GAT           3119
Ser Leu Ala Asp Tyr Gly Gly Ser Val Asp Val Gln Phe Asn Glu Asp
         1025                1030                1035

GGT TCG TTC ATT GGC CAG TAC AGT GGC AAG AAG GAG AAG GAG GCG GCA           3167
Gly Ser Phe Ile Gly Gln Tyr Ser Gly Lys Lys Glu Lys Glu Ala Ala
1040                1045                1050                1055

GGG GGC AAT GAC AGC TCA GGG G                                             3189
Gly Gly Asn Asp Ser Ser Gly
                1060
```

(2) INFORMATION FOR SEQ ID NO:4:

(i) SEQUENCE CHARACTERISTICS:
        (A) LENGTH: 2600
        (B) TYPE: nucleic acid
        (C) STRANDEDNESS: single
        (D) TOPOLOGY: linear (ii) MOLECULE TYPE: nucleic acids (iii) HYPOTHETICAL: irrelevant (iv) ANTI-SENSE: no (vi) ORIGINAL SOURCE:
        (A) ORGANISM: homo sapiens
        (B) INDIVIDUAL ISOLATE: 17-18 week fetus (vii) IMMEDIATE SOURCE:
        (A) LIBRARY: Stratagene cDNA Library 936206
        (B) CLONE: 4

(x) PUBLICATION INFORMATION:
        (A) AUTHORS: Hlavin, Mary Louise
            Lemmon, Vance
        (B) TITLE: Molecular structure and functional testing of human L1CAM: an interspecies comparison.
        (C) JOURNAL: GENOMICS
        (D) VOLUME: 11
        (E) ISSUE:
        (F) PAGES: 416-423
        (G) DATE: 1991
        (K) RELEVANT RESIDUES IN SEQ ID NO: 1108 to 3708

(xi) SEQUENCE DESCRIPTION: SEQ ID NO: 4:

```
GGG ATC CCT GTG GAG GAG CTG GCC AAA GAC CAG AAG TAC CGG ATT CAG            48
Gly Ile Pro Val Glu Glu Leu Ala Lys Asp Gln Lys Tyr Arg Ile Gln
 1               5                  10                  15

CGT GGC GCC CTG ATC CTG AGC AAC GTG CAG CCC AGT GAC ACA ATG GTG            96
Arg Gly Ala Leu Ile Leu Ser Asn Val Gln Pro Ser Asp Thr Met Val
                 20                  25                  30

ACC CAA TGT GAG GCC CGC AAC CGG CAC GGG CTC TTG CTG GCC AAT GCC           144
Thr Gln Cys Glu Ala Arg Asn Arg His Gly Leu Leu Leu Ala Asn Ala
         35                  40                  45

TAC ATC TAC GTT GTC CAG CTG CCA GCC AAG ATC CTG ACT GCG GAC AAT           192
Tyr Ile Tyr Val Val Gln Leu Pro Ala Lys Ile Leu Thr Ala Asp Asn
     50                  55                  60

CAG ACG TAC ATG GCT GTC CAG GGC AGC ACT GCC TAC CTT CTG TGC AAG           240
Gln Thr Tyr Met Ala Val Gln Gly Ser Thr Ala Tyr Leu Leu Cys Lys
 65                  70                  75                  80

GCC TTC GGA GCG CCT GTG CCC AGT GTT CAG TGG CTG GAC GAG GAT GGG           288
Ala Phe Gly Ala Pro Val Pro Ser Val Gln Trp Leu Asp Glu Asp Gly
                 85                  90                  95

ACA ACA GTG CTT CAG GAC GAA CGC TTC TTC CCC TAT GCC AAT GGG ACC           336
Thr Thr Val Leu Gln Asp Glu Arg Phe Phe Pro Tyr Ala Asn Gly Thr
                100                 105                 110

CTG GGC ATT CGA GAC CTC CAG GCC AAT GAC ACC GGA CGC TAC TTC TGC           384
```

-continued

```
                Leu Gly Ile Arg Asp Leu Gln Ala Asn Asp Thr Gly Arg Tyr Phe Cys
                            115                 120                 125

CTG GCT GCC AAT GAC CAA AAC AAT GTT ACC ATC ATG GCT AAC CTG AAG        432
Leu Ala Ala Asn Asp Gln Asn Asn Val Thr Ile Met Ala Asn Leu Lys
        130                 135                 140

GTT AAA GAT GCA ACT CAG ATC ACT CAG GGG CCC CGC AGC ACA ATC GAG        480
Val Lys Asp Ala Thr Gln Ile Thr Gln Gly Pro Arg Ser Thr Ile Glu
145                 150                 155                 160

AAG AAA GGT TCC AGG GTG ACC TTC ACG TGC CAG GCC TCC TTT GAC CCC        528
Lys Lys Gly Ser Arg Val Thr Phe Thr Cys Gln Ala Ser Phe Asp Pro
                165                 170                 175

TCC TTG CAG CCC AGC ATC ACC TGG CGT GGG GAC GGT CGA GAC CTC CAG        576
Ser Leu Gln Pro Ser Ile Thr Trp Arg Gly Asp Gly Arg Asp Leu Gln
            180                 185                 190

GAG CTT GGG GAC AGT GAC AAG TAC TTC ATA GAG GAT GGG CGC CTG GTC        624
Glu Leu Gly Asp Ser Asp Lys Tyr Phe Ile Glu Asp Gly Arg Leu Val
        195                 200                 205

ATC CAC AGC CTG GAC TAC AGC GAC CAG GGC AAC TAC AGC TGC GTG GCC        672
Ile His Ser Leu Asp Tyr Ser Asp Gln Gly Asn Tyr Ser Cys Val Ala
    210                 215                 220

AGT ACC GAA CTG GAT GTG GTG GAG AGT AGG GCA CAG CTC TTG GTG GTG        720
Ser Thr Glu Leu Asp Val Val Glu Ser Arg Ala Gln Leu Leu Val Val
225                 230                 235                 240

GGG AGC CCT GGG CCG GTG CCA CGG CTG GTG CTG TCC GAC CTG CAC CTG        768
Gly Ser Pro Gly Pro Val Pro Arg Leu Val Leu Ser Asp Leu His Leu
                245                 250                 255

CTG ACG CAG AGC CAG GTG CGC GTG TCC TGG AGT CCT GCA GAA GAC CAC        816
Leu Thr Gln Ser Gln Val Arg Val Ser Trp Ser Pro Ala Glu Asp His
            260                 265                 270

AAT GCC CCC ATT GAG AAA TAT GAC ATT GAA TTT GAG GAC AAG GAA ATG        864
Asn Ala Pro Ile Glu Lys Tyr Asp Ile Glu Phe Glu Asp Lys Glu Met
        275                 280                 285

GCG CCT GAA AAA TGG TAC AGT CTG GGC AAG GTT CCA GGG AAC CAG ACC        912
Ala Pro Glu Lys Trp Tyr Ser Leu Gly Lys Val Pro Gly Asn Gln Thr
    290                 295                 300

TCT ACC ACC CTC AAG CTG TCG CCC TAT GTC CAC TAC ACC TTT AGG GTT        960
Ser Thr Thr Leu Lys Leu Ser Pro Tyr Val His Tyr Thr Phe Arg Val
305                 310                 315                 320

ACT GCC ATA AAC AAA TAT GGC CCC GGG GAG CCC AGC CCG GTC TCT GAG       1008
Thr Ala Ile Asn Lys Tyr Gly Pro Gly Glu Pro Ser Pro Val Ser Glu
                325                 330                 335

ACT GTG GTC ACA CCT GAG GCA GCC CCA GAG AAG AAC CCT GTG GAT GTG       1056
Thr Val Val Thr Pro Glu Ala Ala Pro Glu Lys Asn Pro Val Asp Val
            340                 345                 350

AAG GGG GAA GGA AAT GAG ACC ACC AAT ATG GTC ATC ACG TGG AAG CCG       1104
Lys Gly Glu Gly Asn Glu Thr Thr Asn Met Val Ile Thr Trp Lys Pro
        355                 360                 365

CTC CGG TGG ATG GAC TGG AAC GCC CCC CAG GTT CAG TAC CGC GTG CAG       1152
Leu Arg Trp Met Asp Trp Asn Ala Pro Gln Val Gln Tyr Arg Val Gln
    370                 375                 380

TGG CGC CCT CAG GGG ACA CGA GGG CCC TGG CAG GAG CAG ATT GTC AGC       1200
Trp Arg Pro Gln Gly Thr Arg Gly Pro Trp Gln Glu Gln Ile Val Ser
385                 390                 395                 400

GAC CCC TTC CTG GTG GTG TCC AAC ACG TCC ACC TTC GTG CCC TAT GAG       1248
Asp Pro Phe Leu Val Val Ser Asn Thr Ser Thr Phe Val Pro Tyr Glu
                405                 410                 415

ATC AAA GTC CAG GCC GTC AAC AGC CAG GGC AAG GGA CCA GAG CCC CAG       1296
Ile Lys Val Gln Ala Val Asn Ser Gln Gly Lys Gly Pro Glu Pro Gln
            420                 425                 430

GTC ACT ATC GGC TAC TCT GGA GAG GAC TAC CCC CAG GCA ATC CCT GAG       1344
```

-continued

```
                Val Thr Ile Gly Tyr Ser Gly Glu Asp Tyr Pro Gln Ala Ile Pro Glu
                        435                 440                 445

CTG GAA GGC ATT GAA ATC CTC AAC TCA AGT GCC GTG CTG GTC AAG TGG                1392
Leu Glu Gly Ile Glu Ile Leu Asn Ser Ser Ala Val Leu Val Lys Trp
    450                 455                 460

CGG CCG GTG GAC CTG GCC CAG GTC AAG GGC CAC CTC CGC GGA TAC AAT                1440
Arg Pro Val Asp Leu Ala Gln Val Lys Gly His Leu Arg Gly Tyr Asn
465                 470                 475                 480

GTG ACG TAC TGG AGG GAG GGC AGT CAG AGG AAG CAC AGC AAG AGA CAT                1488
Val Thr Tyr Trp Arg Glu Gly Ser Gln Arg Lys His Ser Lys Arg His
                485                 490                 495

ATC CAC AAA GAC CAT GTG GTG GTG CCC GCC AAC ACC ACC AGT GTC ATC                1536
Ile His Lys Asp His Val Val Val Pro Ala Asn Thr Thr Ser Val Ile
            500                 505                 510

CTC AGT GGC TTG CGG CCC TAT AGC TCC TAC CAC CTG GAG GTG CAG GCC                1584
Leu Ser Gly Leu Arg Pro Tyr Ser Ser Tyr His Leu Glu Val Gln Ala
        515                 520                 525

TTT AAC GGG CGA GGA TCG GGG CCC GCC AGC GAG TTC ACC TTC AGC ACC                1632
Phe Asn Gly Arg Gly Ser Gly Pro Ala Ser Glu Phe Thr Phe Ser Thr
    530                 535                 540

CCA GAG GGA GTG CCT GGC CAC CCC GAG GCG TTG CAC CTG GAG TGC CAG                1680
Pro Glu Gly Val Pro Gly His Pro Glu Ala Leu His Leu Glu Cys Gln
545                 550                 555                 560

TCG AAC ACC AGC CTG CTG CTG CGC TGG CAG CCC CCA CTC AGC CAC AAC                1728
Ser Asn Thr Ser Leu Leu Leu Arg Trp Gln Pro Pro Leu Ser His Asn
                565                 570                 575

GGC GTG CTC ACC GGC TAC GTG CTC TCC TAC CAC CCC CTG GAT GAG GGG                1776
Gly Val Leu Thr Gly Tyr Val Leu Ser Tyr His Pro Leu Asp Glu Gly
            580                 585                 590

GGC AAG GGG CAA CTG TCC TTC AAC CTT CGG GAC CCC GAA CTT CGG ACA                1824
Gly Lys Gly Gln Leu Ser Phe Asn Leu Arg Asp Pro Glu Leu Arg Thr
        595                 600                 605

CAC AAC CTG ACC GAT CTC AGC CCC CAC CTG CGG TAC CGC TTC CAG CTT                1872
His Asn Leu Thr Asp Leu Ser Pro His Leu Arg Tyr Arg Phe Gln Leu
    610                 615                 620

CAG GCC ACC ACC AAA GAG GGC CCT GGT GAA GCC ATC GTA CGG GAA GGA                1920
Gln Ala Thr Thr Lys Glu Gly Pro Gly Glu Ala Ile Val Arg Glu Gly
625                 630                 635                 640

GGC ACT ATG GCC TTG TCT GGG ATC TCA GAT TTT GGC AAC ATC TCA GCC                1968
Gly Thr Met Ala Leu Ser Gly Ile Ser Asp Phe Gly Asn Ile Ser Ala
                645                 650                 655

ACA GCG GGT GAA AAC TAC AGT GTC GTC TCC TGG GTC CCC AAG GAG GGC                2016
Thr Ala Gly Glu Asn Tyr Ser Val Val Ser Trp Val Pro Lys Glu Gly
            660                 665                 670

CAG TGC AAC TTC AGG TTC CAT ATC TTG TTC AAA GCC TTG GGA GAA GAG                2064
Gln Cys Asn Phe Arg Phe His Ile Leu Phe Lys Ala Leu Gly Glu Glu
        675                 680                 685

AAG GGT GGG GCT TCC CTT TCG CCA CAG TAT GTC AGC TAC AAC CAG AGC                2112
Lys Gly Gly Ala Ser Leu Ser Pro Gln Tyr Val Ser Tyr Asn Gln Ser
    690                 695                 700

TCC TAC ACG CAG TGG GAC CTG CAG CCT GAC ACT GAC TAC GAG ATC CAC                2160
Ser Tyr Thr Gln Trp Asp Leu Gln Pro Asp Thr Asp Tyr Glu Ile His
705                 710                 715                 720

TTG TTT AAG GAG AGG ATG TTC CGG CAC CAA ATG GCT GTG AAG ACC AAT                2208
Leu Phe Lys Glu Arg Met Phe Arg His Gln Met Ala Val Lys Thr Asn
                725                 730                 735

GGC ACA GGC CGC GTG AGG CTC CCT CCT GCT GGC TTC GCC ACT GAG GGC                2256
Gly Thr Gly Arg Val Arg Leu Pro Pro Ala Gly Phe Ala Thr Glu Gly
            740                 745                 750

TGG TTC ATC GGC TTT GTG AGT GCC ATC ATC CTC CTG CTC CTG GTC CTG                2304
```

```
Trp Phe Ile Gly Phe Val Ser Ala Ile Ile Leu Leu Leu Val Leu
    755                 760                 765

CTC ATC CTC TGC TTC ATC AAG CGC AGC AAG GGC GGC AAA TAC TCA GTG      2352
Leu Ile Leu Cys Phe Ile Lys Arg Ser Lys Gly Gly Lys Tyr Ser Val
770                 775                 780

AAG GAT AAG GAG GAC ACC CAG GTG GAC TCT GAG GCC CGA CCG ATG AAA      2400
Lys Asp Lys Glu Asp Thr Gln Val Asp Ser Glu Ala Arg Pro Met Lys
785                 790                 795                 800

GAT GAG ACC TTC GGC GAG TAC AGG TCC CTG GAG AGT GAC AAC GAG GAG      2448
Asp Glu Thr Phe Gly Glu Tyr Arg Ser Leu Glu Ser Asp Asn Glu Glu
                805                 810                 815

AAG GCC TTT GGC AGC AGC CAG CCA TCG CTC AAC GGG GAC ATC AAG CCC      2496
Lys Ala Phe Gly Ser Ser Gln Pro Ser Leu Asn Gly Asp Ile Lys Pro
            820                 825                 830

CTG GGC AGT GAC GAC AGC CTG GCC GAT TAT GGG GGC AGC GTG GAT GTT      2544
Leu Gly Ser Asp Asp Ser Leu Ala Asp Tyr Gly Gly Ser Val Asp Val
        835                 840                 845

CAG TTC AAC GAG GAT GGT TCG TTC ATT GGC CAG TAC AGT GGC AAG AAG      2592
Gln Phe Asn Glu Asp Gly Ser Phe Ile Gly Gln Tyr Ser Gly Lys Lys
    850                 855                 860

GAG AAG GA                                                            2600
Glu Lys
865
```

(2) INFORMATION FOR SEQ ID NO:5:

(i) SEQUENCE CHARACTERISTICS:
        (A) LENGTH: 1794
        (B) TYPE: nucleic acid
        (C) STRANDEDNESS: single
        (D) TOPOLOGY: linear (ii) MOLECULE TYPE: nucleic acids (iii) HYPOTHETICAL: irrelevant (iv) ANTI-SENSE: no (vi) ORIGINAL SOURCE:
        (A) ORGANISM: homo sapiens
        (B) INDIVIDUAL ISOLATE: 17-18 week fetus (vii) IMMEDIATE SOURCE:
        (A) LIBRARY: Stratagene cDNA Library 936206
        (B) CLONE: 17

(x) PUBLICATION INFORMATION:
        (A) AUTHORS: Hlavin, Mary Louise
            Lemmon, Vance
        (B) TITLE: Molecular structure and functional testing of
           human L1CAM: an interspecies comparison.
        (C) JOURNAL: GENOMICS
        (D) VOLUME: 11
        (E) ISSUE:
        (F) PAGES: 416-423
        (G) DATE: 1991
        (K) RELEVANT RESIDUES IN SEQ ID NO: 2731 to 4503

(xi) SEQUENCE DESCRIPTION: SEQ ID NO: 5:

```
NGG CCC GCC AGC GAG TTC ACC TTC AGC ACC CCA GAG GGA GTG CCT GGC        48
Xxx Pro Ala Ser Glu Phe Thr Phe Ser Thr Pro Glu Gly Val Pro Gly
1                5                  10                  15

CAC CCC GAG GCG TTG CAC CTG GAG TGC CAG TCG AAC ACC AGC CTG CTG        96
His Pro Glu Ala Leu His Leu Glu Cys Gln Ser Asn Thr Ser Leu Leu
                20                  25                  30

CTG CGC TGG CAG CCC CCA CTC AGC CAC AAC GGC GTG CTC ACC GGC TAC       144
Leu Arg Trp Gln Pro Pro Leu Ser His Asn Gly Val Leu Thr Gly Tyr
            35                  40                  45

GTG CTC TCC TAC CAC CCC CTG GAT GAG GGG GGC AAG GGG CAA CTG TCC       192
```

```
Val Leu Ser Tyr His Pro Leu Asp Glu Gly Gly Lys Gly Gln Leu Ser
     50                  55                  60

TTC AAC CTT CGG GAC CCC GAA CTT CGG ACA CAC AAC CTG ACC GAT CTC      240
Phe Asn Leu Arg Asp Pro Glu Leu Arg Thr His Asn Leu Thr Asp Leu
65                  70                  75                  80

AGC CCC CAC CTG CGG TAC CGC TTC CAG CTT CAG GCC ACC ACC AAA GAG      288
Ser Pro His Leu Arg Tyr Arg Phe Gln Leu Gln Ala Thr Thr Lys Glu
                85                  90                  95

GGC CCT GGT GAA GCC ATC GTA CGG GAA GGA GGC ACT ATG GCC TTG TCT      336
Gly Pro Gly Glu Ala Ile Val Arg Glu Gly Gly Thr Met Ala Leu Ser
            100                 105                 110

GGG ATC TCA GAT TTT GGC AAC ATC TCA GCC ACA GCG GGT GAA AAC TAC      384
Gly Ile Ser Asp Phe Gly Asn Ile Ser Ala Thr Ala Gly Glu Asn Tyr
        115                 120                 125

AGT GTC GTC TCC TGG GTC CCC AAG GAG GGC CAG TGC AAC TTC AGG TTC      432
Ser Val Val Ser Trp Val Pro Lys Glu Gly Gln Cys Asn Phe Arg Phe
    130                 135                 140

CAT ATC TTG TTC AAA GCC TTG GGA GAA GAG AAG GGT GGG GCT TCC CTT      480
His Ile Leu Phe Lys Ala Leu Gly Glu Glu Lys Gly Gly Ala Ser Leu
145                 150                 155                 160

TCG CCA CAG TAT GTC AGC TAC AAC CAG AGC TCC TAC ACG CAG TGG GAC      528
Ser Pro Gln Tyr Val Ser Tyr Asn Gln Ser Ser Tyr Thr Gln Trp Asp
                165                 170                 175

CTG CAG CCT GAC ACT GAC TAC GAG ATC CAC TTG TTT AAG GAG AGG ATG      576
Leu Gln Pro Asp Thr Asp Tyr Glu Ile His Leu Phe Lys Glu Arg Met
            180                 185                 190

TTC CGG CAC CAA ATG GCT GTG AAG ACC AAT GGC ACA GGC CGC GTG AGG      624
Phe Arg His Gln Met Ala Val Lys Thr Asn Gly Thr Gly Arg Val Arg
        195                 200                 205

CTC CCT CCT GCT GGC TTC GCC ACT GAG GGC TGG TTC ATC GGC TTT GTG      672
Leu Pro Pro Ala Gly Phe Ala Thr Glu Gly Trp Phe Ile Gly Phe Val
    210                 215                 220

AGT GCC ATC ATC CTC CTG CTC CTC GTC CTG CTC ATC CTC TGC TTC ATC      720
Ser Ala Ile Ile Leu Leu Leu Leu Val Leu Leu Ile Leu Cys Phe Ile
225                 230                 235                 240

AAG CGC AGC AAG GGC GGC AAA TAC TCA GTG AAG GAT AAG GAG GAC ACC      768
Lys Arg Ser Lys Gly Gly Lys Tyr Ser Val Lys Asp Lys Glu Asp Thr
                245                 250                 255

CAG GTG GAC TCT GAG GCC CGA CCG ATG AAA GAT GAG ACC TTC GGC GAG      816
Gln Val Asp Ser Glu Ala Arg Pro Met Lys Asp Glu Thr Phe Gly Glu
            260                 265                 270

TAC AGG TCC CTG GAG AGT GAC AAC GAG GAG AAG GCC TTT GGC AGC AGC      864
Tyr Arg Ser Leu Glu Ser Asp Asn Glu Glu Lys Ala Phe Gly Ser Ser
        275                 280                 285

CAG CCA TCG CTC AAC GGG GAC ATC AAG CCC CTG GGC AGT GAC GAC AGC      912
Gln Pro Ser Leu Asn Gly Asp Ile Lys Pro Leu Gly Ser Asp Asp Ser
    290                 295                 300

CTG GCC GAT TAT GGG GGC AGC GTG GAT GTT CAG TTC AAC GAG GAT GGT      960
Leu Ala Asp Tyr Gly Gly Ser Val Asp Val Gln Phe Asn Glu Asp Gly
305                 310                 315                 320

TCG TTC ATT GGC CAG TAC AGT GGC AAG AAG GAG AAG GAG GCG GCA GGG     1008
Ser Phe Ile Gly Gln Tyr Ser Gly Lys Lys Glu Lys Glu Ala Ala Gly
                325                 330                 335

GGC AAT GAC AGC TCA GGG GCC ACT TCC CCC ATC AAC CCT GCC GTG GCC     1056
Gly Asn Asp Ser Ser Gly Ala Thr Ser Pro Ile Asn Pro Ala Val Ala
            340                 345                 350

CTA GAA TAGTGGAG TACGGACAGG AGATGCTGTG CCCCCTGGCC TTGGGATCCA        1110
Leu Glu

GGCCCCTCCC TCTCCAGCAG GCCCATGGGA GGCTGGAGTT GGGGCAGAGG AGAACTTGCT   1170
```

-continued

```
GCCTCGGATC CCCTTCCTAC CACCCGGTCC CCACTTTATT GCCAAAACCC AGCTGCACCC    1230

CTTCCTGGGC ACACGCTGCT CTGCCCCAGC TTGGGCAGAT CTCCCACATG CCAGGGGCCT    1290

TTGGGTGCTG TTTTGCCAGC CCATTTGGGC AGAGAGGCTG TGGTTTGGGG GAGAAGAAGT    1350

AGGGGTGGCC CGAAAGGTCT CCGAAATGCT GTCTTTCTTG CTCCCTGACT GGGGGCAGAC    1410

ATGGTGGGGT CTCCTCAGGA CCAGGGTTGG CACCTTCCCC CTCCCCCAGC CACCACTCCA    1470

GCAGCCTGGC TGGGACTGGG AACAGAACTC GTGTCCCAC CATCTGCTGT CTTTTCTTTG    1530

CCATCTCTGC TCCAACCGGG ATGGCAGCCG GGCAAACTGG CCGCGGGGC AGGGGAGGCC    1590

ATCTGGAGAG CCCAGAGTCC CCCCACTCCC AGCATCGCAC TCTGGCAGCA CCGCCTCTTC    1650

CCGCCGCCCA GCCCACCCCA TGGCCGGCTT TCAGGAGCTC CATACACACG CTGCCTTCGG    1710

TACCCACCAC ACAACATCCA AGTGGCCTCC GTCACTACCT GGCTGCGGGG CGGGCACACC    1770

TCCTCCCACT GCCCACTGGC CGGC                                           1794
```

(2) INFORMATION FOR SEQ ID NO:6:

(i) SEQUENCE CHARACTERISTICS:
        (A) LENGTH: 1042
        (B) TYPE: nucleic acid
        (C) STRANDEDNESS: single
        (D) TOPOLOGY: linear (ii) MOLECULE TYPE: nucleic acids (iii) HYPOTHETICAL:     irrelevant (iv) ANTI-SENSE: no (vi) ORIGINAL SOURCE:
        (A) ORGANISM: homo sapiens
        (B) INDIVIDUAL ISOLATE: 17-18 week fetus (vii) IMMEDIATE SOURCE:
        (A) LIBRARY: Stratagene cDNA Library 936206
        (B) CLONE: C2

(x) PUBLICATION INFORMATION:
        (A) AUTHORS:    Hlavin, Mary Louise
           Lemmon, Vance
        (B) TITLE:     Molecular structure and functional testing of
           human L1CAM: an interspecies comparison.
        (C) JOURNAL:   GENOMICS
        (D) VOLUME:    11
        (E) ISSUE:
        (F) PAGES:     416-423
        (G) DATE:      1991
        (K) RELEVANT RESIDUES IN SEQ ID NO:  -26 to 1016

(xi) SEQUENCE DESCRIPTION: SEQ ID NO: 6:

```
CGTGCTCCGC GGTGCCGCCG GGAAAG ATG GTC GTG GCG CTG CGG TAC GTG TGG       53
                            Met Val Val Ala Leu Arg Tyr Val Trp
                             1               5

CCT CTC CTC CTC TGC AGC CCC TGC CTG CTT ATC CAG ATC CCC GAG GAA      101
Pro Leu Leu Leu Cys Ser Pro Cys Leu Leu Ile Gln Ile Pro Glu Glu
 10              15                  20                  25

TAT GAA GGA CAC CAT GTG ATG GAG CCA CCT GTC ATC ACG GAA CAG TCT      149
Tyr Glu Gly His His Val Met Glu Pro Pro Val Ile Thr Glu Gln Ser
             30                  35                  40

CCA CGG CGC CTG GTT GTC TTC CCC ACA GAT GAC ATC AGC CTC AAG TGT      197
Pro Arg Arg Leu Val Val Phe Pro Thr Asp Asp Ile Ser Leu Lys Cys
         45                  50                  55

GAG GCC AGT GGC AAG CCC GAA GTG CAG TTC CGC TGG ACG AGG GAT GGT      245
Glu Ala Ser Gly Lys Pro Glu Val Gln Phe Arg Trp Thr Arg Asp Gly
     60                  65                  70

GTC CAC TTC AAA CCC AAG GAA GAG CTG GGT GTG ACC GTG TAC CAG TCG      293
```

```
                Val His Phe Lys Pro Lys Glu Glu Leu Gly Val Thr Val Tyr Gln Ser
                     75                  80                  85

CCC CAC TCT GGC TCC TTC ACC ATC ACG GGC AAC AAC AGC AAC TTT GCT             341
Pro His Ser Gly Ser Phe Thr Ile Thr Gly Asn Asn Ser Asn Phe Ala
 90                  95                 100                 105

CAG AGG TTC CAG GGC ATC TAC CGC TGC TTT GCC AGC AAT AAG CTG GGC             389
Gln Arg Phe Gln Gly Ile Tyr Arg Cys Phe Ala Ser Asn Lys Leu Gly
                    110                 115                 120

ACC GCC ATG TCC CAT GAG ATC CGG CTC ATG GCC GAG GGT GCC CCC AAG             437
Thr Ala Met Ser His Glu Ile Arg Leu Met Ala Glu Gly Ala Pro Lys
                125                 130                 135

TGG CCA AAG GAG ACA GTG AAG CCC GTG GAG GTG GAG GAA GGG GAG TCA             485
Trp Pro Lys Glu Thr Val Lys Pro Val Glu Val Glu Glu Gly Glu Ser
            140                 145                 150

GTG GTT CTG CCT TGC AAC CCT CCC CCA AGT GCA GAG CCT CTC CGG ATC             533
Val Val Leu Pro Cys Asn Pro Pro Pro Ser Ala Glu Pro Leu Arg Ile
        155                 160                 165

TAC TGG ATG AAC AGC AAG ATC TTG CAC ATC AAG CAG GAC GAG CGG GTG             581
Tyr Trp Met Asn Ser Lys Ile Leu His Ile Lys Gln Asp Glu Arg Val
170                 175                 180                 185

ACG ATG GGC CAG AAC GGC AAC CTC TAC TTT GCC AAT GTG CTC ACC TCC             629
Thr Met Gly Gln Asn Gly Asn Leu Tyr Phe Ala Asn Val Leu Thr Ser
                    190                 195                 200

GAC AAC CAC TCA GAC TAC ATC TGC CAC GCC CAC TTC CCA GGC ACC AGG             677
Asp Asn His Ser Asp Tyr Ile Cys His Ala His Phe Pro Gly Thr Arg
                205                 210                 215

ACC ATC ATT CAG AAG GAA CCC ATT GAC CTC CGG GTC AAG GCC ACC AAC             725
Thr Ile Ile Gln Lys Glu Pro Ile Asp Leu Arg Val Lys Ala Thr Asn
            220                 225                 230

AGC ATG ATT GAC AGG AAG CCG CGC CTG CTC TTC CCC ACC AAC TCC AGC             773
Ser Met Ile Asp Arg Lys Pro Arg Leu Leu Phe Pro Thr Asn Ser Ser
        235                 240                 245

AGC CAC CTG GTG GCC TTG CAG GGG CAG CCA TTG GTC CTG GAG TGC ATC             821
Ser His Leu Val Ala Leu Gln Gly Gln Pro Leu Val Leu Glu Cys Ile
250                 255                 260                 265

GCC GAG GGC TTT CCC ACG CCC ACC ATC AAA TGG CTG CGC CCC AGT GGC             869
Ala Glu Gly Phe Pro Thr Pro Thr Ile Lys Trp Leu Arg Pro Ser Gly
                    270                 275                 280

CCC ATG CCA GCT GAC CGT GTC ACC TAC CAG AAC CAC AAC AAG ACC CTG             917
Pro Met Pro Ala Asp Arg Val Thr Tyr Gln Asn His Asn Lys Thr Leu
                285                 290                 295

CAG CTG CTG AAA GTG GGC GAG GAG GAT GAT GGC GAG TAC CGC TGC CTG             965
Gln Leu Leu Lys Val Gly Glu Glu Asp Asp Gly Glu Tyr Arg Cys Leu
            300                 305                 310

GCC GAG AAC TCA CTG GGC AGT GCC CGG CAT GCG TAC TAT GTC ACC GTG            1013
Ala Glu Asn Ser Leu Gly Ser Ala Arg His Ala Tyr Tyr Val Thr Val
        315                 320                 325

GAG GCT GCC CCG TAC TGG CTG CAC AAG CC                                     1042
Glu Ala Ala Pro Tyr Trp Leu His Lys
330                 335
```

(2) INFORMATION FOR SEQ ID NO: 7:

(i) SEQUENCE CHARACTERISTICS:
        (A) LENGTH: 50
        (B) TYPE: nucleic acid
        (C) STRANDEDNESS: single
        (D) TOPOLOGY: linear (ii) MOLECULE TYPE: oligonucleotide (iii) HYPOTHETICAL: irrelevant (iv) ANTI-SENSE: no (vi) ORIGINAL SOURCE:
             (A) ORGANISM: mouse (x) SEQUENCE DESCRIPTION: SEQ ID NO: 7:

GAGGACACCC AGGTGGACTC TGAGGCCCGA CCGATGAAAG ATGAGACCTT                    50

(2) INFORMATION FOR SEQ ID NO: 8:

(i) SEQUENCE CHARACTERISTICS:
            (A) LENGTH: 40
            (B) TYPE: nucleic acid
            (C) STRANDEDNESS: single
            (D) TOPOLOGY: linear (ii) MOLECULE TYPE: oligonucleotide (iii) HYPOTHETICAL: irrelevant (iv) ANTI-SENSE: no (x) SEQUENCE DESCRIPTION: SEQ ID NO: 8:

TGCCACGCCC ACTTCCCAGG CACCAGGACC ATCATTCAGA                               40

(2) INFORMATION FOR SEQ ID NO: 9:

(i) SEQUENCE CHARACTERISTICS:
            (A) LENGTH: 95
            (B) TYPE: amino acid
            (C) STRANDEDNESS: single
            (D) TOPOLOGY: linear (ii) MOLECULE TYPE: amino acids (iii) HYPOTHETICAL: irrelevant (iv) ANTI-SENSE: no (vi) ORIGINAL SOURCE:
            (A) ORGANISM: mouse
            (B) INDIVIDUAL ISOLATE: 8 day old mouse brain (vii) IMMEDIATE SOURCE:
            (A) LIBRARY: lamda GT 10 and lamda GT11
            (B) CLONE: synthesis of several clones (x) PUBLICATION INFORMATION:
            (A) AUTHORS: Moos, M.
                Tacke, R.
                Scherer, H.
                Teplow, D.
                Fruh, K.
                Schachner, M.
            (B) TITLE: Neural adhesion molecule L1 is a
                member of the immunoglobulin
                superfamily with binding domains
                similar to fibronectin
            (C) JOURNAL: NATURE
            (D) VOLUME: 334
            (E) ISSUE:
            (F) PAGES: 701-703
            (G) DATE: 1988

(xi) SEQUENCE DESCRIPTION: SEQ ID NO: 9:

Val Ile Thr Glu Gln Ser Pro Arg Arg Leu Val Val Phe Pro Thr Asp Asp
1               5                   10                  15

Ile Ser Leu Lys Cys Glu Ala Arg Gly Arg Pro Gln Val Glu Phe Arg Trp
            20                  25                  30

Thr Lys Asp Gly Ile His Phe Lys Pro Lys Glu Glu Leu Gly Val Val Val
35                  40                  45                  50

His Glu Ala Pro Tyr Ser Gly Ser Phe Thr Ile Glu Gly Asn Asn Ser Phe

```
                        55                   60                   65
Ala Gln Arg Phe Gln Gly Ile Tyr Arg Cys Tyr Ala Ser Asn Lys Leu Gly
            70                  75                  80                  85

Thr Ala Met Ser His Glu Ile Gln Leu Val
                90                  95
```

(2) INFORMATION FOR SEQ ID NO: 10:

(i) SEQUENCE CHARACTERISTICS:
        (A) LENGTH: 106
        (B) TYPE: amino acid
        (C) STRANDEDNESS: single
        (D) TOPOLOGY: linear (ii) MOLECULE TYPE: amino acids (iii) HYPOTHETICAL: irrelevant (iv) ANTI-SENSE: no (vi) ORIGINAL SOURCE:
        (A) ORGANISM: mouse
        (B) INDIVIDUAL ISOLATE: 8 day old mouse brain (vii) IMMEDIATE SOURCE:
        (A) LIBRARY: lamda GT 10 and lamda GT11
        (B) CLONE: synthesis of several clones (x) PUBLICATION INFORMATION:
        (A) AUTHORS: Moos, M.
            Tacke, R.
            Scherer, H.
            Teplow, D.
            Fruh, K.
            Schachner, M.
        (B) TITLE: Neural adhesion molecule L1 is a
            member of the immunoglobulin
            superfamily with binding domains
            similar to fibronectin
        (C) JOURNAL: NATURE
        (D) VOLUME: 334
        (E) ISSUE:
        (F) PAGES: 701-703
        (G) DATE: 1988

(xi) SEQUENCE DESCRIPTION: SEQ ID NO: 10:

```
Ala Glu Gly Ala Pro Lys Trp Pro Lys Glu Thr Val Lys Pro Val Glu Val
1               5                   10                  15

Glu Glu Gly Glu Ser Val Val Leu Pro Cys Asn Pro Pro Ser Ala Ala
            20                  25                  30

Pro Pro Arg Ile Tyr Trp Met Asn Ser Ile Phe Asp Ile Lys Gln Asp
35                  40                  45                  50

Glu Arg Val Ser Met Gly Gln Asn Gly Asp Leu Tyr Phe Ala Asn Val Leu
            55                  60                  65

Thr Ser Asp Asn His Ser Asp Tyr Ile Cys Asn Ala His Phe Pro Gly Thr
        70                  75                  80                  85

Arg Thr Ile Ile Gln Lys Glu Pro Ile Asp Leu Arg Val Lys Pro Thr Asn
                90                  95                  100

Ser Met Ile Asp
        105
```

(2) INFORMATION FOR SEQ ID NO: 11:

(i) SEQUENCE CHARACTERISTICS:
        (A) LENGTH: 96
        (B) TYPE: amino acid
        (C) STRANDEDNESS: single
        (D) TOPOLOGY: linear (ii) MOLECULE TYPE: amino acids (iii) HYPOTHETICAL: irrelevant (iv) ANTI-SENSE: no (vi) ORIGINAL SOURCE:
         (A) ORGANISM: mouse
         (B) INDIVIDUAL ISOLATE: 8 day old mouse brain (vii) IMMEDIATE SOURCE:
         (A) LIBRARY: lamda GT 10 and lamda GT11
         (B) CLONE: synthesis of several clones (x) PUBLICATION INFORMATION:
         (A) AUTHORS: Moos, M.
              Tacke, R.
              Scherer, H.
              Teplow, D.
              Fruh, K.
              Schachner, M.
         (B) TITLE: Neural adhesion molecule L1 is a
              member of the immunoglobulin
              superfamily with binding domains
              similar to fibronectin
         (C) JOURNAL: NATURE
         (D) VOLUME: 334
         (E) ISSUE:
         (F) PAGES: 701-703
         (G) DATE: 1988

(xi) SEQUENCE DESCRIPTION: SEQ ID NO: 11:

Arg Lys Pro Arg Leu Leu Phe Pro Thr Asn Ser Ser Arg Leu Val Ala
1               5                   10                  15

Leu Gln Gly Gln Ser Leu Ile Leu Glu Cys Ile Ala Glu Gly Phe Pro Thr
            20                  25                  30

Pro Thr Ile Lys Trp Leu His Pro Ser Asp Pro Met Pro Thr Asp Arg Val
35                  40                  45                  50

Ile Tyr Gln Asn His Asn Lys Thr Leu Gln Leu Leu Asn Val Gly Glu Glu
                55                  60                  65

Asp Asp Gly Glu Tyr Thr Cys Leu Ala Glu Asn Ser Leu Gly Ser Ala Arg
70                  75                  80                      85

His Ala Tyr Tyr Val Thr Val Glu Ala Ala Pro
                90                  95

(2) INFORMATION FOR SEQ ID NO: 12:

(i) SEQUENCE CHARACTERISTICS:
         (A) LENGTH: 92
         (B) TYPE: amino acid
         (C) STRANDEDNESS: single
         (D) TOPOLOGY: linear (ii) MOLECULE TYPE: amino acids (iii) HYPOTHETICAL: irrelevant (iv) ANTI-SENSE: no (vi) ORIGINAL SOURCE:
         (A) ORGANISM: mouse
         (B) INDIVIDUAL ISOLATE: 8 day old mouse brain (vii) IMMEDIATE SOURCE:
         (A) LIBRARY: lamda GT 10 and lamda GT11
         (B) CLONE: synthesis of several clones (x) PUBLICATION INFORMATION:
         (A) AUTHORS: Moos, M.
              Tacke, R.
              Scherer, H.
              Teplow, D.
              Fruh, K.

Schachner, M.
(B) TITLE: Neural adhesion molecule L1 is a
member of the immunoglobulin
superfamily with binding domains
similar to fibronectin
(C) JOURNAL: NATURE
(D) VOLUME: 334
(E) ISSUE:
(F) PAGES: 701-703
(G) DATE: 1988

(xi) SEQUENCE DESCRIPTION: SEQ ID NO: 12:

Tyr Trp Leu Gln Lys Pro Gln Ser His Leu Tyr Gly Pro Gly Glu Thr Ala
1               5                   10                  15

Arg Leu Asp Cys Gln Val Gln Gly Arg Pro Gln Pro Glu Ile Thr Trp Arg
        20                  25                  30

Ile Asn Gly Met Ser Met Glu Thr Val Asn Lys Asp Gln Lys Tyr Arg Ile
35                  40                  45                  50

Glu Gln Gly Ser Leu Ile Leu Ser Asn Val Gln Pro Thr Asp Thr Met Val
            55                  60                  65

Thr Gln Cys Glu Ala Arg Asn Gln His Gly Leu Leu Leu Ala Asn Ala Tyr
    70                  75                  80                  85

Ile Tyr Val Val Gln Leu Pro
                90

(2) INFORMATION FOR SEQ ID NO: 13:

(i) SEQUENCE CHARACTERISTICS:
        (A) LENGTH: 93
        (B) TYPE: amino acid
        (C) STRANDEDNESS: single
        (D) TOPOLOGY: linear (ii) MOLECULE TYPE: amino acids (iii) HYPOTHETICAL: irrelevant (iv) ANTI-SENSE: no (vi) ORIGINAL SOURCE:
        (A) ORGANISM: mouse
        (B) INDIVIDUAL ISOLATE: 8 day old mouse brain (vii) IMMEDIATE SOURCE:
        (A) LIBRARY: lamda GT 10 and lamda GT11
        (B) CLONE: synthesis of several clones (x) PUBLICATION INFORMATION:
        (A) AUTHORS: Moos, M.
            Tacke, R.
            Scherer, H.
            Teplow, D.
            Fruh, K.
            Schachner, M.
        (B) TITLE: Neural adhesion molecule L1 is a
            member of the immunoglobulin
            superfamily with binding domains
            similar to fibronectin
        (C) JOURNAL: NATURE
        (D) VOLUME: 334
        (E) ISSUE:
        (F) PAGES: 701-703
        (G) DATE: 1988

(xi) SEQUENCE DESCRIPTION: SEQ ID NO: 13:

Ala Arg Ile Leu Thr Lys Asp Asn Gln Thr Tyr Met Ala Val Glu Gly Ser
1               5                   10                  15

Thr Ala Tyr Leu Leu Cys Lys Ala Phe Gly Ala Pro Val Pro Ser Val Gln
        20                  25                  30

Trp Leu Asp Glu Glu Gly Thr Thr Val Leu Gln Asp Glu Arg Phe Phe Pro

```
                35              40              45              50
Tyr Ala Asn Gly Thr Leu Ser Ile Arg Asp Leu Gln Ala Asn Asp Thr Gly
                55                  60                  65

Arg Tyr Phe Cys Gln Ala Ala Asn Asp Gln Asn Asn Val Ile Ile Leu Ala
    70                  75                  80                  85

Asn Leu Gln Val Lys Glu Ala Thr
                90
```

(2) INFORMATION FOR SEQ ID NO: 14:

(i) SEQUENCE CHARACTERISTICS:
        (A) LENGTH: 96
        (B) TYPE: amino acid
        (C) STRANDEDNESS: single
        (D) TOPOLOGY: linear (ii) MOLECULE TYPE: amino acids (iii) HYPOTHETICAL: irrelevant (iv) ANTI-SENSE: no (vi) ORIGINAL SOURCE:
        (A) ORGANISM: mouse
        (B) INDIVIDUAL ISOLATE: 8 day old mouse brain (vii) IMMEDIATE SOURCE:
        (A) LIBRARY: lamda GT 10 and lamda GT11
        (B) CLONE: synthesis of several clones (x) PUBLICATION INFORMATION:
        (A) AUTHORS: Moos, M.
            Tacke, R.
            Scherer, H.
            Teplow, D.
            Fruh, K.
            Schachner, M.
        (B) TITLE: Neural adhesion molecule L1 is a member of the immunoglobulin superfamily with binding domains similar to fibronectin
        (C) JOURNAL: NATURE
        (D) VOLUME: 334
        (E) ISSUE:
        (F) PAGES: 701-703
        (G) DATE: 1988

(xi) SEQUENCE DESCRIPTION: SEQ ID NO: 14:

```
Gln Ile Thr Gln Gly Pro Arg Ser Ala Ile Glu Lys Lys Gly Ala Arg Val
1               5                   10                  15

Thr Phe Thr Cys Gln Ala Ser Phe Asp Pro Ser Leu Gln Ala Ser Ile Thr
                20                  25                  30

Trp Arg Gly Asp Gly Arg Asp Leu Gln Glu Arg Gly Asp Ser Asp Lys Tyr
35                  40                  45                  50

Phe Ile Glu Asp Gly Lys Leu Val Ile Gln Ser Leu Asp Tyr Ser Asp Gln
                55                  60                  65

Gly Asn Tyr Ser Cys Val Ala Ser Thr Glu Leu Asp Glu Val Glu Ser Arg
                70                  75                  80                  85

Ala Gln Leu Leu Val Val Gly Ser Pro Gly Pro
                90                  95
```

(2) INFORMATION FOR SEQ ID NO: 15:

(i) SEQUENCE CHARACTERISTICS:
        (A) LENGTH: 101
        (B) TYPE: amino acid
        (C) STRANDEDNESS: single
        (D) TOPOLOGY: linear (ii) MOLECULE TYPE:  amino acids (iii) HYPOTHETICAL:  irrelevant (iv) ANTI-SENSE:  no (vi) ORIGINAL SOURCE:
              (A) ORGANISM:  mouse
              (B) INDIVIDUAL ISOLATE:  8 day old mouse brain (vii) IMMEDIATE SOURCE:
              (A) LIBRARY:  lamda GT 10 and lamda GT11
              (B) CLONE:  synthesis of several clones (x) PUBLICATION INFORMATION:
              (A) AUTHORS: Moos, M.
                   Tacke, R.
                   Scherer, H.
                   Teplow, D.
                   Fruh, K.
                   Schachner, M.
              (B) TITLE:  Neural adhesion molecule L1 is a
                   member of the immunoglobulin
                   superfamily with binding domains
                   similar to fibronectin
              (C) JOURNAL:  NATURE
              (D) VOLUME:  334
              (E) ISSUE:
              (F) PAGES:  701-703
              (G) DATE:  1988

(xi) SEQUENCE DESCRIPTION:  SEQ ID NO: 15:

Val Pro His Leu Glu Leu Ser Asp Arg His Leu Leu Lys Gln Ser Gln Val
 1               5                  10                  15

His Leu Ser Trp Ser Pro Ala Glu Asp His Asn Ser Pro Ile Glu Lys Tyr
            20                  25                  30

Asp Ile Glu Phe Glu Asp Lys Glu Met Ala Pro Glu Lys Trp Phe Ser Leu
35                  40                  45                  50

Gly Lys Val Pro Gly Asn Gln Thr Ser Thr Thr Leu Lys Leu Ser Pro Tyr
            55                  60                  65

Val His Tyr Thr Phe Arg Val Thr Ala Ile Asn Lys Tyr Gly Pro Gly Glu
     70                  75                  80                  85

Pro Ser Pro Val Ser Glu Ser Val Val Thr Pro Glu Ala Ala Pro Glu
                 90                  95                 100

(2) INFORMATION FOR SEQ ID NO: 16:

(i) SEQUENCE CHARACTERISTICS:
              (A) LENGTH: 96
              (B) TYPE:  amino acid
              (C) STRANDEDNESS:  single
              (D) TOPOLOGY:  linear (ii) MOLECULE TYPE:  amino acids (iii) HYPOTHETICAL:  irrelevant (iv) ANTI-SENSE:  no (vi) ORIGINAL SOURCE:
              (A) ORGANISM:  mouse
              (B) INDIVIDUAL ISOLATE:  8 day old mouse brain (vii) IMMEDIATE SOURCE:
              (A) LIBRARY:  lamda GT 10 and lamda GT11
              (B) CLONE:  synthesis of several clones (x) PUBLICATION INFORMATION:
              (A) AUTHORS: Moos, M.
                   Tacke, R.
                   Scherer, H.
                   Teplow, D.
                   Fruh, K.

Schachner, M.
(B) TITLE: Neural adhesion molecule L1 is a
member of the immunoglobulin
superfamily with binding domains
similar to fibronectin
(C) JOURNAL: NATURE
(D) VOLUME: 334
(E) ISSUE:
(F) PAGES: 701-703
(G) DATE: 1988

(xi) SEQUENCE DESCRIPTION: SEQ ID NO: 16:

Lys Asn Pro Val Asp Val Arg Gly Glu Gly Asn Glu Thr Asn Met Val
1               5                   10                  15

Ile Thr Trp Lys Pro Leu Arg Trp Met Asp Trp Asn Ala Pro Gln Ile Gln
            20                  25                  30

Tyr Arg Val Gln Trp Arg Pro Gln Gly Lys Gln Glu Thr Trp Arg Lys Gln
35                  40                  45                  50

Thr Val Ser Asp Pro Phe Leu Val Val Ser Asn Thr Ser Thr Phe Val Pro
                55                  60                  65

Tyr Glu Ile Lys Val Gln Ala Val Asn Asn Gly Lys Gly Pro Glu Pro
            70                  75                  80                  85

Gln Val Thr Ile Gly Tyr Ser Gly Glu Asp Tyr
                90                  95

(2) INFORMATION FOR SEQ ID NO: 17:

(i) SEQUENCE CHARACTERISTICS:
        (A) LENGTH: 106
        (B) TYPE: amino acid
        (C) STRANDEDNESS: single
        (D) TOPOLOGY: linear (ii) MOLECULE TYPE: amino acids (iii) HYPOTHETICAL: irrelevant (iv) ANTI-SENSE: no (vi) ORIGINAL SOURCE:
        (A) ORGANISM: mouse
        (B) INDIVIDUAL ISOLATE: 8 day old mouse brain (vii) IMMEDIATE SOURCE:
        (A) LIBRARY: lamda GT 10 and lamda GT11
        (B) CLONE: synthesis of several clones (x) PUBLICATION INFORMATION:
        (A) AUTHORS: Moos, M.
            Tacke, R.
            Scherer, H.
            Teplow, D.
            Fruh, K.
            Schachner, M.
        (B) TITLE: Neural adhesion molecule L1 is a
            member of the immunoglobulin
            superfamily with binding domains
            similar to fibronectin
        (C) JOURNAL: NATURE
        (D) VOLUME: 334
        (E) ISSUE:
        (F) PAGES: 701-703
        (G) DATE: 1988

(xi) SEQUENCE DESCRIPTION: SEQ ID NO: 17:

Pro Gln Val Ser Pro Glu Leu Glu Asp Ile Thr Ile Phe Asn Ser Ser Thr
1               5                   10                  15

Val Leu Val Arg Trp Arg Pro Val Asp Leu Ala Gln Val Lys Gly His Leu
            20                  25                  30

Lys Gly Tyr Asn Val Thr Tyr Trp Trp Lys Gly Ser Gln Arg Lys His Ser

```
                35                  40                  45                  50
Lys Arg His Ile His Lys Ser His Ile Val Val Pro Ala Asn Thr Thr Ser
                55                  60                  65

Ala Ile Leu Ser Gly Leu Arg Pro Tyr Ser Ser Tyr His Val Glu Val Gln
        70                  75                  80                  85

Ala Phe Asn Gly Arg Gly Leu Gly Pro Ala Ser Glu Trp Thr Phe Ser Thr
                90                  95                 100

Pro Glu Gly Val
        105
```

(2) INFORMATION FOR SEQ ID NO: 18:

(i) SEQUENCE CHARACTERISTICS:
        (A) LENGTH: 98
        (B) TYPE: amino acid
        (C) STRANDEDNESS: single
        (D) TOPOLOGY: linear (ii) MOLECULE TYPE: amino acids (iii) HYPOTHETICAL: irrelevant (iv) ANTI-SENSE: no (vi) ORIGINAL SOURCE:
        (A) ORGANISM: mouse
        (B) INDIVIDUAL ISOLATE: 8 day old mouse brain (vii) IMMEDIATE SOURCE:
        (A) LIBRARY: lamda GT 10 and lamda GT11
        (B) CLONE: synthesis of several clones (x) PUBLICATION INFORMATION:
        (A) AUTHORS: Moos, M.
            Tacke, R.
            Scherer, H.
            Teplow, D.
            Fruh, K.
            Schachner, M.
        (B) TITLE: Neural adhesion molecule L1 is a member of the immunoglobulin superfamily with binding domains similar to fibronectin
        (C) JOURNAL: NATURE
        (D) VOLUME: 334
        (E) ISSUE:
        (F) PAGES: 701-703
        (G) DATE: 1988

(xi) SEQUENCE DESCRIPTION: SEQ ID NO: 18:

```
Pro Gly His Pro Glu Ala Leu His Leu Glu Cys Gln Ser Asp Thr Ser Leu
 1               5                  10                  15

Leu Leu His Trp Gln Pro Pro Leu Ser His Asn Gly Val Leu Thr Gly Tyr
        20                  25                  30

Leu Leu Ser Tyr His Pro Val Glu Gly Glu Ser Lys Glu Gln Leu Phe Phe
35                  40                  45                  50

Asn Leu Ser Asp Pro Glu Leu Arg Thr His Asn Leu Thr Asn Leu Asn Pro
                55                  60                  65

Asp Leu Gln Tyr Arg Phe Gln Leu Gln Ala Thr Thr Gln Gln Gly Gly Pro
        70                  75                  80                  85

Gly Glu Ala Ile Val Arg Glu Gly Gly Thr Met Ala Leu
                90                  95
```

(2) INFORMATION FOR SEQ ID NO: 19:

(i) SEQUENCE CHARACTERISTICS:
        (A) LENGTH: 101
        (B) TYPE: amino acid

```
          (C) STRANDEDNESS:  single
          (D) TOPOLOGY:  linear (ii) MOLECULE TYPE:  amino acids (iii) HYPOTHETICAL:  irrelevant (iv) ANTI-SENSE:  no (vi) ORIGINAL SOURCE:
          (A) ORGANISM:  mouse
          (B) INDIVIDUAL ISOLATE:  8 day old mouse brain (vii) IMMEDIATE SOURCE:
          (A) LIBRARY:  lamda GT 10 and lamda GT11
          (B) CLONE:  synthesis of several clones (x) PUBLICATION INFORMATION:
          (A) AUTHORS:      Moos, M.
              Tacke, R.
              Scherer, H.
              Teplow, D.
              Fruh, K.
              Schachner, M.
          (B) TITLE:        Neural adhesion molecule L1 is a
              member of the immunoglobulin
              superfamily with binding domains
              similar to fibronectin
          (C) JOURNAL:  NATURE
          (D) VOLUME:   334
          (E) ISSUE:
          (F) PAGES:    701-703
          (G) DATE:     1988

(xi) SEQUENCE DESCRIPTION:  SEQ ID NO: 19:
```

Phe Gly Lys Pro Asp Phe Gly Asn Ile Ser Ala Thr Ala Gly Glu Asn Tyr
1               5                  10                  15

Ser Val Val Ser Trp Val Pro Arg Lys Gly Gln Cys Asn Phe Arg Phe His
            20                  25                  30

Ile Leu Phe Lys Ala Leu Pro Glu Gly Lys Val Ser Pro Asp His Gln Pro
35                  40                  45                  50

Gln Pro Gln Tyr Val Ser Tyr Asn Gln Ser Ser Tyr Thr Gln Trp Asn Leu
            55                  60                  65

Gln Pro Asp Thr Lys Tyr Glu Ile His Leu Ile Lys Glu Lys Val Leu Leu
        70                  75              80                  85

His His Leu Asp Val Lys Thr Asn Gly Thr Gly Pro Val Arg Val Ser
                90                  95                  100

```
(2) INFORMATION FOR SEQ ID NO: 20:

(i) SEQUENCE CHARACTERISTICS:
          (A) LENGTH: 145
          (B) TYPE: amino acid
          (C) STRANDEDNESS:  single
          (D) TOPOLOGY:  linear (ii) MOLECULE TYPE:  amino acids (iii) HYPOTHETICAL:  irrelevant (iv) ANTI-SENSE:  no (vi) ORIGINAL SOURCE:
          (A) ORGANISM:  mouse
          (B) INDIVIDUAL ISOLATE:  8 day old mouse brain (vii) IMMEDIATE SOURCE:
          (A) LIBRARY:  lamda GT 10 and lamda GT11
          (B) CLONE:  synthesis of several clones (x) PUBLICATION INFORMATION:
          (A) AUTHORS:      Moos, M.
              Tacke, R.
```

```
                    Scherer, H.
                    Teplow, D.
                    Fruh, K.
                    Schachner, M.
            (B) TITLE:       Neural adhesion molecule L1 is a
                    member of the immunoglobulin
                    superfamily with binding domains
                    similar to fibronectin
            (C) JOURNAL:  NATURE
            (D) VOLUME:   334
            (E) ISSUE:
            (F) PAGES:    701-703
            (G) DATE:         1988

(xi) SEQUENCE DESCRIPTION:  SEQ ID NO: 20:

Thr Thr Gly Ser Phe Ala Ser Glu Gly Trp Phe Ile Ala Phe Val Ser Ala
 1               5                  10                  15

Ile Ile Leu Leu Leu Leu Ile Leu Leu Ile Leu Cys Phe Ile Lys Arg Ser
            20                  25                  30

Lys Gly Gly Lys Tyr Ser Val Lys Asp Lys Glu Asp Thr Gln Val Asp Ser
 35                  40                  45                  50

Glu Ala Arg Pro Met Lys Asp Glu Thr Phe Gly Glu Tyr Arg Ser Leu Glu
                55                  60                  65

Ser Asp Asn Glu Glu Lys Ala Phe Gly Ser Ser Gln Pro Ser Leu Asn Gly
 70                  75                  80                       85

Asp Ile Lys Pro Leu Gly Ser Asp Asp Ser Leu Ala Asp Tyr Gly Gly Ser
                90                  95                 100

Val Asp Val Gln Phe Asn Glu Asp Gly Ser Phe Ile Gly Gln Tyr Ser Gly
            105                 110                 115

Lys Lys Glu Lys Glu Ala Ala Gly Gly Asn Asp Ser Ser Gly Ala Thr Ser
120                 125                 130                 135

Pro Ile Asn Pro Ala Val Ala Leu Glu
                140                 145

(2) INFORMATION FOR SEQ ID NO: 21:

(i) SEQUENCE CHARACTERISTICS:
            (A) LENGTH: 96
            (B) TYPE: amino acid
            (C) STRANDEDNESS:  single
            (D) TOPOLOGY:   linear (ii) MOLECULE TYPE:  amino acids (iii) HYPOTHETICAL:  irrelevant (iv) ANTI-SENSE:  no (vi) ORIGINAL SOURCE:
            (A) ORGANISM:  Homo Sapiens
            (B) INDIVIDUAL ISOLATE:  17-18 week fetus (vii) IMMEDIATE SOURCE:
            (A) LIBRARY:  Stratagene cDNA Library 936206
            (B) CLONE:  synthesis of 4 clones (x) PUBLICATION INFORMATION:
            (A) AUTHORS: Hlavin, Mary Louise
                    Lemmon, Vance
            (B) TITLE:    Molecular structure and functional
                    testing of human L1CAM: an interspecies
                    comparison.
            (C) JOURNAL:  GENOMICS
            (D) VOLUME:   11
            (E) ISSUE:
            (F) PAGES:    416-423
            (G) DATE:         1991

(xi) SEQUENCE DESCRIPTION:  SEQ ID NO: 21:
```

```
Val Ile Thr Glu Gln Ser Pro Arg Arg Leu Val Val Phe Pro Thr Asp Asp
1               5                  10                 15

Ile Ser Leu Lys Cys Glu Ala Ser Gly Lys Pro Glu Val Gln Phe Arg Trp
            20                  25              30

Thr Arg Asp Gly Val His Phe Lys Pro Lys Glu Glu Leu Gly Val Thr Val
35              40                  45                  50

Tyr Gln Ser Pro His Ser Gly Ser Phe Thr Ile Thr Gly Asn Asn Ser Asn
                55                  60                  65

Phe Ala Gln Arg Phe Gln Gly Ile Tyr Arg Cys Phe Ala Ser Asn Lys Leu
70                  75                  80                  85

Gly Thr Ala Met Ser His Glu Ile Arg Leu Met
                90                  95
```

(2) INFORMATION FOR SEQ ID NO: 22:

(i) SEQUENCE CHARACTERISTICS:
  (A) LENGTH: 106
  (B) TYPE: amino acid
  (C) STRANDEDNESS: single
  (D) TOPOLOGY: linear (ii) MOLECULE TYPE: amino acids (iii) HYPOTHETICAL: irrelevant (iv) ANTI-SENSE: no (vi) ORIGINAL SOURCE:
  (A) ORGANISM: Homo Sapiens
  (B) INDIVIDUAL ISOLATE: 17-18 week fetus (vii) IMMEDIATE SOURCE:
  (A) LIBRARY: Stratagene cDNA Library 936206
  (B) CLONE: synthesis of 4 clones (x) PUBLICATION INFORMATION:
  (A) AUTHORS: Hlavin, Mary Louise
   Lemmon, Vance
  (B) TITLE: Molecular structure and functional testing of human L1CAM: an interspecies comparison.
  (C) JOURNAL: GENOMICS
  (D) VOLUME: 11
  (E) ISSUE:
  (F) PAGES: 416-423
  (G) DATE: 1991

(xi) SEQUENCE DESCRIPTION: SEQ ID NO: 22:

```
Ala Glu Gly Ala Pro Lys Trp Pro Lys Glu Thr Val Lys Pro Val Glu Val
1               5                   10                  15

Glu Glu Gly Glu Ser Val Val Leu Pro Cys Asn Pro Pro Ser Ala Glu
            20                  25                  30

Pro Leu Arg Ile Tyr Trp Met Asn Ser Lys Ile Leu His Ile Lys Gln Asp
35              40                  45                  50

Glu Arg Val Thr Met Gly Gln Asn Gly Asn Leu Tyr Phe Ala Asn Val Leu
            55                  60                  65

Thr Ser Asp Asn His Ser Asp Tyr Ile Cys His Ala His Phe Pro Gly Thr
70                  75                  80                  85

Arg Thr Ile Ile Gln Lys Glu Pro Ile Asp Leu Arg Val Lys Ala Thr Asn
                90                  95                  100

Ser Met Ile Asp
        105
```

(2) INFORMATION FOR SEQ ID NO: 23:

(i) SEQUENCE CHARACTERISTICS:

(A) LENGTH: 96
        (B) TYPE: amino acid
        (C) STRANDEDNESS: single
        (D) TOPOLOGY: linear (ii) MOLECULE TYPE: amino acids (iii) HYPOTHETICAL: irrelevant (iv) ANTI-SENSE: no (vi) ORIGINAL SOURCE:
        (A) ORGANISM: Homo Sapiens
        (B) INDIVIDUAL ISOLATE: 17-18 week fetus (vii) IMMEDIATE SOURCE:
        (A) LIBRARY: Stratagene cDNA Library 936206
        (B) CLONE: synthesis of 4 clones (x) PUBLICATION INFORMATION:
        (A) AUTHORS: Hlavin, Mary Louise
              Lemmon, Vance
        (B) TITLE:    Molecular structure and functional
              testing of human L1CAM: an interspecies
              comparison.
        (C) JOURNAL: GENOMICS
        (D) VOLUME:   11
        (E) ISSUE:
        (F) PAGES:    416-423
        (G) DATE:     1991

(xi) SEQUENCE DESCRIPTION: SEQ ID NO: 23:

Arg Lys Pro Arg Leu Leu Phe Pro Thr Asn Ser Ser Ser His Leu Val Ala
 1               5                  10                  15

Leu Gln Gly Gln Pro Leu Val Leu Glu Cys Ile Ala Glu Gly Phe Pro Thr
            20                  25                  30

Pro Thr Ile Lys Trp Leu Arg Pro Ser Gly Pro Met Pro Ala Asp Arg Val
35                  40                  45                  50

Thr Tyr Gln Asn His Asn Lys Thr Leu Gln Leu Leu Lys Val Gly Glu Glu
            55                  60                  65

Asp Asp Gly Glu Tyr Arg Cys Leu Ala Glu Asn Ser Leu Gly Ser Ala Arg
70                  75                  80                  85

His Ala Tyr Tyr Val Thr Val Glu Ala Ala Pro
            90                  95

(2) INFORMATION FOR SEQ ID NO: 24:

(i) SEQUENCE CHARACTERISTICS:
        (A) LENGTH: 92
        (B) TYPE: amino acid
        (C) STRANDEDNESS: single
        (D) TOPOLOGY: linear (ii) MOLECULE TYPE: amino acids (iii) HYPOTHETICAL: irrelevant (iv) ANTI-SENSE: no (vi) ORIGINAL SOURCE:
        (A) ORGANISM: Homo Sapiens
        (B) INDIVIDUAL ISOLATE: 17-18 week fetus (vii) IMMEDIATE SOURCE:
        (A) LIBRARY: Stratagene cDNA Library 936206
        (B) CLONE: synthesis of 4 clones (x) PUBLICATION INFORMATION:
        (A) AUTHORS: Hlavin, Mary Louise
              Lemmon, Vance
        (B) TITLE:    Molecular structure and functional
              testing of human L1CAM: an interspecies
              comparison.

(C) JOURNAL: GENOMICS
        (D) VOLUME: 11
        (E) ISSUE:
        (F) PAGES: 416-423
        (G) DATE: 1991

(xi) SEQUENCE DESCRIPTION: SEQ ID NO: 24:

Tyr Trp Leu His Lys Pro Gln Ser His Leu Tyr Gly Pro Gly Glu Thr Ala
1               5                   10                  15

Arg Leu Asp Cys Gln Val Gln Gly Arg Pro Gln Pro Glu Val Thr Trp Arg
            20                  25                  30

Ile Asn Gly Ile Pro Val Glu Glu Leu Ala Lys Asp Gln Lys Tyr Arg Ile
35                      40                  45                  50

Gln Arg Gly Ala Leu Ile Leu Ser Asn Val Gln Pro Ser Asp Thr Met Val
                55                  60                  65

Thr Gln Cys Glu Ala Arg Asn Arg His Gly Leu Leu Leu Ala Asn Ala Tyr
70                      75                  80                  85

Ile Tyr Val Val Gln Leu Pro
                90

(2) INFORMATION FOR SEQ ID NO: 25:

(i) SEQUENCE CHARACTERISTICS:
        (A) LENGTH: 93
        (B) TYPE: amino acid
        (C) STRANDEDNESS: single
        (D) TOPOLOGY: linear (ii) MOLECULE TYPE: amino acids (iii) HYPOTHETICAL: irrelevant (iv) ANTI-SENSE: no (vi) ORIGINAL SOURCE:
        (A) ORGANISM: Homo Sapiens
        (B) INDIVIDUAL ISOLATE: 17-18 week fetus (vii) IMMEDIATE SOURCE:
        (A) LIBRARY: Stratagene cDNA Library 936206
        (B) CLONE: synthesis of 4 clones (x) PUBLICATION INFORMATION:
        (A) AUTHORS: Hlavin, Mary Louise
            Lemmon, Vance
        (B) TITLE: Molecular structure and functional
            testing of human L1CAM: an interspecies
            comparison.
        (C) JOURNAL: GENOMICS
        (D) VOLUME: 11
        (E) ISSUE:
        (F) PAGES: 416-423
        (G) DATE: 1991

(xi) SEQUENCE DESCRIPTION: SEQ ID NO: 25:

Ala Lys Ile Leu Thr Ala Asp Asn Gln Thr Tyr Met Ala Val Gln Gly Ser
1               5                   10                  15

Thr Ala Tyr Leu Leu Cys Lys Ala Phe Gly Ala Pro Val Pro Ser Val Gln
            20                  25                  30

Trp Leu Asp Glu Asp Gly Thr Thr Val Leu Gln Asp Glu Arg Phe Phe Pro
35                      40                  45                  50

Tyr Ala Asn Gly Thr Leu Gly Ile Arg Asp Leu Gln Ala Asn Asp Thr Gly
                55                  60                  65

Arg Tyr Phe Cys Leu Ala Ala Asn Asp Gln Asn Asn Val Thr Ile Met Ala
70                      75                  80                  85

Asn Leu Lys Val Lys Asp Ala Thr
                90

(2) INFORMATION FOR SEQ ID NO: 26:

(i) SEQUENCE CHARACTERISTICS:
        (A) LENGTH: 96
        (B) TYPE: amino acid
        (C) STRANDEDNESS: single
        (D) TOPOLOGY: linear (ii) MOLECULE TYPE: amino acids (iii) HYPOTHETICAL: irrelevant (iv) ANTI-SENSE: no (vi) ORIGINAL SOURCE:
        (A) ORGANISM: Homo Sapiens
        (B) INDIVIDUAL ISOLATE: 17-18 week fetus (vii) IMMEDIATE SOURCE:
        (A) LIBRARY: Stratagene cDNA Library 936206
        (B) CLONE: synthesis of 4 clones (x) PUBLICATION INFORMATION:
        (A) AUTHORS: Hlavin, Mary Louise
            Lemmon, Vance
        (B) TITLE: Molecular structure and functional
            testing of human L1CAM: an interspecies
            comparison.
        (C) JOURNAL: GENOMICS
        (D) VOLUME: 11
        (E) ISSUE:
        (F) PAGES: 416-423
        (G) DATE: 1991

(xi) SEQUENCE DESCRIPTION: SEQ ID NO: 26:

Gln Ile Thr Gln Gly Pro Arg Ser Thr Ile Glu Lys Lys Gly Ser Arg Val
1               5                   10                  15

Thr Phe Thr Cys Gln Ala Ser Phe Asp Pro Ser Leu Gln Pro Ser Ile Thr
            20                  25                  30

Trp Arg Gly Asp Gly Arg Asp Leu Gln Glu Leu Gly Asp Ser Asp Lys Tyr
35              40                  45                  50

Phe Ile Glu Asp Gly Arg Leu Val Ile His Ser Leu Asp Tyr Ser Asp Gln
                55                  60                  65

Gly Asn Tyr Ser Cys Val Ala Ser Thr Glu Leu Asp Val Val Glu Ser Arg
        70                  75                  80                  85

Ala Gln Leu Leu Val Val Gly Ser Pro Gly Pro
                90                  95

(2) INFORMATION FOR SEQ ID NO: 27:

(i) SEQUENCE CHARACTERISTICS:
        (A) LENGTH: 101
        (B) TYPE: amino acid
        (C) STRANDEDNESS: single
        (D) TOPOLOGY: linear (ii) MOLECULE TYPE: amino acids (iii) HYPOTHETICAL: irrelevant (iv) ANTI-SENSE: no (vi) ORIGINAL SOURCE:
        (A) ORGANISM: Homo Sapiens
        (B) INDIVIDUAL ISOLATE: 17-18 week fetus (vii) IMMEDIATE SOURCE:
        (A) LIBRARY: Stratagene cDNA Library 936206
        (B) CLONE: synthesis of 4 clones (x) PUBLICATION INFORMATION:

(A) AUTHORS: Hlavin, Mary Louise
    Lemmon, Vance
(B) TITLE: Molecular structure and functional
    testing of human L1CAM: an interspecies
    comparison.
(C) JOURNAL: GENOMICS
(D) VOLUME: 11
(E) ISSUE:
(F) PAGES: 416-423
(G) DATE: 1991

(xi) SEQUENCE DESCRIPTION: SEQ ID NO: 27:

```
Val Pro Arg Leu Val Leu Ser Asp Leu His Leu Leu Thr Gln Ser Gln Val
 1               5                  10                  15

Arg Val Ser Trp Ser Pro Ala Glu Asp His Asn Ala Pro Ile Glu Lys Tyr
            20                  25                  30

Asp Ile Glu Phe Glu Asp Lys Glu Met Ala Pro Glu Lys Trp Tyr Ser Leu
35                  40                  45                  50

Gly Lys Val Pro Gly Asn Gln Thr Ser Thr Thr Leu Lys Leu Ser Pro Tyr
                55                  60                  65

Val His Tyr Thr Phe Arg Val Thr Ala Ile Asn Lys Tyr Gly Pro Gly Glu
        70                  75                  80                  85

Pro Ser Pro Val Ser Glu Thr Val Val Thr Pro Glu Ala Ala Pro Glu
                    90                  95                  100
```

(2) INFORMATION FOR SEQ ID NO: 28:

(i) SEQUENCE CHARACTERISTICS:
        (A) LENGTH: 96
        (B) TYPE: amino acid
        (C) STRANDEDNESS: single
        (D) TOPOLOGY: linear (ii) MOLECULE TYPE: amino acids (iii) HYPOTHETICAL: irrelevant (iv) ANTI-SENSE: no (vi) ORIGINAL SOURCE:
        (A) ORGANISM: Homo Sapiens
        (B) INDIVIDUAL ISOLATE: 17-18 week fetus (vii) IMMEDIATE SOURCE:
        (A) LIBRARY: Stratagene cDNA Library 936206
        (B) CLONE: synthesis of 4 clones (x) PUBLICATION INFORMATION:
        (A) AUTHORS: Hlavin, Mary Louise
            Lemmon, Vance
        (B) TITLE: Molecular structure and functional
            testing of human L1CAM: an interspecies
            comparison.
        (C) JOURNAL: GENOMICS
        (D) VOLUME: 11
        (E) ISSUE:
        (F) PAGES: 416-423
        (G) DATE: 1991

(xi) SEQUENCE DESCRIPTION: SEQ ID NO: 28:

```
Lys Asn Pro Val Asp Val Lys Gly Glu Gly Asn Glu Thr Thr Asn Met Val
 1               5                  10                  15

Ile Thr Trp Lys Pro Leu Arg Trp Met Asp Trp Asn Ala Pro Gln Val Gln
            20                  25                  30

Tyr Arg Val Gln Trp Arg Pro Gln Gly Thr Arg Gly Pro Trp Gln Glu Gln
35                  40                  45                  50

Ile Val Ser Asp Pro Phe Leu Val Val Ser Asn Thr Ser Thr Phe Val Pro
                55                  60                  65
```

```
Tyr Glu Ile Lys Val Gln Ala Val Asn Ser Gln Gly Lys Gly Pro Glu Pro
     70                  75                  80                  85

Gln Val Thr Ile Gly Tyr Ser Gly Glu Asp Tyr
                 90                  95

(2) INFORMATION FOR SEQ ID NO: 29:

(i) SEQUENCE CHARACTERISTICS:
        (A) LENGTH:  106
        (B) TYPE:  amino acid
        (C) STRANDEDNESS:  single
        (D) TOPOLOGY:  linear (ii) MOLECULE TYPE:  amino acids (iii) HYPOTHETICAL:  irrelevant (iv) ANTI-SENSE:  no (vi) ORIGINAL SOURCE:
        (A) ORGANISM:  Homo Sapiens
        (B) INDIVIDUAL ISOLATE:  17-18 week fetus (vii) IMMEDIATE SOURCE:
        (A) LIBRARY:  Stratagene cDNA Library 936206
        (B) CLONE:  synthesis of 4 clones (x) PUBLICATION INFORMATION:
        (A) AUTHORS:  Hlavin, Mary Louise
            Lemmon, Vance
        (B) TITLE:    Molecular structure and functional
            testing of human L1CAM: an interspecies
            comparison.
        (C) JOURNAL:  GENOMICS
        (D) VOLUME:   11
        (E) ISSUE:
        (F) PAGES:    416-423
        (G) DATE:     1991

(xi) SEQUENCE DESCRIPTION:  SEQ ID NO: 29:

Pro Gln Ala Ile Pro Glu Leu Glu Gly Ile Glu Ile Leu Asn Ser Ser Ala
 1               5                  10                  15

Val Leu Val Lys Trp Arg Pro Val Asp Leu Ala Gln Val Lys Gly His Leu
         20                  25                  30

Arg Gly Tyr Asn Val Thr Tyr Trp Arg Glu Gly Ser Gln Arg Lys His Ser
35                   40                  45                  50

Lys Arg His Ile His Lys Asp His Val Val Pro Ala Asn Thr Thr Ser
             55                  60                  65

Val Ile Leu Ser Gly Leu Arg Pro Tyr Ser Ser Tyr His Leu Glu Val Gln
     70                  75                  80                  85

Ala Phe Asn Gly Arg Gly Ser Gly Pro Ala Ser Glu Phe Thr Phe Ser Thr
                 90                  95                 100

Pro Glu Gly Val
        105

(2) INFORMATION FOR SEQ ID NO: 30:

(i) SEQUENCE CHARACTERISTICS:
        (A) LENGTH:  97
        (B) TYPE:  amino acid
        (C) STRANDEDNESS:  single
        (D) TOPOLOGY:  linear (ii) MOLECULE TYPE:  amino acids (iii) HYPOTHETICAL:  irrelevant (iv) ANTI-SENSE:  no (vi) ORIGINAL SOURCE:
```

(A) ORGANISM: Homo Sapiens
(B) INDIVIDUAL ISOLATE: 17-18 week fetus (vii) IMMEDIATE SOURCE:
(A) LIBRARY: Stratagene cDNA Library 936206
(B) CLONE: synthesis of 4 clones (x) PUBLICATION INFORMATION:
(A) AUTHORS: Hlavin, Mary Louise
    Lemmon, Vance
(B) TITLE: Molecular structure and functional
    testing of human L1CAM: an interspecies
    comparison.
(C) JOURNAL: GENOMICS
(D) VOLUME: 11
(E) ISSUE:
(F) PAGES: 416-423
(G) DATE: 1991

(xi) SEQUENCE DESCRIPTION: SEQ ID NO: 30:

```
Pro Gly His Pro Glu Ala Leu His Leu Glu Cys Gln Ser Asn Thr Ser Leu
1               5                   10                  15

Leu Leu Arg Trp Gln Pro Pro Leu Ser His Asn Gly Val Leu Thr Gly Tyr
            20                  25                  30

Val Leu Ser Tyr His Pro Leu Asp Glu Gly Lys Gly Gln Leu Ser Phe
35                  40                  45                  50

Asn Leu Arg Asp Pro Glu Leu Arg Thr His Asn Leu Thr Asp Leu Ser Pro
                55                  60                  65

His Leu Arg Tyr Arg Phe Gln Leu Gln Ala Thr Thr Lys Glu Gly Pro Gly
        70                  75                  80                  85

Glu Ala Ile Val Arg Glu Gly Gly Thr Met Ala Leu
                90                  95
```

(2) INFORMATION FOR SEQ ID NO: 31:

(i) SEQUENCE CHARACTERISTICS:
(A) LENGTH: 99
(B) TYPE: amino acid
(C) STRANDEDNESS: single
(D) TOPOLOGY: linear (ii) MOLECULE TYPE: amino acids (iii) HYPOTHETICAL: irrelevant (iv) ANTI-SENSE: no (vi) ORIGINAL SOURCE:
(A) ORGANISM: Homo Sapiens
(B) INDIVIDUAL ISOLATE: 17-18 week fetus (vii) IMMEDIATE SOURCE:
(A) LIBRARY: Stratagene cDNA Library 936206
(B) CLONE: synthesis of 4 clones (x) PUBLICATION INFORMATION:
(A) AUTHORS: Hlavin, Mary Louise
    Lemmon, Vance
(B) TITLE: Molecular structure and functional
    testing of human L1CAM: an interspecies
    comparison.
(C) JOURNAL: GENOMICS
(D) VOLUME: 11
(E) ISSUE:
(F) PAGES: 416-423
(G) DATE: 1991

(xi) SEQUENCE DESCRIPTION: SEQ ID NO: 31:

```
Ser Gly Ile Ser Asp Phe Gly Asn Ile Ser Ala Thr Ala Gly Glu Asn Tyr
1               5                   10                  15

Ser Val Val Ser Trp Val Pro Lys Glu Gly Gln Cys Asn Phe Arg Phe His
```

```
                    20                  25                  30
Ile Leu Phe Lys Ala Leu Gly Glu Glu Lys Gly Ala Ser Leu Ser Pro
 35                  40                  45                  50

Gln Tyr Val Ser Tyr Asn Gln Ser Ser Tyr Thr Gln Trp Asp Leu Gln Pro
                 55                  60                  65

Asp Thr Asp Tyr Glu Ile His Leu Phe Lys Glu Arg Met Phe Arg His Gln
             70                  75                  80                  85

Met Ala Val Lys Thr Asn Gly Thr Gly Arg Val Arg Leu Pro
                 90                  95
```

(2) INFORMATION FOR SEQ ID NO: 32:

(i) SEQUENCE CHARACTERISTICS:
        (A) LENGTH: 144
        (B) TYPE: amino acid
        (C) STRANDEDNESS: single
        (D) TOPOLOGY: linear (ii) MOLECULE TYPE: amino acids (iii) HYPOTHETICAL: irrelevant (iv) ANTI-SENSE: no (vi) ORIGINAL SOURCE:
        (A) ORGANISM: Homo Sapiens
        (B) INDIVIDUAL ISOLATE: 17-18 week fetus (vii) IMMEDIATE SOURCE:
        (A) LIBRARY: Stratagene cDNA Library 936206
        (B) CLONE: synthesis of 4 clones (x) PUBLICATION INFORMATION:
        (A) AUTHORS: Hlavin, Mary Louise
            Lemmon, Vance
        (B) TITLE: Molecular structure and functional testing of human L1CAM: an interspecies comparison.
        (C) JOURNAL: GENOMICS
        (D) VOLUME: 11
        (E) ISSUE:
        (F) PAGES: 416-423
        (G) DATE: 1991

(xi) SEQUENCE DESCRIPTION: SEQ ID NO: 32:

```
Pro Ala Gly Phe Ala Thr Glu Gly Trp Phe Ile Gly Phe Val Ser Ala Ile
 1               5                  10                  15

Ile Leu Leu Leu Leu Val Leu Leu Ile Leu Cys Phe Ile Lys Arg Ser Lys
                 20                  25                  30

Gly Gly Lys Tyr Ser Val Lys Asp Lys Glu Asp Thr Gln Val Asp Ser Glu
 35                  40                  45                  50

Ala Arg Pro Met Lys Asp Glu Thr Phe Gly Glu Tyr Arg Ser Leu Glu Ser
                 55                  60                  65

Asp Asn Glu Glu Lys Ala Phe Gly Ser Ser Gln Pro Ser Leu Asn Gly Asp
 70                  75                  80                  85

Ile Lys Pro Leu Gly Ser Asp Asp Ser Leu Ala Asp Tyr Gly Gly Ser Val
                 90                  95                 100

Asp Val Gln Phe Asn Glu Asp Gly Ser Phe Ile Gly Gln Tyr Ser Gly Lys
                105                 110                 115

Lys Glu Lys Glu Ala Ala Gly Gly Asn Asp Ser Ser Gly Ala Thr Ser Pro
120                 125                 130                 135

Ile Asn Pro Ala Val Ala Leu Glu
                140
```

(2) INFORMATION FOR SEQ ID NO: 33:

(i) SEQUENCE CHARACTERISTICS:
        (A) LENGTH: 90
        (B) TYPE: amino acid
        (C) STRANDEDNESS: single
        (D) TOPOLOGY: linear (ii) MOLECULE TYPE: amino acids (iii) HYPOTHETICAL: irrelevant (iv) ANTI-SENSE: no (vi) ORIGINAL SOURCE:
        (A) ORGANISM: CHICKEN
        (B) INDIVIDUAL ISOLATE: e9-e14 embryos brains, adult brains (vii) IMMEDIATE SOURCE:
        (A) LIBRARY: many lambda GT11 cDNA and genomic libraries
        (B) CLONE: synthesis of 14 clones (x) PUBLICATION INFORMATION:
        (A) AUTHORS: Burgoon, M.P.
            Grumet, M.
            Mauro, V.
            Edelman, G.M.
            Cunningham, B.A.
        (B) TITLE: Structure of the chicken neuron-
            glial cell adhesion molecule, Ng-CAM:
            Origin of the polypeptides and
            relation to the Ig superfamily.
        (C) JOURNAL: J. Cell Biol.
        (D) VOLUME: 112
        (E) ISSUE:
        (F) PAGES: 1017-1029
        (G) DATE: 1991

(xi) SEQUENCE DESCRIPTION: SEQ ID NO: 33:

Glu Leu Thr Glu Glu Pro Pro Glu Gln Leu Val Val Phe Pro Ser Asp Asp
 1               5                  10                  15

Ile Val Leu Lys Cys Val Ala Thr Gly Asn Pro Pro Val Gln Tyr Arg Trp
            20                  25                  30

Ser Arg Glu Ile Ser Pro Ser Ser Pro Arg Ser Thr Gly Gly Ser Arg Trp
35                  40                  45                  50

Ser Pro Asp Arg His Leu Val Ile Asn Ala Thr Leu Ala Ala Arg Leu Gln
                55                  60                  65

Gly Arg Phe Arg Cys Phe Ala Thr Asn Ala Leu Gly Thr Ala Val Ser Pro
    70                  75                  80                  85

Glu Ala Asn Val Ile
                90

(2) INFORMATION FOR SEQ ID NO: 34:

(i) SEQUENCE CHARACTERISTICS:
        (A) LENGTH: 106
        (B) TYPE: amino acid
        (C) STRANDEDNESS: single
        (D) TOPOLOGY: linear (ii) MOLECULE TYPE: amino acids (iii) HYPOTHETICAL: irrelevant (iv) ANTI-SENSE: no (vi) ORIGINAL SOURCE:
        (A) ORGANISM: CHICKEN
        (B) INDIVIDUAL ISOLATE: e9-e14 embryos brains, adult brains (vii) IMMEDIATE SOURCE:
        (A) LIBRARY: many lambda GT11 cDNA and genomic libraries
        (B) CLONE: synthesis of 14 clones

```
    (x) PUBLICATION INFORMATION:
        (A) AUTHORS:  Burgoon, M.P.
                      Grumet, M.
                      Mauro, V.
                      Edelman, G.M.
                      Cunningham, B.A.
        (B) TITLE:    Structure of the chicken neuron-
                      glial cell adhesion molecule, Ng-CAM:
                      Origin of the polypeptides and
                      relation to the Ig superfamily.
        (C) JOURNAL:  J. Cell Biol.
        (D) VOLUME:   112
        (E) ISSUE:
        (F) PAGES:    1017-1029
        (G) DATE:     1991

(xi) SEQUENCE DESCRIPTION: SEQ ID NO: 34:

Ala Glu Asn Thr Pro Gln Trp Pro Lys Lys Lys Val Thr Pro Val Glu Val
 1               5                  10                  15

Glu Glu Gly Asp Pro Val Val Leu Pro Cys Asp Pro Pro Glu Ser Ala Val
            20                  25                  30

Pro Pro Lys Ile Tyr Trp Leu Asn Ser Asp Ile Val His Ile Ala Gln Asp
35              40                  45                  50

Glu Arg Val Ser Met Gly Gln Asp Gly Asn Leu Tyr Phe Ser Asn Ala Met
                55                  60                  65

Val Gly Asp Ser His Pro Asp Tyr Ile Cys His Ala His Phe Leu Gly Pro
70                  75                  80                      85

Arg Thr Ile Ile Gln Lys Glu Pro Leu Asp Leu Arg Val Ala Pro Ser Asn
                90                  95                  100

Ala Val Arg Ser
        105

(2) INFORMATION FOR SEQ ID NO: 35:

(i) SEQUENCE CHARACTERISTICS:
        (A) LENGTH: 94
        (B) TYPE:   amino acid
        (C) STRANDEDNESS:  single
        (D) TOPOLOGY:  linear (ii) MOLECULE TYPE:  amino acids (iii) HYPOTHETICAL:  irrelevant (iv) ANTI-SENSE:  no (vi) ORIGINAL SOURCE:
        (A) ORGANISM:  CHICKEN
        (B) INDIVIDUAL ISOLATE:  e9-e14 embryos brains, adult brains (vii) IMMEDIATE SOURCE:
        (A) LIBRARY:  many lambda GT11 cDNA and genomic libraries
        (B) CLONE:    synthesis of 14 clones (x) PUBLICATION INFORMATION:
        (A) AUTHORS:  Burgoon, M.P.
                      Grumet, M.
                      Mauro, V.
                      Edelman, G.M.
                      Cunningham, B.A.
        (B) TITLE:    Structure of the chicken neuron-
                      glial cell adhesion molecule, Ng-CAM:
                      Origin of the polypeptides and
                      relation to the Ig superfamily.
        (C) JOURNAL:  J. Cell Biol.
        (D) VOLUME:   112
        (E) ISSUE:
        (F) PAGES:    1017-1029
        (G) DATE:     1991

(xi) SEQUENCE DESCRIPTION: SEQ ID NO: 35:
```

```
Arg Arg Pro Arg Leu Leu Leu Pro Arg Asp Pro Gln Thr Thr Thr Ile Ala
 1               5                  10                 15

Leu Arg Gly Gly Ser Val Val Leu Glu Cys Ile Ala Glu Gly Leu Pro Thr
         20                  25                  30

Pro Trp Val Arg Trp Arg Arg Leu Asn Gly Pro Leu Leu Pro Gly Gly Val
 35              40                  45                 50

Gly Asn Phe Asn Lys Thr Leu Arg Leu Trp Gly Val Thr Glu Ser Asp Asp
             55                  60                  65

Gly Glu Tyr Glu Cys Val Ala Glu Asn Gly Arg Gly Thr Ala Arg Gly Thr
         70                  75                  80              85

His Ser Val Thr Val Glu Ala Ala Pro
                 90
```

(2) INFORMATION FOR SEQ ID NO: 36:

(i) SEQUENCE CHARACTERISTICS:
        (A) LENGTH: 91
        (B) TYPE: amino acid
        (C) STRANDEDNESS: single
        (D) TOPOLOGY: linear (ii) MOLECULE TYPE: amino acids (iii) HYPOTHETICAL: irrelevant (iv) ANTI-SENSE: no (vi) ORIGINAL SOURCE:
        (A) ORGANISM: CHICKEN
        (B) INDIVIDUAL ISOLATE: e9-e14 embryos brains, adult brains (vii) IMMEDIATE SOURCE:
        (A) LIBRARY: many lambda GT11 cDNA and genomic libraries
        (B) CLONE: synthesis of 14 clones (x) PUBLICATION INFORMATION:
        (A) AUTHORS: Burgoon, M.P.
            Grumet, M.
            Mauro, V.
            Edelman, G.M.
            Cunningham, B.A.
        (B) TITLE: Structure of the chicken neuron-
            glial cell adhesion molecule, Ng-CAM:
            Origin of the polypeptides and
            relation to the Ig superfamily.
        (C) JOURNAL: J. Cell Biol.
        (D) VOLUME: 112
        (E) ISSUE:
        (F) PAGES: 1017-1029
        (G) DATE: 1991

(xi) SEQUENCE DESCRIPTION: SEQ ID NO: 36:

```
Tyr Trp Val Arg Arg Pro Gln Ser Gly Val Phe Gly Pro Gly Glu Thr Ala
 1               5                  10                 15

Arg Leu Asp Cys Glu Val Gly Gly Lys Pro Arg Pro Gln Ile Gln Trp Ser
         20                  25                  30

Ile Asn Gly Val Pro Ile Glu Ala Ala Gly Ala Glu Arg Arg Trp Leu Arg
 35              40                  45                 50

Gly Gly Ala Leu Val Leu Pro Glu Leu Arg Pro Asn Asp Ser Ala Val Leu
             55                  60                  65

Gln Cys Glu Ala Arg Asn Arg His Gly Pro Leu Leu Ala Asn Ala Phe Leu
         70                  75                  80              85

His Val Val Glu Leu Pro
                 90
```

(2) INFORMATION FOR SEQ ID NO: 37:

```
    (i) SEQUENCE CHARACTERISTICS:
        (A) LENGTH: 93
        (B) TYPE: amino acid
        (C) STRANDEDNESS: single
        (D) TOPOLOGY: linear (ii) MOLECULE TYPE: amino acids (iii) HYPOTHETICAL: irrelevant (iv) ANTI-SENSE: no (vi) ORIGINAL SOURCE:
        (A) ORGANISM: CHICKEN
        (B) INDIVIDUAL ISOLATE: e9-e14 embryos brains, adult brains (vii) IMMEDIATE SOURCE:
        (A) LIBRARY: many lambda GT11 cDNA and genomic libraries
        (B) CLONE: synthesis of 14 clones (x) PUBLICATION INFORMATION:
        (A) AUTHORS: Burgoon, M.P.
            Grumet, M.
            Mauro, V.
            Edelman, G.M.
            Cunningham, B.A.
        (B) TITLE:   Structure of the chicken neuron-
            glial cell adhesion molecule, Ng-CAM:
            Origin of the polypeptides and
            relation to the Ig superfamily.
        (C) JOURNAL: J. Cell Biol.
        (D) VOLUME:  112
        (E) ISSUE:
        (F) PAGES:   1017-1029
        (G) DATE:    1991

(xi) SEQUENCE DESCRIPTION: SEQ ID NO: 37:

Leu Arg Met Leu Thr Ala Asp Glu Gln Arg Tyr Glu Val Val Glu Asn Gln
 1               5                  10                  15

Thr Val Phe Leu His Cys Arg Thr Phe Gly Ala Pro Ala Pro Asn Val Glu
            20                  25                  30

Trp Leu Thr Pro Thr Leu Glu Pro Ala Leu Gln Asp Asp Arg Ser Phe Val
35                  40                  45                  50

Phe Thr Asn Gly Ser Leu Arg Val Ser Ala Val Arg Gly Gly Asp Gly Gly
                55                  60                  65

Val Tyr Thr Cys Met Ala Gln Asn Ala His Ser Asn Gly Ser Leu Thr Ala
        70                  75                  80                  85

Leu Leu Glu Val Arg Ala Pro Thr
                90

(2) INFORMATION FOR SEQ ID NO: 38:

(i) SEQUENCE CHARACTERISTICS:
        (A) LENGTH: 92
        (B) TYPE: amino acid
        (C) STRANDEDNESS: single
        (D) TOPOLOGY: linear (ii) MOLECULE TYPE: amino acids (iii) HYPOTHETICAL: irrelevant (iv) ANTI-SENSE: no (vi) ORIGINAL SOURCE:
        (A) ORGANISM: CHICKEN
        (B) INDIVIDUAL ISOLATE: e9-e14 embryos brains, adult brains (vii) IMMEDIATE SOURCE:
        (A) LIBRARY: many lambda GT11 cDNA and genomic libraries
        (B) CLONE: synthesis of 14 clones (x) PUBLICATION INFORMATION:
```

(A) AUTHORS: Burgoon, M.P.
        Grumet, M.
        Mauro, V.
        Edelman, G.M.
        Cunningham, B.A.
    (B) TITLE: Structure of the chicken neuron-
        glial cell adhesion molecule, Ng-CAM:
        Origin of the polypeptides and
        relation to the Ig superfamily.
    (C) JOURNAL: J. Cell Biol.
    (D) VOLUME: 112
    (E) ISSUE:
    (F) PAGES: 1017-1029
    (G) DATE: 1991

(xi) SEQUENCE DESCRIPTION: SEQ ID NO: 38:

Arg Ile Ser Ala Pro Pro Arg Ser Ala Thr Ala Lys Lys Gly Glu Thr Val
1               5                   10                  15

Thr Phe His Cys Gly Ala Thr Phe Asp Pro Ala Val Thr Pro Gly Glu Leu
            20                  25                  30

Arg Trp Leu Arg Gly Gly Gln Pro Leu Pro Asp Asp Pro Arg Tyr Ser Val
35                  40                  45                  50

Ala Ala Glu Met Thr Val Ser Asn Val Asp Tyr Gly Asp Glu Gly Thr Ile
                55                  60                  65

Gln Cys Arg Ala Ser Thr Pro Leu Asp Ser Ala Glu Ala Glu Ala Gln Leu
70                  75                  80                      85

Arg Val Val Gly Arg Pro Pro
                90

(2) INFORMATION FOR SEQ ID NO: 39:

(i) SEQUENCE CHARACTERISTICS:
        (A) LENGTH: 98
        (B) TYPE: amino acid
        (C) STRANDEDNESS: single
        (D) TOPOLOGY: linear (ii) MOLECULE TYPE: amino acids (iii) HYPOTHETICAL: irrelevant (iv) ANTI-SENSE: no (vi) ORIGINAL SOURCE:
        (A) ORGANISM: CHICKEN
        (B) INDIVIDUAL ISOLATE: e9-e14 embryos brains, adult brains (vii) IMMEDIATE SOURCE:
        (A) LIBRARY: many lambda GT11 cDNA and genomic libraries
        (B) CLONE: synthesis of 14 clones (x) PUBLICATION INFORMATION:
        (A) AUTHORS: Burgoon, M.P.
            Grumet, M.
            Mauro, V.
            Edelman, G.M.
            Cunningham, B.A.
        (B) TITLE: Structure of the chicken neuron-
            glial cell adhesion molecule, Ng-CAM:
            Origin of the polypeptides and
            relation to the Ig superfamily.
        (C) JOURNAL: J. Cell Biol.
        (D) VOLUME: 112
        (E) ISSUE:
        (F) PAGES: 1017-1029
        (G) DATE: 1991

(xi) SEQUENCE DESCRIPTION: SEQ ID NO: 39:

Ser Arg Asp Leu Gln Val Met Glu Val Asp Glu His Arg Val Arg Leu Ser
1               5                   10                  15

Trp Thr Pro Gly Asp Asp His Asn Ser Pro Ile Glu Lys Phe Val Val Glu

```
                  20                  25                  30
Glu Glu Glu Glu Arg Glu Asp Leu Gln Arg Gly Phe Gly Ala Ala Asp Val
 35                  40                  45                  50

Pro Gly Gln Pro Trp Thr Pro Pro Leu Pro Leu Ser Pro Tyr Gly Arg Phe
             55                  60                  65

Pro Phe Arg Val Val Ala Val Asn Ala Tyr Gly Arg Gly Glu His His Ala
         70                  75                  80                  85

Pro Ser Ala Pro Ile Glu Thr Pro Pro Ala Ala Pro Glu
                 90                  95
```

(2) INFORMATION FOR SEQ ID NO: 40:

(i) SEQUENCE CHARACTERISTICS:
        (A) LENGTH: 104
        (B) TYPE: amino acid
        (C) STRANDEDNESS: single
        (D) TOPOLOGY: linear (ii) MOLECULE TYPE: amino acids (iii) HYPOTHETICAL: irrelevant (iv) ANTI-SENSE: no (vi) ORIGINAL SOURCE:
        (A) ORGANISM: CHICKEN
        (B) INDIVIDUAL ISOLATE: e9-e14 embryos brains, adult brains (vii) IMMEDIATE SOURCE:
        (A) LIBRARY: many lambda GT11 cDNA and genomic libraries
        (B) CLONE: synthesis of 14 clones (x) PUBLICATION INFORMATION:
        (A) AUTHORS: Burgoon, M.P.
            Grumet, M.
            Mauro, V.
            Edelman, G.M.
            Cunningham, B.A.
        (B) TITLE: Structure of the chicken neuron-
            glial cell adhesion molecule, Ng-CAM:
            Origin of the polypeptides and
            relation to the Ig superfamily.
        (C) JOURNAL: J. Cell Biol.
        (D) VOLUME: 112
        (E) ISSUE:
        (F) PAGES: 1017-1029
        (G) DATE: 1991

(xi) SEQUENCE DESCRIPTION: SEQ ID NO: 40:

```
Arg Asn Pro Gly Gly Val His Gly Glu Gly Asn Glu Thr Gly Asn Leu Val
 1               5                  10                  15

Ile Thr Trp Glu Pro Leu Pro Pro Gln Ala Trp Asn Ala Pro Trp Ala Arg
             20                  25                  30

Tyr Arg Val Gln Trp Arg Pro Leu Glu Glu Pro Gly Gly Gly Gly Pro Ser
 35                  40                  45                  50

Gly Gly Phe Pro Trp Ala Glu Ser Thr Val Asp Ala Pro Val Val Val
             55                  60                  65

Gly Gly Leu Pro Pro Phe Ser Pro Phe Gln Ile Arg Val Gln Ala Val Asn
         70                  75                  80                  85

Gly Ala Gly Lys Gly Pro Glu Ala Thr Pro Gly Val Gly His Ser Gly Glu
                 90                  95                 100

Asp Leu
```

(2) INFORMATION FOR SEQ ID NO: 41:

(i) SEQUENCE CHARACTERISTICS:
        (A) LENGTH: 126

```
        (B) TYPE: amino acid
        (C) STRANDEDNESS: single
        (D) TOPOLOGY: linear (ii) MOLECULE TYPE: amino acids (iii) HYPOTHETICAL: irrelevant (iv) ANTI-SENSE: no (vi) ORIGINAL SOURCE:
        (A) ORGANISM: CHICKEN
        (B) INDIVIDUAL ISOLATE:  e9-e14 embryos brains, adult brains (vii) IMMEDIATE SOURCE:
        (A) LIBRARY:  many lambda GT11 cDNA and genomic libraries
        (B) CLONE:  synthesis of 14 clones (x) PUBLICATION INFORMATION:
        (A) AUTHORS:  Burgoon, M.P.
             Grumet, M.
             Mauro, V.
             Edelman, G.M.
             Cunningham, B.A.
        (B) TITLE:    Structure of the chicken neuron-
             glial cell adhesion molecule, Ng-CAM:
             Origin of the polypeptides and
             relation to the Ig superfamily.
        (C) JOURNAL:  J. Cell Biol.
        (D) VOLUME:   112
        (E) ISSUE:
        (F) PAGES:    1017-1029
        (G) DATE:     1991

(xi) SEQUENCE DESCRIPTION: SEQ ID NO: 41:

Pro Leu Val Tyr Pro Glu Asn Val Gly Val Glu Leu Leu Asn Ser Ser Thr
1               5                  10                  15

Val Arg Val Arg Trp Thr Leu Gly Gly Gly Pro Lys Glu Leu Arg Gly Arg
            20                  25                  30

Leu Arg Gly Phe Arg Val Leu Tyr Trp Arg Leu Gly Trp Val Gly Glu Arg
35                  40                  45                  50

Ser Arg Arg Gln Ala Pro Pro Asp Pro Pro Gln Ile Pro Gln Ser Pro Ala
            55                  60                  65

Glu Asp Pro Pro Pro Phe Pro Pro Val Ala Leu Thr Val Gly Gly Asp Ala
    70                  75                  80                  85

Arg Gly Ala Leu Leu Gly Gly Leu Arg Pro Trp Ser Arg Tyr Gln Leu Arg
            90                  95                  100

Val Leu Val Phe Asn Gly Arg Gly Asp Gly Pro Pro Ser Glu Pro Ile Ala
            105                 110                 115

Phe Glu Thr Pro Glu Gly Val
120                 125

(2) INFORMATION FOR SEQ ID NO: 42:

(i) SEQUENCE CHARACTERISTICS:
        (A) LENGTH: 98
        (B) TYPE: amino acid
        (C) STRANDEDNESS: single
        (D) TOPOLOGY: linear (ii) MOLECULE TYPE: amino acids (iii) HYPOTHETICAL: irrelevant (iv) ANTI-SENSE: no (vi) ORIGINAL SOURCE:
        (A) ORGANISM: CHICKEN
        (B) INDIVIDUAL ISOLATE:  e9-e14 embryos brains, adult brains (vii) IMMEDIATE SOURCE:
```

(A) LIBRARY:  many lambda GT11 cDNA and genomic libraries
(B) CLONE:    synthesis of 14 clones (x) PUBLICATION INFORMATION:
    (A) AUTHORS: Burgoon, M.P.
                 Grumet, M.
                 Mauro, V.
                 Edelman, G.M.
                 Cunningham, B.A.
    (B) TITLE:   Structure of the chicken neuron-
                 glial cell adhesion molecule, Ng-CAM:
                 Origin of the polypeptides and
                 relation to the Ig superfamily.
    (C) JOURNAL: J. Cell Biol.
    (D) VOLUME:  112
    (E) ISSUE:
    (F) PAGES:   1017-1029
    (G) DATE:    1991

(xi) SEQUENCE DESCRIPTION: SEQ ID NO: 42:

Pro Gly Pro Pro Glu Glu Leu Arg Val Glu Arg Leu Asp Asp Thr Ala Leu
1               5                   10                  15

Ser Val Val Glu Arg Arg Thr Phe Lys Arg Ser Ile Thr Gly Tyr Val Leu
        20                  25                  30

Arg Tyr Gln Gln Val Glu Pro Gly Ser Ala Leu Pro Gly Gly Ser Val Leu
35              40                  45                  50

Arg Asp Pro Gln Cys Asp Leu Arg Gly Leu Asn Ala Arg Ser Arg Tyr Arg
            55                  60                  65

Leu Ala Leu Pro Ser Thr Pro Arg Glu Arg Pro Ala Leu Gln Thr Val Gly
    70              75                  80                  85

Ser Thr Lys Pro Glu Pro Pro Ser Pro Leu Trp Ser Arg
                90                  95

(2) INFORMATION FOR SEQ ID NO: 43:

(i) SEQUENCE CHARACTERISTICS:
        (A) LENGTH: 93
        (B) TYPE: amino acid
        (C) STRANDEDNESS: single
        (D) TOPOLOGY: linear (ii) MOLECULE TYPE: amino acids (iii) HYPOTHETICAL: irrelevant (iv) ANTI-SENSE: no (vi) ORIGINAL SOURCE:
        (A) ORGANISM: CHICKEN
        (B) INDIVIDUAL ISOLATE: e9-e14 embryos brains, adult brains (vii) IMMEDIATE SOURCE:
        (A) LIBRARY:  many lambda GT11 cDNA and genomic libraries
        (B) CLONE:    synthesis of 14 clones (x) PUBLICATION INFORMATION:
        (A) AUTHORS: Burgoon, M.P.
                     Grumet, M.
                     Mauro, V.
                     Edelman, G.M.
                     Cunningham, B.A.
        (B) TITLE:   Structure of the chicken neuron-
                     glial cell adhesion molecule, Ng-CAM:
                     Origin of the polypeptides and
                     relation to the Ig superfamily.
        (C) JOURNAL: J. Cell Biol.
        (D) VOLUME:  112
        (E) ISSUE:
        (F) PAGES:   1017-1029
        (G) DATE:    1991

(xi) SEQUENCE DESCRIPTION: SEQ ID NO: 43:

```
Phe Gly Val Gly Gly Arg Gly Phe His Gly Ala Ala Val Glu Phe Gly
 1               5                  10                  15

Ala Ala Gln Glu Asp Asp Val Glu Phe Glu Val Gln Phe Met Asn Lys Ser
            20                  25                  30

Thr Asp Glu Pro Trp Arg Thr Ser Gly Arg Ala Asn Ser Ser Leu Arg Arg
35                  40                  45                  50

Tyr Arg Leu Glu Gly Leu Arg Pro Gly Thr Ala Tyr Arg Val Gln Phe Val
                55                  60                  65

Gly Arg Asn Arg Ser Gly Glu Asn Val Ala Phe Trp Glu Ser Glu Val Gln
        70                  75                  80                  85

Thr Asn Gly Thr Val Val Pro Gln
                    90
```

(2) INFORMATION FOR SEQ ID NO: 44:

(i) SEQUENCE CHARACTERISTICS:
        (A) LENGTH: 144
        (B) TYPE: amino acid
        (C) STRANDEDNESS: single
        (D) TOPOLOGY: linear (ii) MOLECULE TYPE: amino acids (iii) HYPOTHETICAL: irrelevant (iv) ANTI-SENSE: no (vi) ORIGINAL SOURCE:
        (A) ORGANISM: CHICKEN
        (B) INDIVIDUAL ISOLATE: e9-e14 embryos brains, adult brains (vii) IMMEDIATE SOURCE:
        (A) LIBRARY: many lambda GT11 cDNA and genomic libraries
        (B) CLONE: synthesis of 14 clones (x) PUBLICATION INFORMATION:
        (A) AUTHORS: Burgoon, M.P.
            Grumet, M.
            Mauro, V.
            Edelman, G.M.
            Cunningham, B.A.
        (B) TITLE: Structure of the chicken neuron-
            glial cell adhesion molecule, Ng-CAM:
            Origin of the polypeptides and
            relation to the Ig superfamily.
        (C) JOURNAL: J. Cell Biol.
        (D) VOLUME: 112
        (E) ISSUE:
        (F) PAGES: 1017-1029
        (G) DATE: 1991

(xi) SEQUENCE DESCRIPTION: SEQ ID NO: 44:

```
Pro Gly Gly Gly Val Cys Thr Lys Gly Trp Phe Ile Gly Phe Val Ser Ser
 1               5                  10                  15

Val Val Leu Leu Leu Leu Ile Leu Leu Ile Leu Cys Phe Ile Lys Arg Ser
            20                  25                  30

Lys Gly Gly Lys Tyr Ser Val Lys Asp Lys Glu Asp Thr Gln Val Asp Ser
35                  40                  45                  50

Glu Ala Arg Pro Met Lys Asp Glu Thr Phe Gly Glu Tyr Arg Ser Leu Glu
                55                  60                  65

Ser Glu Ala Glu Lys Gly Ser Ala Ser Gly Ser Gly Ala Gly Ser Gly Val
        70                  75                  80                  85

Gly Ser Pro Gly Arg Gly Pro Cys Ala Ala Gly Ser Glu Asp Ser Leu Ala
                90                  95                  100

Gly Tyr Gly Gly Ser Gly Asp Val Gln Phe Asn Glu Asp Gly Ser Phe Ile
                105                 110                 115
```

```
Gly Gln Tyr Arg Gly Pro Gly Ala Gly Pro Gly Ser Ser Gly Pro Ala Ser
120             125             130             135

Pro Cys Ala Gly Pro Pro Leu Asp
            140
```

NUCLEOTIDE SEQUENCE OF L1CAM

This is a continuation of application Ser. No. 07/953,493 filed on Sep. 28, 1992, now abandoned; which is a continuation-in-part of application Ser. No. 904,991 filed on Jun. 26, 1992, now abandoned.

FIELD OF THE INVENTION

The present invention is directed to the isolation and characterization of the entire coding sequence of human L1 cell adhesion molecule (L1CAM). In this regard, Applicants have cloned and sequenced four cDNAs, i.e. cDNA clone 3.1 (SEQ ID NO: 3), cDNA clone 4 (SEQ ID NO: 4), cDNA clone 17 (SEQ ID NO: 5), and cDNA clone C2 (SEQ ID NO: 6), encompassing the entire coding region of L1CAM (SEQ ID NO: 2). Collectively, the four cDNAs have a combined sequence (i.e. SEQ ID NO: 1) of 4529 bases in length.

The invention also relates to the nucleotide sequence (SEQ ID NO: 2) characterized by the present invention and the use of this sequence and the four cDNAs (SEQ ID NOS: 3–6) for studying the role of human L1 cell adhesion molecule (L1CAM) in normal and damaged neuronal tissue. In addition, the invention is directed to the isolated and purified polypeptide chain encoded by the nucleotide sequence of the invention.

BACKGROUND OF THE INVENTION

Cell adhesion molecules (abbreviated CAMs) are neuronal cell surface glycoproteins which help to mediate the cohesive interactions between developing or regenerating neurities. It is believed that proper adhesion of neuronal cells to each other and to their surrounding extracellular matrix is essential for maintaining and/or promoting growth of the neuronal cells.

A number of cell adhesion molecules have been isolated and identified, including neural cell adhesion molecule (N-CAM), nerve growth factor-inducible large external glycoprotein (NILE), neuron-glial CAM (Ng-CAM) and closely related proteins L1 (L1antigen). These integral membrane glycoproteins, or molecules closely related thereto, have been described by Applicants and others in the nervous system of several species.

Representative examples of such identification and description include L1cam in mouse, (Rathjen, F. G., Schachner, M., Immunocytological And Biochemical Characterization Of A New Neuronal Cell Surface Component (L1Antigen) Which Is Involved In Cell Adhesion. *EMBO J.* 3: 1–10 (1984)); NILE in rat, (McGuire, J. C., Greene, L. A., Furano, A. V., Nerve Growth Factor Stimulates Incorporation Of Fucose Or Glucosamine Into An External Glycoprotein In Cultures Rat PC12 Pheochromocytoma Cells. *Cell* 15: 357–365 (1978)); Ng-CAM/8D9/G4 in chick, (Grumet, M., Edelman, G. M., Neuron-Glia Cell Adhesion Molecule Interacts with Neurons and Astroglia via Different Binding Mechanisms. *J. Cell Biol.* 106: 487–503 (1988); and, Lemmon, V., McLoon, S., The Appearance Of An L1-Like Molecule In The Chick Primary Visual Pathway, *J. Neurosci.* 6: 2987–2994, (1986)); and Neuroglian in *Drosophila* (Bieber, A. J., Snow, P. M., Hortsch, M., Patel, N. H., Jacobs, J. R., Traquina, Z. R., Schilling, J., Goodman, C. S., Drosophila Neuroglian: A Member Of The Immunoglobulin Superfamily With Extensive Homology To The Vertebrate Neural Adhesion Molecule L1. *Cell* 59: 447–460 (1989)).

These molecules share similar biochemical properties, immunological crossreactivity, localization predominantly on axons of projection neurons, homology in nucleotide sequence as well as functional similarity.

The L1 cell adhesion molecule, which was first isolated and characterized in mouse (i.e. L1 cam) is a membrane-spanning glycoprotein that has sequence similarity with both fibronectin and the immunoglobulin superfamily. Specifically, L1 cell adhesion molecules possessing six extracellular Ig-like domains, three to five fibronectin (Fn) type III-like repeats, a transmembrane segment, and a small cytoplasmic region. The membrane-spanning region links the extensive extracellular domain to the substantial cytoplasmic domain.

Several lines of evidence suggest that the L1 cell adhesion molecule plays an important role in neuronal growth and fasciculation. First, it is expressed by subpopulations of neurons in the central nervous system and on nerons and Schwann cells in the peripheral nervous system. This expression is early on in developing (Martini, R., Schachner, M., Immunoelectron Microscopic Localization Of Neural Cell Adhesion Molecules (L1 , N-CAM, MAG) And Their Shared Carbohydrate Epitope And Myelin Basic Protein (MBP) In Developing Sciatic Nerve. *J. Cell Biol.* 103: 2439–2448 (1986)) and regenerating axons (Daniloff, J. K., Chuong, C. -M., Levi, G., Edelman, G. M., Differential Distribution Of Cell Adhesion Molecules During Histogenesis Of The Chick Nervous System. *J. Neurosci.* 6: 739–758 (1986); and, Martini, R., Schachner, M., Immunoelectron Microscopic Localization of Neural Cell Adhesion Molecules (L1, N-CAM, MAG) and Their Shared Carbohydrate Epitope and Myelin Basic Protein (MBP) in Developing Sciatic Nerve. *J. Cell Biol.* 103: 2439–2448 (1986)).

Secondly, since antibodies to L1 disrupt fascicle formation in vitro (Stallcup, W. B., Beasley, L., Involvement Of The Nerve Growth Factor-Inducible Large External Glycoprotein (NILE) In Neurite Fasciculation In Primary Cultures Of Rat Brain. *Proc. Natl. Acad. Sci. USA* 82: 1276–1280 (1985)) and in vivo (Landmesser, L., Dahm, L., Schultz, K., Rutishauser, U., Distinct Roles For Adhesion Molecules During Innervation Of Embryonic Chick Muscle. *Dev. Biol.* 130: 645–670 (1988)), L1 participates in axonal fasciculate formation.

Finally, it has been shown by Applicants and others that purified L1 is a potent substrate for neurite growth and development (Lagenaur, C., Lemmon, V., A L1-Like Molecule, The 8D9 Antigen, Is A Potent Substrate For Neurite Extension. *Proc. Natl. Acad. Sci. USA* 84: 7753–7757 (1987)).

Moreover, a number of observations are consistent with the existence of a L1 human homologue. Human tumors, especially neuroblastoma, demonstrate immunoreactivity to L1 antibodies (Mujoo, K., Spiro, R. C., Reisfeld, R. A., Characterization Of A Unique Glycoprotein Antigen Expressed On The Surface Of Human Neuroblastoma Cells. *J Biol. Chem.* 261: 10299–10305 (1986); and, Figarella-Branger, D. F., Durbec, P. L., Rougon, G. N., Differential Spectrum Of Expression Of Neural Cell Adhesion Molecule Isoforms And L1 Adhesion Molecules On Human Neuroectodermal Tumors. *Cancer Research* 50: 6364–6370 (1990)). In addition, Biochemical analysis of a glycoprotein isolated from human brain using an anti-neuroblastoma monoclonal antibody revealed that the antigen was very similar to mouse L1cam (Wolff, J. M., Frank, R., Mujoo, K., Spiro, R. C., Reisfeld, R. A., Rathjen, F. G., A human Brain Glycoprotein Related To The Mouse Cell Adhesion Molecule L1. *J. Biol Chem.* 263: 11943–11947 (1988)). To conform with the HGMW approved nomenclature, (Human Gene Mapping Workshop, published 1987 in Cytogenet. Cell Genet., Vol. 46, pages 11–28) mouse L1 cell adhesion molecule is referred hereinafter as "L1cam" and human L1 cell adhesion molecule is referred to as "L1CAM".

Recently, partial sequences obtained for a human genomic clone (Djabali, M., Mattei, M. G., Nguyen, C., Roux, D., Demengeot, J., Denizot, F., Moos, M., Schachner, M., Goridis, C., Jordan, B. R., The Gene Encoding L1, A Neural Adhesion Molecule Of The Immunoglobulin Family, Is Located On The X-Chromosome In Mouse And Man, *Genomics* 7: 587–593 (1990)) and a human melanoma cDNA clone (Harper, J. R., Prince, J. T., Healy, P. A., Stuart, J. K., Nauman, S. J., Stallcup, W. B., Isolation And Sequence Of Partial cDNA Clones of Human-L1- Homology Of Human And Rodent-L1 In The Cytoplasmic Region, *J. Neurochem.* 56: 797–804 (1991)) confirmed that a human L1-like molecule exists.

Further studies localized the gene for human L1 to the q28 band on the X chromosome (Djabali, M., Mattei, M. G., Nguyen, C., Roux, D., Demengeot, J., Denizot, F., Moos, M., Schachner, M., Goridis, C., Jordan, B. R., The Gene Encoding L1, A Neural Adhesion Molecule Of The Immunoglobulin Family, Is Located on the X-Chromosome in Mouse and Man, *Genomics* 7: 587–593 (1990)), the homologous region to the A6-B region of the mouse X chromosome where the L1 cam gene is located.

The knowledge that a L1-like molecule exists in humans leads to the conclusion that L1CAM may be important in promoting axon regeneration in trauma or disease states of the human nervous system. Therefore, the Applicants have isolated and purified L1 from human brain and conducted in vitro experiments on the natural substance that demonstrate that human L1CAM, like chick and mouse L1 cam, can support neuron attachment and neurite growth.

In addition, Applicants have cloned and sequenced cDNAs (SEQ ID NOS: 3–6) encompassing the entire coding region of L1CAM (SEQ ID NO: 2). This information will allow future studies on the structure and function of L1CAM and permit the construction of cell lines expressing L1CAM for in vitro and in vivo experiments on nerve growth and regeneration.

These and other objects and features of the invention will be apparent from the following description and from the claims.

SUMMARY OF THE INVENTION

In one aspect, the present invention is directed to the isolation and purification of an L1-like molecule (i.e. L1CAM) from human brain. It has been found that the isolated L1CAM molecule supports neurite growth in vitro. Applicants have also cloned (SEQ ID NOS: 3–6) and sequenced the entire coding region of human L1CAM (SEQ ID NO: 2), and found that it shows a very high degree of homology to mouse L1 cam with 92% identity at the amino acid level. This similarity suggest that L1 CAM is an important molecule in normal human nervous system development and nerve regeneration. Overall, there is substantially less homology to chick Ng-CAM; they are 40% identical at the amino acid level but many regions are highly conserved. Comparison of the sequences from human, mouse, chick and Drosophila, indicates that the L1 immunoglobulin domain 2 and fibronectin type III domain 2 are strongly conserved and thus are likely functionally important.

In another aspect, present invention provides for a method for isolating and completely characterizing the coding sequence of human L1CAM (SEQ ID NO: 2). Moreover, the invention provides various methods for using the identified nucleotide sequence (or DNA fragments thereof (SEQ ID NOS: 3–6)) for evaluating the function of human L1CAM in normal and damaged tissue.

In an additional aspect, the invention relates to procedures for determining and/or correcting genetic or acquired disorders of the central nervous system axonal tract.

Furthermore, the invention provides for use of the sequence (SEQ ID NO: 2) information characterized to synthesize the L1CAM glycoprotein itself or fragments thereof. Along this line, the invention relates to use of the identified nucleotide sequence (or DNA parts thereof (SEQ ID NOS: 3–6)) to synthesize L1CAM or modifications of this glycoprotein into microorganisms or other hosts which use the gene to synthesize the glycoprotein.

In a further aspect, the present invention provides for use of the cDNAs (SEQ ID NOS: 3–6) for comparison of recombinant L1CAM with product purified from human brain. This permits functional studies on the recombinant molecule to be conducted. Similarly, use of the characterized cDNAs, permits the construction of cell lines expressing normal and altered L1CAM for use in transplantation and regeneration studies.

In still another aspect, the invention provides for recombinant DNA cloning vectors and transformed hosts which contain a vector which has a cDNA insert (SEQ ID NOS: 3–6) which codes for L1CAM .

BRIEF DESCRIPTION OF THE DRAWINGS

The following is a brief description of the drawings which are presented for the purpose of illustrating the invention and not for the purpose of limiting same.

FIGS. 3A and 3B shows the nucleotide (bottom line) and deduced amino acid (top line) sequence of the coding portion of L1CAM (SEQ ID NO: 2). Untranslated nucleotides are not shown. The boxed nucleotides represent areas of discrepancy as compared with other published L1CAM sequence data. Underlined regions represent the oligonucleotides used for screening the library. The asterisk represents a stop codon. The nucleotide sequence for L1CAM is available through GenBank Data L1 braries under Accession No. M64296.

FIGS. 4A and 4B shows a comparison at an amino acid level of L1CAM domains with corresponding domains in L1 cam and chick Ng-CAM. Gaps were introduced to maximize identities between the sequences. Identical residues are represented by a hash mark. The amino acids shown as being the transmembrane region include the link between the Fn-5 domain and the presumed membrane spanning region that begins with GWFI. The amino acids shown in FIG. 4 correspond to the amino acid sequences, SEQ ID. NOS. 9–44, set forth in the Sequence Listing.

DETAILED DESCRIPTION OF THE INVENTION

L1CAM Purification

L1CAM was isolated and purified by immunoaffinity chromatography using similar purification methods previously described by the Applicants (Lemmon, V., Farr, K., Lagenaur, L1 Mediated Axon Outgrowth Occurs Via A Homophilic Binding Mechanism. *Neuron* 2: 1597–1603 (1989)). Briefly, neural membranes from 12 day full term neonatal human brain (the infant succumbed from complications of Trisomy 18) were isolated on sucrose gradients and then extracted with 1% deoxycholate. The extract was then run over a 74-5H7 IgG monoclonal antibody to L1 cam affinity column (Lemmon, V., Farr, K., Lagenaur, C., L1 Mediated Axon Outgrowth Occurs Via A Homophilic Binding Mechanism. *Neuron* 2: 1597–1603 (1989)). Antigens were eluted with 0.1 M diethylamine (pH 11.5) and the solution rapidly neutralized with Tris-HCl. Fractions were then dialyzed against PBS overnight. Gel electrophoresis of the purified product was performed on a 5% SDS-polyacrylamide gel.

Figure 1:
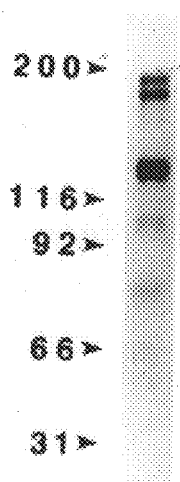
FIG. 1 is a photograph of a silver stained SDS-PAGE gel of immunopurified L1CAM. The molecular weight standards are indicated at the left.

A silver stained SDS-polyacrylamide gel of purified L1CAM is shown in FIG. 1. Notable is the characteristic doublet of bands at 190-180 kDa, a major band at 130 kDa, and minor bands at 105 kDa, 80 kDa, and 62 kDa. This is similar to the pattern reported by others for L1CAM (Mujoo, K., Spiro, R. C., Reisfeld, R. A., Characterization Of A Unique Glycoprotein Antigen Expressed On The Surface Of Human Neuroblastoma Cells. *J Biol. Chem.* 261: 10299–10305 (1986); and, Wolff, J. M., Frank, R., Mujoo, K., Spiro, R. C., Reisfeld, R. A., Rathjen, F. G., A Human Brain Glycoprotein Related To The Mouse Cell Adhesion Molecule L1. *J Biol Chem.* 263: 11943–11947 (1988)), chick Ng-CAM (Burgoon, M. P., Grumet, M., Mauro, V., Edelman, G. M., Cunningham, B. A., Structure Of The Chicken Neuron-Glial Cell Adhesion Molecule, Ng-CAM: Origin Of The Polypeptides And Relation To The Ig Superfamily. *J. Cell Biol.* 112: 1017–1029 (1991)) and L1 cam (Sadoul, K., Sadoul, R., Faissner, A., Schachner, M., Biochemical Characterization Of Different Molecular Forms Of The Neural Cell Adhesion Molecule L1. *J. Neurochem* 50: 510–521 (1988)).

Cell Culture

Functional assays of the L1 CAM purified from human brain were performed by two neuronal culture methods. Dissociated P1 rat cerebellar cells were plated on L1 CAM-nitrocellulose coated plates as previously described by Applicant (Lemmon, V., Farr, K., Lagenaur, C., L1 Mediated Axon outgrowth Occurs Via A Homophilic Binding Mechanism. Neuron 2: 1597–1603 (1989)). E7 chick retinal strips were grown on L1 CAM-nitrocellulose coated plates based on a system developed by Halfter et al. (Halfter, W., Claviez, M., Schwarz, U., Preferential Adhesion Of Tectal Membranes To Anterior Embryonic Chick Retina Neurites. *Nature* 292: 67–70 (1981)). Plain nitrocellulose coated with bovine serum albumin was used as a negative control substrate.

Figure 2:
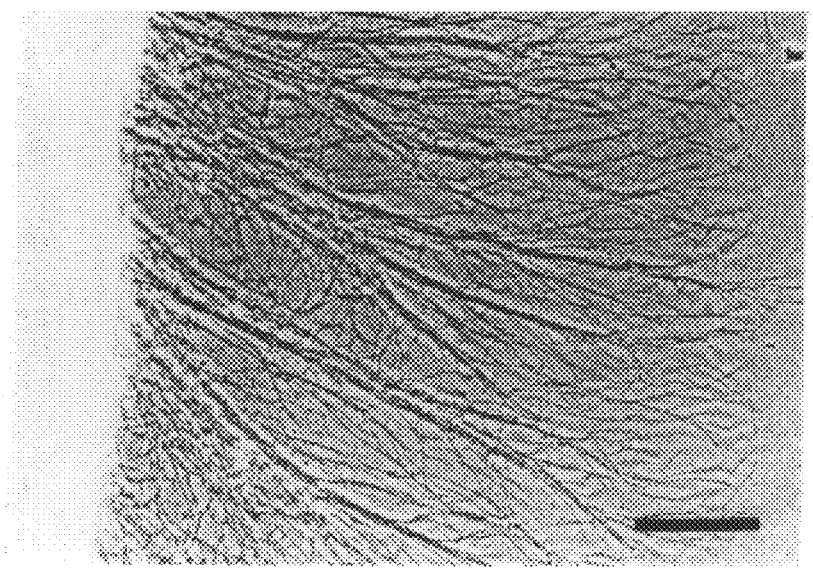
FIG. 2 is a microphotograph of E7 chick retinal explants grown on L1CAM coated dishes. Control dishes coated with BSA had no neurite outgrowth. Scale, bar=100 microns.

As shown in FIG. 2, purified L1 CAM was extremely potent in supporting neurite outgrowth. Chick retinal explants produced extended defasciculated neurites on L1CAM (FIG. 2) and dissociated rat cerebellar neurons grew long neurites. Controls grown on nitrocellulose without L1 CAM showed poor attachment and no neurite extension.

Molecular Cloning

A human fetal brain cDNA library in Lambda ZAP® II (Stratagene, La Jolla, Calif.) was amplified in the *E. coli* strain XL1 -Blue (Stratagene, La Jolla, Calif.). The library was probed with a $^{32}$P 5' end labelled synthetic degenerate oligonucleotides, 50 nucleotides in length (SEQ ID NO: 7) (i.e. GAGGACACCCAGGTGGACTCTGAGG-CCCGACCG ATGAAAGATGAGACCTT), corresponding to a region that is highly conserved between L1 cam and the rat homologue NILE glycoprotein (Prince, J. T., Milona, N., Stallcup, W. B., Characterization Of A Partial cDNA Clone For The NILE Glycoprotein And Identification Of The Encoded Polypeptide Domain. *J. Neurosci* 9: 1825–1834 (1989)). The screening was carried out overnight at 30° C. in a solution containing 6×SSC, 5×Denhardts, 0.5% SDS (sodium dodecyl sulfate), 20% formamide and 100 ug/ml salmon sperm DNA.

Figure 5:
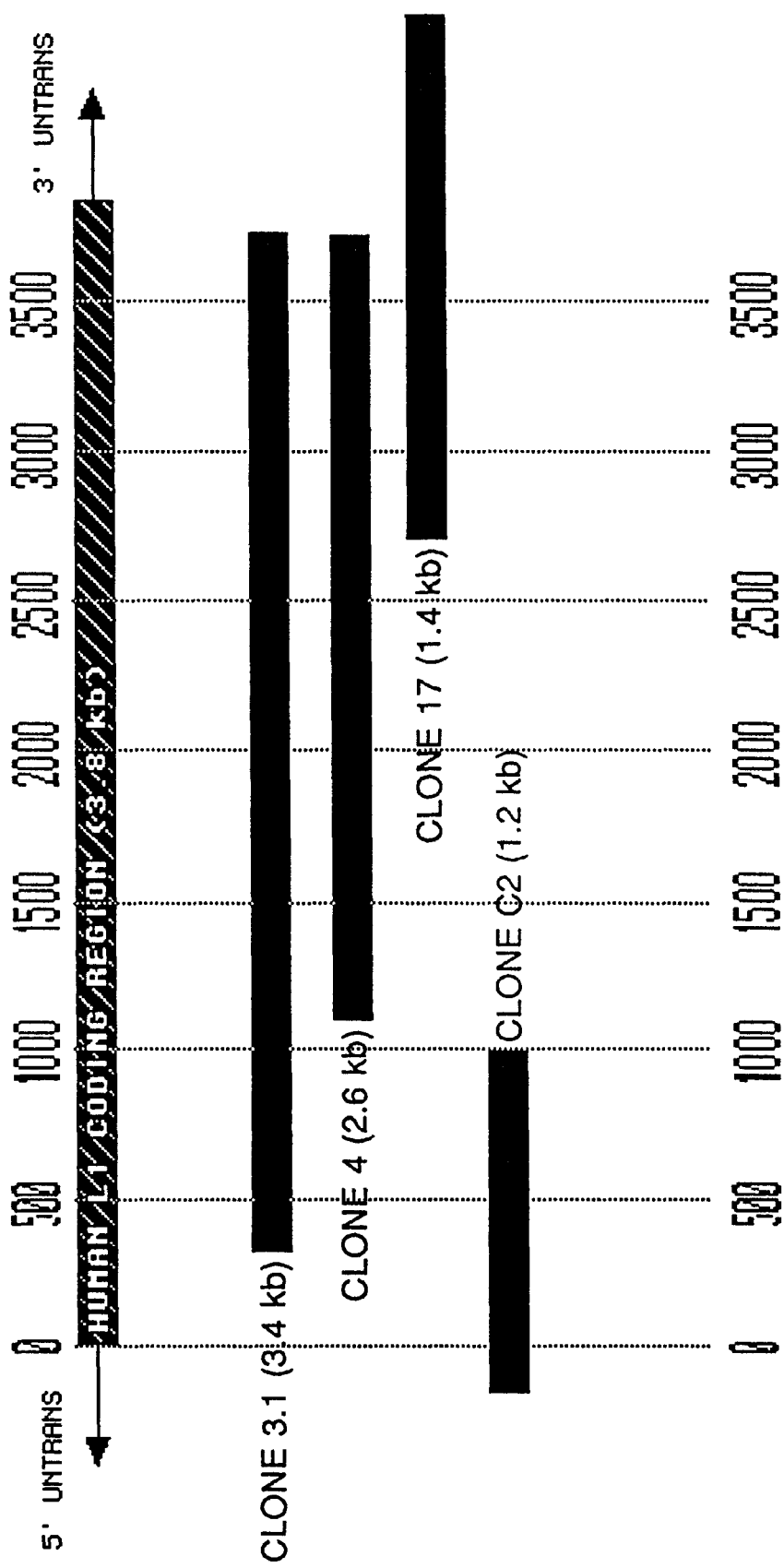
FIG. 5 is a map of the four cloned cDNAs (i.e. 3.1 (SEQ ID NO: 3), 4 (SEQ ID NO: 4), 17 (SEQ ID NO: 5) and C2 (SEQ ID NO: 6)) that code for parts of L1CAM. A scale demonstrating the size differences in base pairs is shown beside the cloned cDNAs.

A total of 3×10$^6$ placques were screened, representing a three-fold screening of the library. Twenty placques were initially positive, however only three of the clones initially isolated from the cDNA library remained positive after successive rounds of screening and proved subsequently to correspond to L1CAM cDNA. After excision of the inserts from the phage vector, these clones were determined to be approximately 3.4, 2.6, and 1.4 kb in length by gel diffusion and 3.2, 2.6, and 1.7 kb in length by sequencing and were designated 3.1 (SEQ ID NO: 3), 4 (SEQ ID NO: 4) and 17 (SEQ ID NO: 5) respectively. See FIG. 5. Because none of these contained a start methionine and initial signal sequence, a second screening of the library was performed using a 40 base oligonucleotide (SEQ ID NO: 8) (i.e. TGCCACGCCCACTTCCCAGGCACCAGGACCATCA-TTCAGA) deduced from sequencing the 5' end of clone 3.1 (SEQ ID NO: 3). A positive clone from this screening, C2 (SEQ ID NO: 6), contained an initiation codon preceded by a stop codon and followed by sequence that corresponded to a hydrophobic stretch of amino acids that is presumed to be a signal sequence, as well as sequence that overlapped with the previously obtained clones. This clone was determined to be 1.2 kb in length by gel diffusion and later about 1.0 kb in length by sequencing.

DNA Sequencing

Double stranded DNA sequencing was carried out by the dideoxynucleotide method (Sanger, F. S., Nicklen, S., Coulson, A. R., DNA Sequencing With Chain Terminating Inhibitors. *Proc. Natl. Acad. Sci. USA* 74: 5463–5467 (1977)) using a Sequenase Kit (USBC, Cleveland, Ohio) and $^{35}$S-deoxyadenosine 5'-(thio) triphosphate from Amersham, Arlington Heights, Ill. The primers for the reactions were custom synthesized. Sequencing primers to the T7 and T3 promoters were used for the initial sequencing, and subsequent sequencing was done using additional synthetic oligonucleotide primers generated from the newly acquired L1CAM sequence. The complete sequence was obtained from both DNA strands. Sequence analysis was carried out using the MacVector® (IBI) sequence analysis program.

Figure 3A:
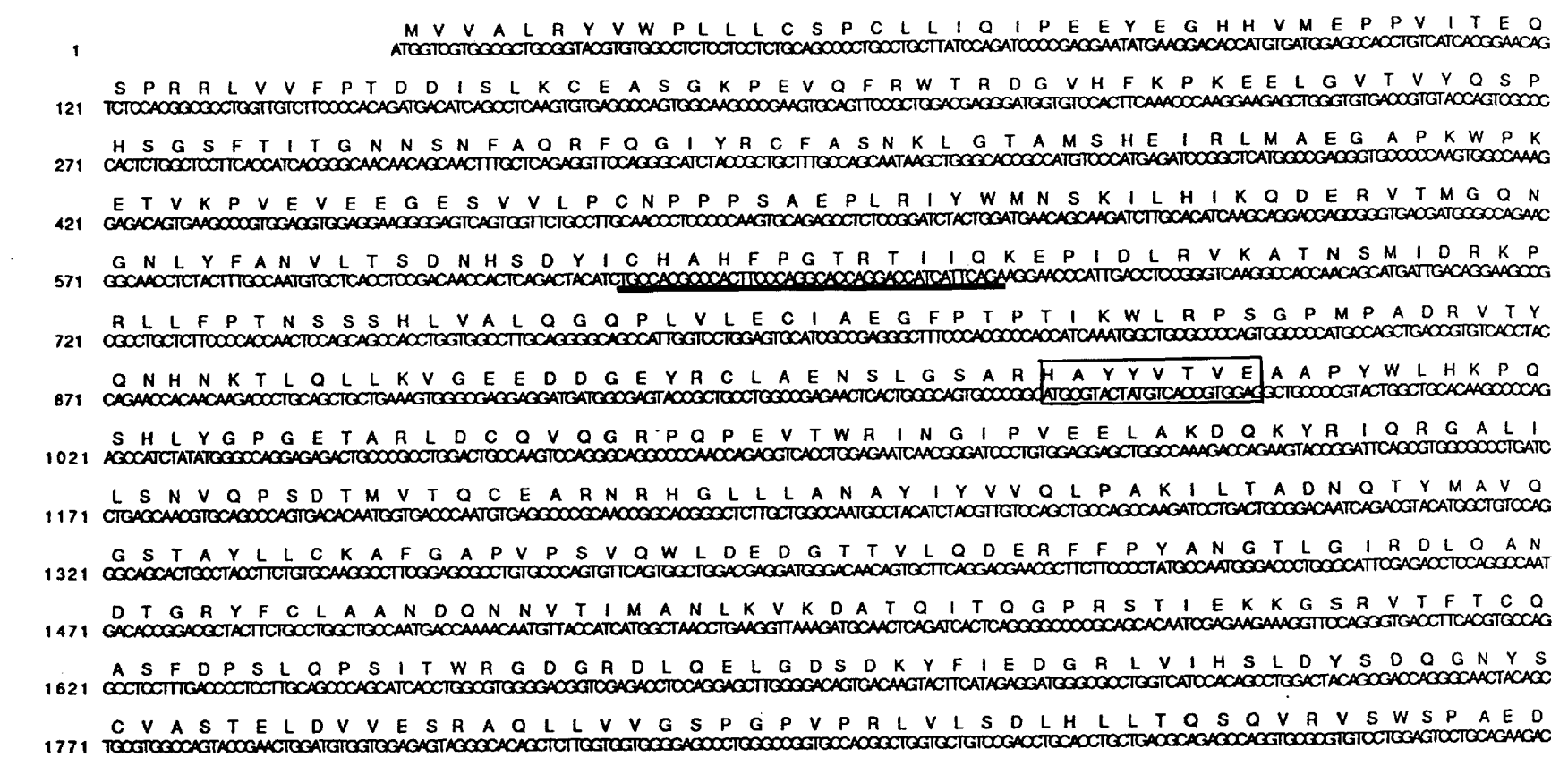
Figure 3B:
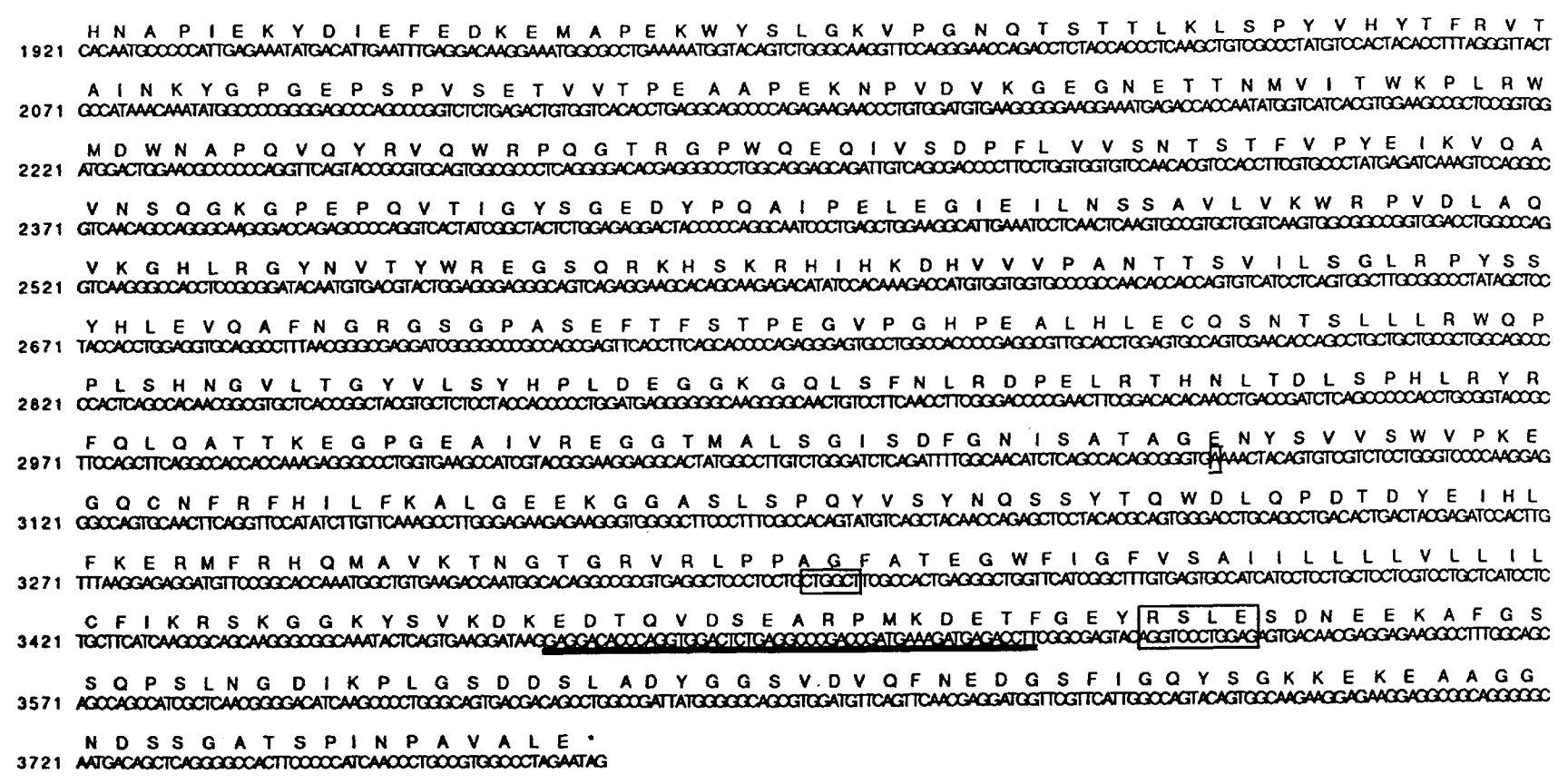

The nucleotide (lower line) and deduced amino acid (upper line) sequence for the L1CAM cDNA coding region (SEQ ID NO: 2) is shown in FIG. 3A and 3B. The open reading frame encodes a protein of 1,256 amino acids and 142,698 Dalton molecular weight. The nucleotide sequence for L1 CAM (SEQ ID NO: 2) has been deposited with EMBL/GenBank Data Libraries under Accession No. M64296.

Figure 4A:
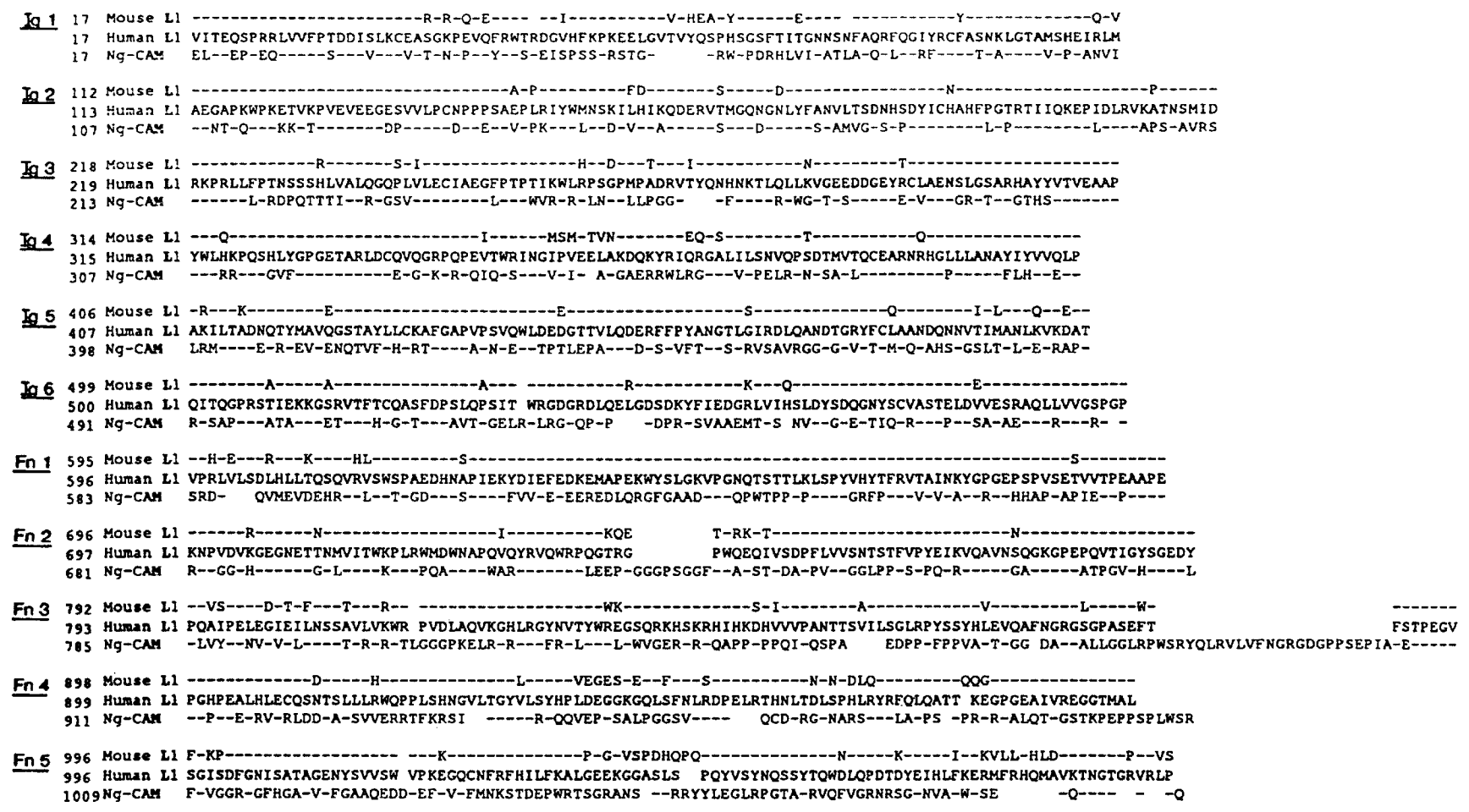

The nucleotide sequences of the human L1CAM and mouse L1 cam cDNAs were compared and found to be 85% identical. At the amino acid level, this rose to 92% overall identity (FIG. 4A and 4B).

Structurally, L1-related molecules are similar to other immunoglobulin superfamily cell adhesion molecules having a motif of repeating immunoglobulin domains followed by fibronectin type III domains. The L1 -like molecules in particular have 6 repeating immunoglobulin C2 (Ig) domains followed by 5 repeating fibronectin type III (Fn) domains (Moos, M., Tacke, R., Scherer, H., Teplow, D., Fruh, K., Schachner, M., Neural Adhesion Molecule L1 As A Member Of The Immunoglobulin Superfamily With Binding Domains Similar To Fibronectin. *Nature* 334: 701–703 (1988); and, Burgoon, M. P., Grumet, M., Mauro, V., Edelman, G. M., Cunningham, B. A., Structure Of The Chicken Neuron-Glial Cell Adhesion Molecule, Ng-CAM: Origin Of The Polypeptides And Relation To The Ig Superfamily. *J. Cell Biol.* 112: 1017–1029 (1991)). These are linked to a cytoplasmic portion of the molecule by a transmembrane domain.

A domain by domain comparison of the protein sequence of human L1CAM to mouse L1 cam, chick Ng-CAM, and Drosophila neuroglian was performed and is summarized below in Table 1.

the relatively low sequence (40%) identity between the two molecules (Burgoon, M. P., Grumet, M., Mauro, V., Edelman, G. M., Cunningham, B. A., Structure Of The Chicken Neuron-Glial Cell Adhesion Molecule, Ng-CAM: Origin Of The Polypeptides And Relation To The Ig Superfamily. *J. Cell Biol.* 112: 1017–1029 (1991)). In contrast, mouse NCAM is about 80% identical with chick NCAM and rat fibronectin is about 80% identical with chick fibronectin. They also state that "experiments to identify an L1 homologue in chickens and an Ng-CAM homologue in mice have not yet revealed such molecules".

Despite the poor sequence homology between Ng-CAM and mammalian L1, there are many similarities among the molecules. If conservative amino acid substitutions in

TABLE 1

Percentage Identity of Amino Acids in Different Domains Compared to Human L1

| Domain | Ig 1 | Ig 2 | Ig 3 | Ig 4 | Ig 5 | Ig 6 | Fn 1 | Fn 2 | Fn 3 | Fn 4 | Fn 5 | TM | CP |
|---|---|---|---|---|---|---|---|---|---|---|---|---|---|
| ML1cam | 83 | 93 | 91 | 87 | 90 | 93 | 89 | 89 | 86 | 82 | 75 | 94 | 100 |
| NGCAM | 44 | 66 | 55 | 57 | 39 | 43 | 38 | 56 | 33 | 30 | 18 | 78 | 63 |
| NGCAM* | 62 | 83 | 71 | 79 | 66 | 56 | 67 | 73 | 58 | 49 | 32 | 100 | 75 |
| Neuroglian | 26 | 32 | 27 | 24 | 29 | 32 | 32 | 36 | 31 | 29 | 18 | 22 | 26 |
| Neuroglian* | 41 | 54 | 47 | 49 | 49 | 48 | 51 | 68 | 50 | 52 | 40 | 67 | 40 |

As indicated above, two short stretches of L1CAM nucleotide sequence have been published previously. A comparison of the genomic sequence obtained by Dijalbi. et al. (Djabali, M., Mattei, M. G., Nguyen, C., Roux, D., Demengeot, J., Denizot, F., Moos, M., Schachner, M., Goridis, C., Jordan, B. R., The Gene Encoding L1, A Neural Adhesion Molecule Of The Immunoglobulin Family, Is Located On The X-Chromosome In Mouse And Man. *Genomics* 7: 587–593 (1990)) with Applicants is an identical match from nucleotides 991-1091. See FIG. 3A and 3B. The first 23 nucleotides of the Dijalbi sequence, however, did not match Applicants sequence or the L1 cam sequence and likely represents an intron.

The sequence obtained by Harper et al. (Harper, J. R., Prince, J. T., Healy, P. A., Stuart, J. K., Nauman, S. J., Stallcup, W. B., Isolation And Sequence Of Partial cDNA Clones Of Human-L1 - Homology Of Human And Rodent-L1 In The Cytoplasmic Region. *J Neurochem* 56: 797–804 (1991)) from human melanoma cDNA differs from Applicants at L1CAM nucleotides 3528 to 3540 where Harper et al. show a 12 nucleotide deletion. See FIGS. 3A and 3B. Applicants obtained identical sequence for this region from three independent clones and the sequence matches the corresponding mouse nucleotide sequence perfectly. This discrepancy could represent a mutation in the tumor line or a splicing variant. The sequence also varies between nucleotides 3344–3349 where Harper et al. have an extra 3 nucleotides introduced non-sequentially. Interestingly, Applicants found a one amino acid deletion here as compared to the mouse L1 cam sequence with matching of the flanking amino acids on either side. This region was particularly difficult to sequence on the anti-sense strand, requiring dITP reactions to resolve compressions. The coding strand, however, had unambiguous sequence. Applicants found a final difference at base 3086 where Applicants have an A.

A comparison of the sequences of human L1CAM and mouse L1 cam with Ng-CAM in FIG. 4A and 4B raises a question about the relationship between mammalian L1 and Ng-CAM: are they homologous? Burgoon et al. have suggested that Ng-CAM may not be "equivalent" to L1 due to Ng-CAM are permitted, the overall similarity between L1CAM and Ng-CAM rises to 66%. The Ig domains show relatively higher degrees of similarity, up to 83%, with 75% conservation of the cytoplasmic domain. Furthermore, the overall structure of the molecule is preserved from species to species; there are 6 Ig domains and 5 Fn domains in each molecule and each structural domain in the chick molecule is most closely related to the same domain in the human. The domains that show the highest degree of similarity between human and mouse (Ig 2, Fn 2, the transmembrane and cytoplasmic domain) also demonstrate the most similarity between human and chick. The relatively variable domains between human L1 CAM and mouse L1 cam (Ig 1, Fn 4 and Fn 5) also have relatively low homologies between human and chick. This is also true when comparing L1 CAM to Drosophila neuroglian.

Immunological and biochemical experiments demonstrate many similarities between mammalian L1 and Ng-CAM. Antibodies against mammalian L1 from different species crossreact with Ng-CAM. Purification of L1 and Ng-CAM from brain produces a similar polypeptide pattern on SDS-PAGE and there is substantial evidence that there are protease sensitive sites at the same two locations in both L1 and Ng-CAM (Sadoul, R., Kirchhoff, F., Schachner, M., A Protein Kinase Activity Is Associated With And Specifically Phosphorylates The Neural Cell Adhesion Molecule L1 . *J. Neurochem.* 53: 1471–1478 (1988); Prince, J. T., Milona, N., Stallcup, W. B., Characterization Of A Partial cDNA Clone For The NILE Glycoprotein And Identification Of The Encoded Polypeptide Domain. *J. Neurosci.* 9: 1825–1834 (1989); and, Burgoon, M. P., Grumet, M., Mauro, V., Edelman, G. M., Cunningham, B. A., Structure Of The Chicken Neuron-Glial Cell Adhesion Molecule, Ng-CAM: Origin Of The Polypeptides And Relation To The Ig Superfamily. *J. Cell Biol.* 112: 1017–1029 (1991)). The anatomical distribution of L1, despite minor variations, shows striking similarity between chick and mammals. For example, almost all projection axons in the CNS and PNS express L1 or Ng-CAM in the corresponding species.

Functional experiments have shown that anti-L1 and anti-Ng-CAM antibodies disrupt axon fasciculation in both chicks and mammals (Stallcup, W. B., Beasley, L., Involvement Of The Nerve Growth Factor-Inducible Large External Glycoprotein (NILE) In Neurite Fasciculation In Primary Cultures Of Rat Brain. *Proc. Natl. Acad. Sci. USA* 82: 1276–1280 (1985); and, Rathjen, F. G., Schachner, M., Immunocytological And Biochemical Characterization Of A New Neuronal Cell Surface Component (L1 Antigen) Which Is Involved In Cell Adhesion. *EMBO J.* 3: 1–10 (1984)) and inhibit neuron-neuron adhesion (Keilhauer, G., Faissner, A., Schachner, M., Differential Inhibition Of Neurone-Neurone, Neurone-Astrocyte and Astrocyte-Astrocyte Adhesion By L1 , L2 And N-CAM Antibodies. *Nature* 316: 728–730 (1985); Grumet, M., Hoffman, S. ,Edelman, G. M., Two Antigenically Related Neuronal Cell Adhesion Molecules Of Different Specificities Mediate Neuron-Neuron And Neuron-Glia Adhesion. *Proc. Natl. Acad. Sci. USA* 81: 267–271 (1984)). They also perturb migration of granule cells from the external granule cell layer to the internal granule cell layer in the cerebellum (Lindner, J., Rathjen, F. G., Schachner, M., L1 mono- and polyclonal antibodies modify cell migration in early postnatal mouse cerebellum. *Nature* 305: 427–430 (1983); and, Hoffman, S., Friedlander, D. R., Chuong, C.-M., Grumet, M., Edelman, G. M., Differential Contributions Of Ng-CAM And N-CAM To Cell Adhesion In Different Neural Regions. *J. Cell Biol.* 103: 145–158. (1986)).

Finally, studies with purified L1 and with Ng-CAM show that mammalian cells can bind to chick Ng-CAM and that chick neurons can bind to mammalian L1 in a homophilic binding interaction between the L1 cam and the chick Ng-CAM (Lemmon, V., Farr, K., Lagenaur, C., L1 Mediated Axon Outgrowth Occurs Via A Homophilic Binding Mechanism. *Neuron* 2: 1597–1603 (1989)). Therefore, while there are clearly structural differences between Ng-CAM and L1 it seems most likely that they represent homologous and not merely analogous molecules.

Comparison of L1 CAM, L1 cam, rat NILE and chick Ng-CAM confirms previous reports that the cytoplasmic portion of this molecule is very highly conserved, suggesting an important functional role for this region of the molecule (Prince, J. T., Milona, N., Stallcup, W. B., Characterization Of A Partial cDNA Clone For The NILE Glycoprotein And Identification Of The Encoded Polypeptide Domain. *J. Neurosci.* 9: 1825–1834 (1989); and, Harper, J. R., Prince, J. T., Healy, P. A., Stuart, J. K., Nauman, S. J., Stallcup, W. B., Isolation And Sequence Of Partial cDNA Clones of Human-L1- Homology Of Human And Rodent-L1 In The Cytoplasmic Region. *J. Neurochem* 56: 797–804 (1991)). Evidence points to an interaction of L1 with the cytoskeleton, directly or indirectly, because in differentiated neuroblastomas L1 is relatively immobile (Pollerberg, G. E., Davoust, J., Schachner, M., Lateral Mobility Of The Cell Adhesion Molecule-L1 Within The Surface Membrane Of Morphologically Undifferentiated And Differentiated Neuroblastoma Cells. *European Journal of Neuroscience* 2: 712–717 (1990)).

However, on axons and growth cones of chick retinal ganglion cells, L1 is freely diffusible (Drazba, J., Lemmon, V., Cell adhesion molecules 8D9 and NCAM move independently in the plane of axon membranes. *Soc. for Neurosci.*, St. Louis, Mo., (1990)). This suggests that attachment to the cytoskeleton is not a prerequisite for functional binding as is the case for cadherins (Nagafuchi, A., Takeichi, M., Cell binding function of E-cadherin is regulated by the cytoplasmic domain. EMBO J. 7: 3679–3684 (1988)).

The cytoplasmic domain of L1 also may be involved in regulating cell adhesion molecule function. L1 is phosphorylated and is associated with a casein kinase (Sadoul, R., Kirchhoff, F., Schachner, M., A Protein Kinase Activity Is Associated With And Specifically Phosphorylates The Neural Cell Adhesion Molecule L1 . *J. Neurochem.* 53: 1471–1478 (1988)). Anti-L1 antibody binding to L1 on has been shown to alter intracellular calcium and pH (Schuch, U., Lohse, M. J., Schachner, M., Neural Cell Adhesion Molecules Influence Second Messenger Systems. *Neuron* (1989)). Agents such as TPA or okadaic acid that increase cytoplasmic phosphorylation increase fasciculation in a manner consistent with increased affinity of L1 for its ligand (Cervello, M. Lemmon, V., Landreth, G., and Rutishauser, U., Phosphorylation - dependent regulation of neurite fasciculation. *Proc. Natl. Acad. Sci., U.S.A.,* 88: 10548–10552 (1991)). This evidence indicates that L1 either regulates cell function or has its function regulated via its cytoplasmic region.

Interspecies comparison of the amino acid sequence of the extracellular portion of L1 suggests that the Ig domain 2 and Fn domain 2 may have some conserved function since these are the immunoglobulin and fibronectin domains with greatest homology. One possibility is that the Ig domain 2 is important in L1-L1 homophilic binding. The Ig domains 2 and 3 of NCAM are believed to be involved in heparin and cell binding (Frelinger, A. L., Rutishauser, U., Topography of N-CAM Structural And Functional Determinants II. Placement Of Monoclonal Antibody Epitopes. *J. Cell Biol.* 103: 1729–1737 (1986); and, Cole, G. J., Akeson, R., Identification If A Heparin Binding Domain Of The Neural Cell Adhesion Molecule N-CAM Using Synthetic Peptides. *Neuron* 2: 1157–1165 (1989)). This demonstrates that Ig superfamily molecules do not necessarily bind amino terminus to amino terminus. It is also possible that a large region of L1 is involved in L1-L1 binding, similar to the manner in which Ig heavy chains bind to each other; according to this model, the L1 Ig domains would bind in a long parallel or anti-parallel interaction.

This possibility is consistent with the report that all monoclonal antibodies to G4 (thought to be identical with chick Ng-CAM) that were tested were able to inhibit G4-G4 binding (Chang, S., Rathjen, F. G., Raper, J. A., Neurite Outgrowth Promoting Activity Of G4 And Its Inhibition By Monoclonal Antibodies. *J Neurosc R* 25: 180–186 (1990)). No highly positively charged regions were observed in any of the Ig domains that would be analogous to the heparin binding domain in the second Ig domain of NCAM (Cole, G. J., Akeson, R., Identification Of A Heparin Binding Domain Of The Neural Cell Adhesion Molecule N-CAM Using Synthetic Peptides. *Neuron* 2: 1157–1165 (1989)). However, the second Ig domain of L1 and Ng-CAM does have a highly negatively charged region with 4 out of 6 amino acids being aspartic acid or glutamic acid. The third Fn domain of L1 has one region with 9 out of 12 positively charged amino acids. A similar region is present in L1 cam but is absent from chick. Conclusions about structure-function relations must await more detailed experiments using well defined antibodies and mutated forms of L1.

The information provided above extends previous work by providing the entire coding sequence of human L1 CAM and demonstrating that like the related molecules in mouse, rat and chick, L1CAM purified from human brain can support neurite growth. The structural knowledge gained allows comparisons with nearby and more distant species, mice, chick and Drosophila and speculation about structurally important areas of the molecule. The results of in vitro testing of natural L1CAM support the idea that L1CAM is likely to be an important molecule in the development of the human nervous system by providing evidence that L1CAM can mediate neurite growth. This complements reports that the human L1 gene is on the X chromosome in a region were disease of CNS axonal tract development has been mapped (Djabali et al., 1990), and strengthens the need for further understanding of the molecule. Use of the cDNA will enable comparison of recombinant L1CAM with the product purified from human brain and permit functional studies on the recombinant molecule in vitro. Moreover, using the cDNA, cell lines can be constructed expressing normal and altered L1CAM for use in transplantation or regeneration studies.

Furthermore, as a result of the isolation and complete characterization of the nucleotide sequence, the present invention is also directed to the use of the nucleotide sequence (SEQ ID NO: 2) and/or the cDNA clones thereof (SEQ ID NOS: 3–6), for tests that can be used to determine genetic or acquired disorders of neuronal cells using L1CAM DNA probes specific for the identified nucleotide sequence (or DNA fragments thereof) or antibodies to the products coded by the nucleotide sequence or cDNA. More particularly, such uses include a method for identifying the gene coding for the L1CAM which comprises hybridizing a cDNA which codes for part of the L1CAM with human genomic DNA, and determining whether the cDNA anneals to the genomic DNA.

In addition, the present invention relates to the use of gene fragments generated through amplification from human genomic or cloned DNA for detection and analysis of the gene, such as in the detection of mutations. The gene can be used for the production of L1CAM protein. A method for amplifying a nucleotide sequence specific for the human gene for the L1CAM from biological samples containing human genomic DNA using the synthetic oligonucleotide primers of the present invention which contain either a nucleotide sequence from the gene or from the cDNAs encoding exons of the gene (i.e. L1CAM gene), such a method would comprise the steps of synthesizing the oligonucleotides containing the nucleotide sequence wherein the nucleotide sequence are specific for the gene for the L1CAM, allowing the oligonucleotides to anneal to the specific sequences in the sample containing the human genomic DNA, synthesizing a copy of each strand of the DNA by polymerase chain reaction, and denaturing the sample to separate the DNA strands from each other.

Moreover, as elaborated above, the present invention also relates to the potential use of the nucleotide sequence synthesized above for cloning purposes. Other alterative embodiments for new and unique uses of nucleotide sequences, the cDNA clones, etc. may be utilized by procedures that are well known in the art.

The invention has been described with reference to the preferred embodiments. Obviously, modifications and alterations will occur to others upon reading and understanding the preceding detailed description. It is intended that the present invention includes all such alterations and modifications insofar as they come within the scope of the appended claims or the equivalents thereof.

Having thus described the preferred embodiments, the invention is now claimed to be:

1. An isolated DNA molecule for a human L1 cell adhesion molecule comprising the nucleotide sequence (SEQ ID NO: 2) identified in FIGS. 3A and 3B.

2. A CDNA which codes for part of the human L1CAM molecule, identified as cDNA clone c2 (SEQ ID NO: 6).

3. A cDNA which codes for part of the human L1CAM molecule, identified as cDNA clone 3.1 (SEQ ID NO: 3).

4. A cDNA which codes for part of the human L1CAM molecule, identified as cDNA clone 4 (SEQ ID NO: 4).

5. A cDNA which codes for part of the human L1CAM molecule, identified as cDNA clone 17 (SEQ ID NO: 5).

* * * * *